United States Patent
Bolli et al.

(10) Patent No.: US 9,133,179 B2
(45) Date of Patent: *Sep. 15, 2015

(54) 2-METHOXY-PYRIDIN-4-YL-DERIVATIVES

(75) Inventors: Martin Bolli, Allschwil (CH); Cyrille Lescop, Allschwil (CH); Boris Mathys, Allschwil (CH); Keith Morrison, Allschwil (CH); Claus Mueller, Allschwil (CH); Oliver Nayler, Allschwil (CH); Beat Steiner, Allschwil (CH)

(73) Assignee: Actelion Pharmaceuticals Ltd., Allschwil (CH)

( * ) Notice: Subject to any disclaimer, the term of this patent is extended or adjusted under 35 U.S.C. 154(b) by 39 days.

This patent is subject to a terminal disclaimer.

(21) Appl. No.: 13/980,764

(22) PCT Filed: Jan. 18, 2012

(86) PCT No.: PCT/IB2012/050241
§ 371 (c)(1),
(2), (4) Date: Jul. 19, 2013

(87) PCT Pub. No.: WO2012/098505
PCT Pub. Date: Jul. 26, 2012

(65) Prior Publication Data
US 2013/0303514 A1  Nov. 14, 2013

(30) Foreign Application Priority Data
Jan. 19, 2011 (WO) .................. PCT IB2011 050241

(51) Int. Cl.
C07D 413/04 (2006.01)
C07D 413/14 (2006.01)
A61K 31/4439 (2006.01)
A61P 37/00 (2006.01)

(52) U.S. Cl.
CPC ............ C07D 413/14 (2013.01); C07D 413/04 (2013.01)

(58) Field of Classification Search
CPC .. A61K 31/4439; A61P 37/00; C07D 413/04; C07D 413/14
USPC ........................................ 514/340; 546/269.4
See application file for complete search history.

(56) References Cited

U.S. PATENT DOCUMENTS

| | | | |
|---|---|---|---|
| 3,647,809 A | 3/1972 | Reiter et al. | |
| 5,708,180 A | 1/1998 | Beck et al. | |
| 7,605,171 B2 | 10/2009 | Colandrea et al. | |
| 7,605,269 B2 | 10/2009 | Bolli et al. | |
| 7,723,378 B2 | 5/2010 | Bolli et al. | |
| 7,750,040 B2 | 7/2010 | Bolli et al. | |
| 7,834,039 B2 | 11/2010 | Hobson et al. | |
| 7,846,964 B2 | 12/2010 | Bolli et al. | |
| 7,951,794 B2 | 5/2011 | Bolli et al. | |
| 7,981,924 B2 | 7/2011 | Bolli et al. | |
| 8,003,800 B2 | 8/2011 | Bolli et al. | |
| 8,044,076 B2 | 10/2011 | Bolli et al. | |
| 8,133,910 B2 | 3/2012 | Bolli et al. | |
| 8,148,410 B2 | 4/2012 | Bolli et al. | |
| 8,178,562 B2 | 5/2012 | Bolli et al. | |
| 8,288,554 B2 | 10/2012 | Bolli et al. | |
| 8,299,086 B2 | 10/2012 | Bolli et al. | |
| 8,410,151 B2 | 4/2013 | Bolli et al. | |
| 8,575,200 B2 | 11/2013 | Bolli et al. | |
| 8,580,824 B2 | 11/2013 | Bolli et al. | |
| 8,592,460 B2 | 11/2013 | Bolli et al. | |
| 8,598,208 B2 | 12/2013 | Bolli et al. | |
| 8,658,675 B2 | 2/2014 | Bolli et al. | |
| 2007/0021443 A1 | 1/2007 | Ohlmeyer et al. | |
| 2007/0043014 A1 | 2/2007 | Doherty et al. | |
| 2007/0043104 A1 | 2/2007 | Luthman et al. | |
| 2007/0270438 A1 | 11/2007 | Bhattacharya et al. | |
| 2008/0113961 A1 | 5/2008 | Nishi et al. | |
| 2008/0306124 A1 | 12/2008 | Albert et al. | |
| 2009/0275554 A1 | 11/2009 | Habashita et al. | |
| 2011/0028448 A1 | 2/2011 | Bolli et al. | |
| 2011/0046170 A1 | 2/2011 | Bolli et al. | |
| 2011/0207704 A1 | 8/2011 | Cusack et al. | |
| 2012/0108638 A1 | 5/2012 | Bolli et al. | |

FOREIGN PATENT DOCUMENTS

| | | |
|---|---|---|
| DE | 10237883 | 3/2004 |
| EP | 0476646 | 3/1992 |

(Continued)

OTHER PUBLICATIONS

Bolli; J. Med. Chem. 2010, 53, 4198-4211.*

(Continued)

*Primary Examiner* — John Mabry
*Assistant Examiner* — Daniel Carcanague
(74) *Attorney, Agent, or Firm* — Hoxie & Associates LLC

(57) ABSTRACT

The invention relates to pyridine derivatives of Formula (I)

Formula (I)

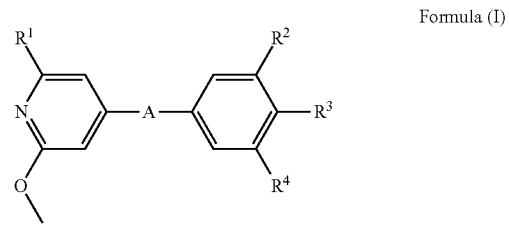

wherein A, $R^1$, $R^2$, $R^3$, and $R^4$ are as described in the description, their preparation and their use as pharmaceutically active compounds. Said compounds particularly act as immunomodulating agents.

23 Claims, No Drawings

(56) References Cited

FOREIGN PATENT DOCUMENTS

| EP | 0702003 | 6/1998 |
|---|---|---|
| EP | 1873153 | 1/2008 |
| JP | 2008120794 | 5/2008 |
| WO | WO 91/15583 | 10/1991 |
| WO | WO 99/46277 | 9/1999 |
| WO | WO 00/45799 | 8/2000 |
| WO | WO 01/12627 | 2/2001 |
| WO | WO 02/068417 | 9/2002 |
| WO | WO 03/062248 | 7/2003 |
| WO | WO 03/062252 | 7/2003 |
| WO | WO 03/105771 | 12/2003 |
| WO | WO 2004/035538 | 4/2004 |
| WO | WO 2004/056789 | 7/2004 |
| WO | WO 2004/103279 | 12/2004 |
| WO | WO 2005/014525 | 2/2005 |
| WO | WO 2005/032465 | 4/2005 |
| WO | WO 2005/058848 | 6/2005 |
| WO | WO 2005/115382 | 12/2005 |
| WO | WO 2006/047195 | 5/2006 |
| WO | WO 2006/114400 | 11/2006 |
| WO | WO 2006/131336 | 12/2006 |
| WO | WO 2007/001973 | 1/2007 |
| WO | WO 2007/085451 | 8/2007 |
| WO | WO 2007/098474 | 8/2007 |
| WO | WO 2007/132307 | 11/2007 |
| WO | WO 2008/037476 | 4/2008 |
| WO | WO 2008/076356 | 6/2008 |
| WO | WO 2008/091967 | 7/2008 |
| WO | WO2008029371 | * 3/2009 |
| WO | WO 2009/043889 | 4/2009 |
| WO | WO 2009/043890 | 4/2009 |
| WO | WO 2009/060278 | 5/2009 |
| WO | WO 2009/151529 | 12/2009 |
| WO | WO 2010/148649 | 12/2010 |

OTHER PUBLICATIONS

Abhandlung; "Stickstoffhaltige Derivate der Mkonsaure und ihre Umwandlung in Pyridin"; Journal fur Prkitsche Chemie, vol. 27, pp. 257-294 (1883).
Alvernhe et al; "Synthesis and Reactivity of 3-chloro-3-trifluoromethylacroleins: Stabilization of the Tetrahedral Intermediate in a Nucleophilic Vinylic Substitution"; Bull. Soc. Chim. Fr.; 131, 1994, 167-172.
Biyouki et al., Synthetic Communications, vol. 28, pp. 3817-3825 (1989).
Bode et al; "Immune Regulation, Etc."; Arch. Immunol. Ther. Exp.; 60: 3-12; (2012).
Brain et al; "Novel Procedure for the Synthesis of 1,3,4-Oxadiazoles from 1,2-diacylhydrazinos Using Polymer-Supported Burgess Reagent under Microwave Conditions"; Tetrahedron Letters, 1999, pp. 3275-3278, vol. 40.
Burstein et al; "Imidazo[1,5-a]pyridine-3-ylidenes-pyridine derived N-heterocyclic carbine ligands", Tetrahedron, vol. 61, pp. 6207-6217; (2004).
Buzard et al; "Expert Opinion on Therapuetic Patents"; vol. 18, No. 10; pp. 1141-1159 (2008).
Caplus 2000:553399 [WO 2000/045799] 2000.
Chakraborti et al; "One-Pot Synthesis of Nitriles from Aldehydes Under Microwave Irradiation: Influence of the Medium and Mode of Microwave Irradiation on Product Formation"; Tetrahedron, 1999, pp. 13265-13268, vol. 55.
Comins et al; "Regiospecific a-Alkylation of 4-Chloro(bromo) pyridine"; J. Org. Chem., vol. 50, pp. 4410-4411, (1985).
Cui et al; Design and Synthesis of Highly Constrained Factor Xa Inhibitors: Amidine-Substituted Bis(benzoy1)-[1,3]-diazepan-2-ones and Bis(benzylidene)- bis(gem-dimethyl)Cycloketones, Bioorganic Medicinal Chemistry, 2003, pp. 3379-3392, vol. 11.
Doucet; Eur. J. Org. Chem.; pp. 2013-2030; 2008.
Ecke et al; "Ortho-Alkylation of Aromatic Amines"; Journal of Organic Chemistry, 1957, pp. 639-642, vol. 22.

Fallahpour, R. A., Synthesis, No. 12, pp. 1665-1667 (2000).
Finch, N., et al., J. Med. Chem., vol. 23, pp. 1405-1410 (1980).
Furnster et al; "Iron Catalyzed Cross-Coupling Reactions"; J. Am. Chem. Soc., 124, 2002, 13856-13863.
Gangloff et al; "Synthesis of 3,5-disubstituted-1,2,4-Oxadiazoles Using Tetrabutylammonium Fluoride as a Mild and Efficient Catalyst"; Tetrahedron Letters, 2001, pp. 1441-1443, vol. 42.
Garcia et al; "Synthesis, Biological Evaluation, and Three-Dimensional Quantitative Structure-Activity Relationship Study of Small-Molecule Positive Modulators of Adrenomedullin"; Journal of Medicinal Chemistry, 2005, pp. 4068-4075, vol. 48.
Gennaro, "Remington: the Science and Practice of Pharmacy", Table of Contents; 20th Edition, Philadelphia College of Pharmacy and Science 2003.
Gibson (Editor); Pharmaceutical Preformulation and Formulation; HIS Health Group, 2001.
Glennon et al; "B-Oxygenated Analogues of the 5-HT2A Serotonin Receptor Agonist 1-(4Bromo-2,5-dimethoxypheny1)-2-aminopropane", Journal of Medicinal Chemistry, 2004, pp. 6034-6041, vol. 47.
Golub et al, "Molecular Classification of Cancer: Class Discovery and Class Prediction by Gene Expression Monitoring"; Science, 1999, vol. 286, 531-537.
Gould; "Salt Selection for Basic Drugs", International Journal of Pharmaceutics, 1986, pp. 201-217, vol. 33.
Gronowitz et al; "On the Synthesis of Branched Saturated Fatty Acids"; Lipids, vol. 28, 1993, 889-897.
Greene et al, "Protective Groups in Organic Synthesis", Table of Contents; 3rd Edition, Wiley New York, 1991.
Gura; "Systems for Identifying New Drugs are Often Faulty"; Cancer Models; Science, vol. 278, No. 5340, pp. 1041-1042; Nov. 1997.
Habermehl, N. C., et al., Inorganic Chem., vol. 68, pp. 7316-7321 (2003).
Hamze et al; "Synthesis of Various 3-Substituted 1,2,4-Oxadiazole Containing Chiral B- and a-Amino Acids from Fmoc-Protected Aspartic Acid"; J. Org. Chem., 68, 2003, 7316-7321.
Harris, M.C., J. Org. Chem., vol. 64, pp. 6019-6022 (1999).
Hla et al; "An Abundant Transcript Induced in Differentiating Human Endothelial Cells Encodes a Polypeptide with Structural Similarities to GProtein-Coupled-Receptors"; The Journal of Biological Chemistry, 1990, pp. 9308-9313, vol. 265, No. 16.
Hu et al; "Sphingosine-1-phosphate, etc."; Mol. Biol. Rep.; 38:4225-4230 (2011).
Inouye et al; "Saccharidew-Dependent Induction of Chiral Helicity in Achiral Synthetic Hydrogen-Bonding Oligomers"; J. Am. Chem. Soc., vol. 126; pp. 2022-2027; (2004).
Jo et al; "Spingosine-1-phosphate, Etc."; Kidney International; 73, 1220-1230; (2008).
John et al; "Reactions of (Difluoroamino) Difluoroacetonitrile and (Difluoroamino) Difluoroacetamidoxime", Inorganic Chemistry; 1988, pp. 3100-3104, vol. 27.
Johnson et al; "Relationships Between Drug Activity in NCI Preclinical In Vitro and In Vivo Models and Early Clinical Trials"; British Journal of Cancer; 64(10): 1524-1431; (2001).
Kaboudin et al; "One-Pot Synthesis of 1,2,4-Oxadiazoles Mediated by Microwave Irradiation Under Solvent-Free Condition"; Heterocycles, 2003; pp. 2287-2292, vol. 60, No. 10 (2003).
Kaminski T. et al, J. Org. Chem., vol. 19, pp. 3855-3860 (2003).
Katz, R. B. et al., Syn. Communications, vol. 19, pp. 317-325 (1989).
Kerins, F., et al., "Generation of Substituted Styrenes via Suzuki Cross-Coupling of Aryl Halides with 2,4,6-Trivinylcyclotriboroxane", J. Org. Chem., vol. 67 pp. 4968-4971, (2002).
Khlestkin et al; "Recent Advances in the Application of A, O-dialkylhydroxylamines in Organic Chemistry"; Current Organic Chemistry, 7; 2003; 967-993.
Kiryanov et al; "Synthesis of 2-Alkoxy-Substituted Thiophenes, 1,3-Thiazoles, and Related S-Heterocycles via Lawesson's Reagent-Mediated Cyclization under Microwave Irradiation: Applications for Liquid Crystal Synthesis"; Journal of Organic Chemistry, 2001, pp. 7925-7929, vol. 66.
Kocienski, "Protecting Groups", Thieme Stuggart, 1994; Introduction.

(56) References Cited

OTHER PUBLICATIONS

Lala et al; "Role of Nitric Oxide in Tumor Progression: Lessons From Experimental Tumors"; Cancer and Metastasis Reviews (1998), 17, 91-106.
Lamattina; "The Synthesis of 2-Amino-4-(4-imidazolyl)pyridines"; J. Heterocyclic Chem.; 20; 1983; 533-538.
Matsushita H., et al., J. Org. Chem., vol. 47, pp. 4161-4165 (1982).
Mentzel et al; "N-Methoxy N-methyl amides (Weinred amides) in Modern Organic Synthesis"; Journal fur Praktische Chemie Chiker-Zeitung; 339; 1997; 517-524.
Meyer et al; "Synthesis of New 1,2,4- and 1,3,4-Oxadiazole Derivatives"; Synthesis; 2003; pp. 899-905, No. 6.
Meyer Zu Heringdorf et al; "Pharmacology of the Sphingosine-1-Phosphate Signalling System"; Sphingolipids: Basic Science and Drug Development; Handbook of Experimental Pharmacology 215, pp. 239-253; 2013.
Nguyen et al; "Combined Directed Ortho Metalation/Cross-Coupling Strategies: Synthesis of the Tetracyclic A/B/C/D Ring Core of the Antitumor Agent Camptothecin"; J. Org. Chem., vol. 69, pp. 7816-7821; (2004).
File History for U.S. Appl. No. 12/310,801 (AC-68-US).
File History for U.S. Appl. No. 12/310,763 (AC-69-US).
File History for U.S. Appl. No. 12/442,203 (AC-71-US).
File History for U.S. Appl. No. 12/531,374 (AC-83-US).
File History for U.S. Appl. No. 12/637,918 (AC-91-US).
File History for U.S. Appl. No. 12/738,110 (AC-94-US).
File History for U.S. Appl. No. 12/747,280 (AC-95-US).
File History for U.S. Appl. No. 12/920,569 (AC-103-US).
File History for U.S. Appl. No. 12/920,656 (AC-104-US).
File History for U.S. Appl. No. 12/920,574 (AC-105-US).
File History for U.S. Appl. No. 13/383,619 (AC-127-US).
Paine, "A Convenient Synthesis of Nicotinate Esters from 3-cyanopyridones"; J. Heterocyclic; 1987; vol. 24, pp. 351-355.
Patani et al; "Bioisosterism: A Rational Approach in Drug Design"; Chem. Rev. 1996, vol. 96, No. 8, pp. 3147-3176.
Pesson et al; "Antibacteriens de Syntheses—Derives de L'acide Pipemidique"; Eur. J. Med. Chem.; 5; 1980; 263-268.
Pierrat, P. et al., Synlett., No. 13, pp. 2319-2322 (2004).
Poulain et al; "Parallel Synthesis of 1,2,4-oxadiazoles from Carboxylic Acids Using an Improved, Uronium-based, Activation"; Tetrahedron Letters, 2001, pp. 1495-1498, vol. 42.
Remington, "The Science and Practice of Pharmacy", 21st Edition (2005), Part 5—Table of Contents, "Pharmaceutical Manufacturing", Published by Lippincott Williams & Wilkins.
Roberts et al; "Sphingosine 1-phosphate Receptor Agonists: A Patent Review"; Expert Opinion; The Scripps Research Institute, Dept. Of Chemistry; 2013; pp. 1-25.
Robinson; "Medical Therapy of Inflammatory Bowel Disease for the 21st Century"; Eur. J. Sug. 164, Suppl. 582, pp. 90-98 (1998).
Roth et al; "2-4-Diamino-5-benzylyrimidines and Analogs as Antibacterial Agents"; J. Med. Chem.; 1988; vol. 31, No. 1; pp. 122-129.
Sato et al; "Synthesis and Evaluation of Substituted 4-alkoxy-2-aminopyridines as Novel Neuropeptide Y1 Receptor Antagonists", Bioorganic and Medicinal Chemistry Letters, 2004, pp. 1761-1764, vol. 14.
Schurer et al; ACS Chemical Biolog, vol. 3; No. 8; pp. 486-498; 2008.
Silverman; "The Organic Chemistry of Drug Design and Drug Action"; 2004; Elsevier, pp. 29-32.
Silverman; "The Organic Chemistry of Drug Design and Drug Action"; 2004; Elsevier, pp. 9.
Simeone et al; "Modification of the Pyridine Moiety of Non-peptidyl Indole GnRH Receptor Antagonists"; Bioorganic & Medicinal Chemistry Letters; Volo. 12, pp. 3329-3332; (2002).
Simone; "Oncology: Introduction"; Cecil Textbook of Medicine, 20th Edition; vol. 1; pp. 1004-1010; (1996).
Singh et al; "The Growing Synthetic Utility of Weinreb's Amide"; Journal fur Praktische Chemie; 342; 2000; 340-347.
Spiegel et al; "Nature Reviews Immunology"; vol. 11, No. 6; pp. 403-15; Jun. 2011.
Srivastava et al; "Synthesis of 3-Aryl-5-[Thien-3-Yl Methy1]-1,2,4-Oxadiazoles", Synthetic Communications, 1999, pp. 1437-1450, vol. 29.
Stauffer S. et al., Organic Letters, vol. 2, No. 10, pp. 1423-1426 (2000).
Suzuki et al; "Synthesis of the Selective 5-Hydroxytryptamine 4 (5-HT4) Receptor Agonist (+)-(S)-2-Chloro-5-methoxy-4-[5-(2-plperydylmethyl)-1,2,4- oxadiazol-3-yl] aniline"; Chem. Pharm. Bull.; 1999, pp. 120-122, vol. 47.
Szczepankiewicz et al; "Aminopyridine-based c-Jun N-Terminal Kinase Inhibitors with Cellular Activity and Minimal Cross-Kinase Activity"; J. Med. Chem., vol. 49, pp. 3563-3580; (2006).
Trapani et al; "Propofol Analgoues. Synthesis, Relationships between Structure and Affinity at Gabaa Receptor in Rat Brain, and Differential Electrophysiological Profile at Recombinant Human Gabaa Receptors"; Journal of Medicinal Chemistry, 1998, pp. 1846-1854, vol. 41.
Tsukerman et al; "Basicity and Structure of .alpha., .beta. -unsaturated Ketones of a Heterocyclic Series. VII. Methyl-substituted Analogs of Chalcones"; Chemical Abstracts Service; XP002467039; STN Databse Accession No.; 1971: 87024.
Van Der Giet et al; "Relevance and Potential, Etc."; Biol. Chem.; 389, pp. 1381-1390; (2008).
Vermonden et al; "Synthesis of 4-functionalized terdendate pyridine-based ligands"; Tetrahedron, vol. 59, pp. 5039-5045; (2003).
Wagaw S. et al., J. Org. Chem., vol. 61, pp. 7240-7241 (1996).
Wild et al; "Asymmetric Synthesis of (S)-(--)-acromelobic Acid"; Eur. J. Org. Chem.; 2003; pp. 4445-4449.
Wolfe J. P. et al., J. Org. Chem. vol. 65, pp. 1158-1174 (2000).
Xu et al; "Acyclic Analogues of Adenosine Biphosphates as P2Y Receptor Antagonists: Phosphate Substitution Leads to Multiple Pathways of Inhibition of Platelet Aggregation"; Journal of Medicinal Chemistry, 2002, pp. 5694-5709, vol. 45.
Yan et al, "Discovery of 3-arylpropionic Acids as Potent Agonists of Spingosine-1-phosphate Receptor-1 (S1P1) with High Selectivity Against All Other Known S1P Receptor Subtypes"; Bioorganic and Medicinal Chemistry Letters, 2006, pp. 3679-3683, vol. 16, No. 14.
Zhen et al, "Discovery of Potent 3,5-Diphenyl-1,2,4-oxadiazole Sphingosine-1-phosphate-1 (S1P1) Receptor Agonists with Exceptional Selectivity Against S1P2 and S1P", Journal of Medicinal Chemistry, 2005, pp. 6169-6173, vol. 48, No. 20.
Ziener, U. et al., Chemistry-A European Journal, vol. 6, pp. 41332-4139 (2000).
Furstner, A. et al. Angew. Chem; vol. 114, Nr. 4, pp. 632-635; 2002.
Furstner, A. et al., "Iron-Catalyzed Cross-Coupling Reactions of Alkyl-Grignard Reagents with Aryl Chlorides, Tosylates, and Triflates", Angew. Chem., Int. Ed., (2002) vol. 41, No. 4, pp. 609-612.
File History of U.S. Appl. No. 12/673,918 (AC-91-US).
U.S. Appl. No. 14/402,159, filed Nov. 19, 2014, G. Schmidt.

* cited by examiner

2-METHOXY-PYRIDIN-4-YL-DERIVATIVES

CROSS REFERENCE TO RELATED APPLICATIONS

This application is a United States Application under 35 U.S.C. 371 claiming benefit of PCT Application No. PCT/IB2012/050241, filed on Jan. 18, 2012, which claims the benefit of PCT Application No. PCT/IB2011/050241, filed on Jan. 19, 2011.

FIELD OF THE INVENTION

The present invention relates to S1P1/EDG1 receptor agonists of Formula (I) and their use as active ingredients in the preparation of pharmaceutical compositions. The invention also concerns related aspects including processes for the preparation of the compounds, pharmaceutical compositions containing a compound of the Formula (I), and their use as compounds improving vascular function and as immunomodulating agents, either alone or in combination with other active compounds or therapies.

BACKGROUND OF THE INVENTION

The human immune system is designed to defend the body against foreign micro-organisms and substances that cause infection or disease. Complex regulatory mechanisms ensure that the immune response is targeted against the intruding substance or organism and not against the host. In some cases, these control mechanisms are unregulated and autoimmune responses can develop. A consequence of the uncontrolled inflammatory response is severe organ, cell, tissue or joint damage. With current treatment, the whole immune system is usually suppressed and the body's ability to react to infections is also severely compromised. Typical drugs in this class include azathioprine, chlorambucil, cyclophosphamide, cyclosporin, or methotrexate. Corticosteroids which reduce inflammation and suppress the immune response, may cause side effects when used in long term treatment. Nonsteroidal anti-inflammatory drugs (NSAIDs) can reduce pain and inflammation, however, they exhibit considerable side effects. Alternative treatments include agents that activate or block cytokine signaling.

Orally active compounds with immunomodulating properties, without compromising immune responses and with reduced side effects would significantly improve current treatments of uncontrolled inflammatory diseases.

In the field of organ transplantation the host immune response must be suppressed to prevent organ rejection. Organ transplant recipients can experience some rejection even when they are taking immunosuppressive drugs. Rejection occurs most frequently in the first few weeks after transplantation, but rejection episodes can also happen months or even years after transplantation. Combinations of up to three or four medications are commonly used to give maximum protection against rejection while minimizing side effects. Current standard drugs used to treat the rejection of transplanted organs interfere with discrete intracellular pathways in the activation of T-type or B-type white blood cells. Examples of such drugs are cyclosporin, daclizumab, basiliximab, everolimus, or FK506, which interfere with cytokine release or signaling; azathioprine or leflunomide, which inhibit nucleotide synthesis; or 15-deoxyspergualin, an inhibitor of leukocyte differentiation.

The beneficial effects of broad immunosuppressive therapies relate to their effects; however, the generalized immunosuppression which these drugs produce diminishes the immune system's defense against infection and malignancies. Furthermore, standard immunosuppressive drugs are often used at high dosages and can cause or accelerate organ damage.

DESCRIPTION OF THE INVENTION

The present invention provides novel compounds of Formula (I) that are agonists for the G protein-coupled receptor S1P1/EDG1 and have a powerful and long-lasting immunomodulating effect which is achieved by reducing the number of circulating and infiltrating T- and B-lymphocytes, without affecting their maturation, memory, or expansion. The reduction of circulating T-/B-lymphocytes as a result of S1P1/EDG1 agonism, possibly in combination with the observed improvement of endothelial cell layer function associated with S1P1/EDG1 activation, makes such compounds useful to treat uncontrolled inflammatory diseases and to improve vascular functionality. Prior art document WO 2008/029371 (document D1) discloses compounds that act as S1P1/EDG1 receptor agonists and show an immunomodulating effect as described above. Unexpectedly, it has been found that the compounds of the present invention have a reduced potential to constrict airway tissue/vessels when compared to the corresponding analogs generically claimed in the prior art document D1. The compounds of the present invention therefore demonstrate superiority with respect to their safety profile, e.g. a lower risk of bronchoconstriction.

Compounds generically claimed in D1 (Compounds 1-4, 7, and 10) and Compounds 5, 6, 8, 9, and 11, which can be considered close analogs of Examples 1-4, 7, 45, 5, 6, 35, 41, and 50, respectively, are shown in FIG. 1.

Figure 1: Structure of compounds which are close analogs to the compounds of the present invention.

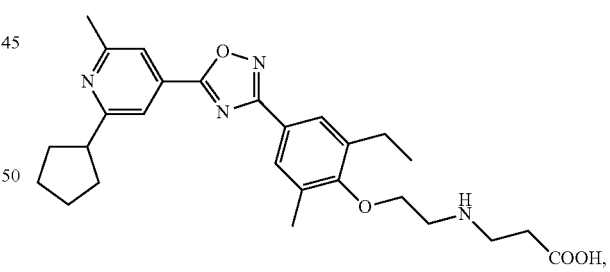

close analog of Example 1 within scope of D1

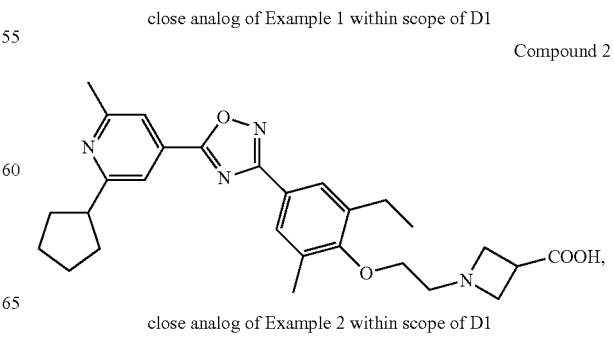

close analog of Example 2 within scope of D1

Compound 3

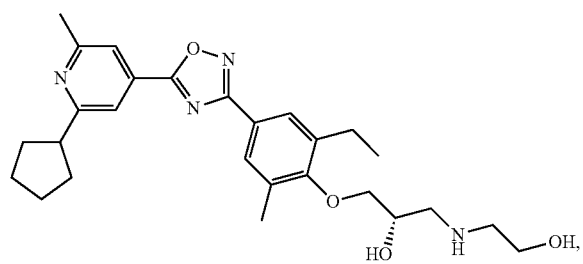

close analog of Example 3 within scope of D1

Compound 4

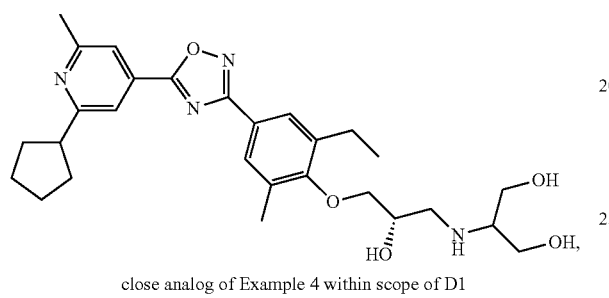

close analog of Example 4 within scope of D1

Compound 5

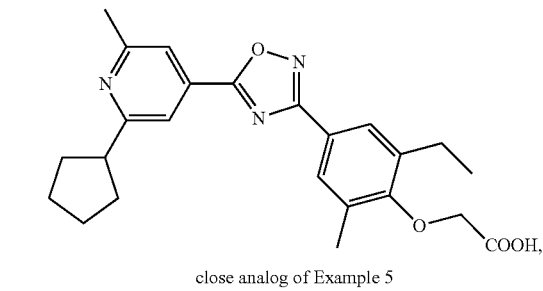

close analog of Example 5

Compound 6

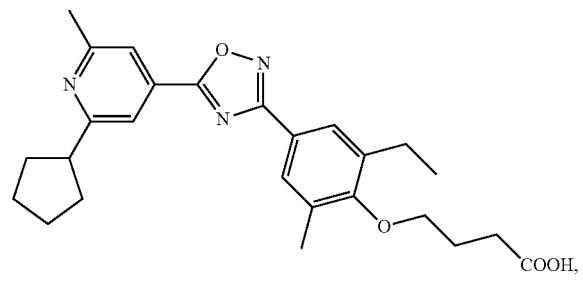

close analog of Example 6

Compound 7

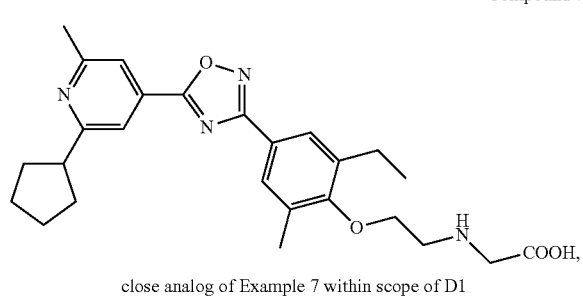

close analog of Example 7 within scope of D1

Compound 8

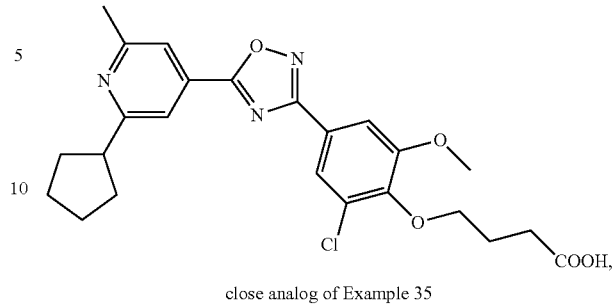

close analog of Example 35

Compound 9

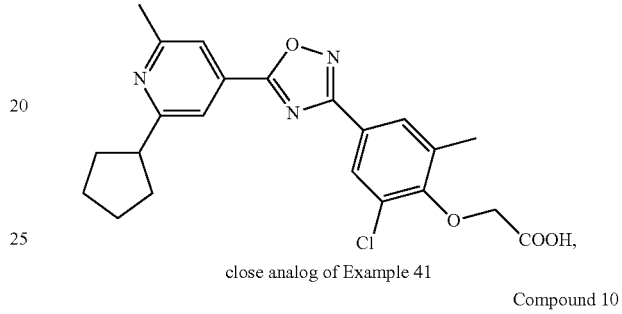

close analog of Example 41

Compound 10

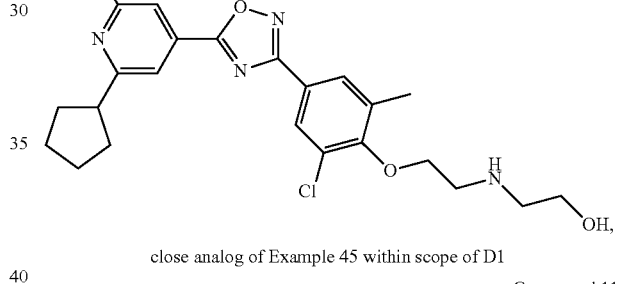

close analog of Example 45 within scope of D1

Compound 11

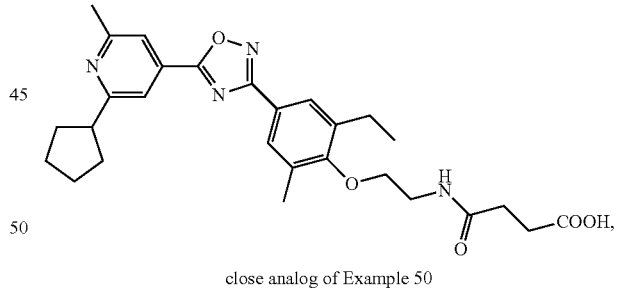

close analog of Example 50

The data on the constriction of rat trachea rings compiled in Table 1 illustrate the superiority of the compounds of the present invention as compared to compounds falling within the scope of prior art document D1.

For instance, the compounds of Example 1 and 2 of the present invention show a significantly reduced potential to constrict rat trachea rings when compared to their close analogs Compound 1 and Compound 2, respectively, said analogs falling within the scope of document D1. While Compound 1 and Compound 2 both show significant rat trachea constriction at 30 nM, the compounds of Examples 1 and 2 show a similar effect at a 10-fold higher concentration only. Likewise, the compounds of Example 3 and 4 of the present invention show a significantly reduced potential to constrict rat trachea rings when compared to their close analogs Compound 3 and Compound 4, respectively, said analogs falling within the scope of document D1. While Compound 3 and Compound 4 both show significant rat trachea constriction at 10 µM, the compounds of Examples 3 and 4 do not trigger any constriction up to 30 µM. The concept of the present invention is further corroborated by the compounds of Example 5 and 6. The compounds of Example 5 and 6 clearly show a reduced potential to constrict rat trachea rings when compared to their corresponding analogs Compound 5 and Compound 6, respectively. Compound 6, for instance, contricts rat trachea rings at a concentration of 10 nM already, while the compound of Example 6 shows a comparable effect at 300 nM only. The compound of Example 7 shows significant constriction at a concentration of 1 µM only while its close analog generically claimed in D1, Compound 7, significantly constricts trachea rings at 100 nM. At a concentration of 100 nM the compound of Example 50 leads to trachea constriction comparable to the one induced by 50 mM KCl. A comparable constriction is observed with Compound 11 at 10 nM already. The Examples discussed so far all share a methyl-ethyl-substitution pattern at the phenyl ring. The following Examples demonstrate that the concept of a reduced potential to constrict rat trachea rings extends to compounds with other substitution patterns at the phenyl ring. For instance, Compound 9 incorporating a chloro-methyl-substitution pattern at the phenyl ring shows significant trachea constriction at 10 and 30 nM, while the compound of Example 41 of the present invention shows no or only negligible constriction at these concentrations. Similarly, full trachea constriction compared to 50 mM KCl is observed at a concentration of 1 µM with Compound 10, while the compound of Example 45 shows significant trachea constriction at 10 µM only. Examples incorporating a chloro-methoxy substitution pattern at the phenyl ring show the same behaviour. As before, the meth-oxy-pyridine compounds of the present invention (e.g. compound of Example 35) show a reduced potential to constrict rat trachea rings when compared to their closest methyl-pyridine analogs (e.g. Compound 8). The compound of Example 54 represents an oxadiazole isomer of Example 6. As shown in Table 1 these two compounds have an almost identical potential to constrict rat trachea demonstrating that the nature of the oxadiazole has no impact on this particular compound property.

Taken together, the data presented in Table 1 clearly demonstrate that the 2-methoxy-pyridine derivatives of the present invention are superior to the corresponding 2-methyl-pyridine analogs, regardless of the nature of A and the substituents $R^2$, $R^3$ and $R^4$ in Formula (I) (vide infra).

TABLE 1

Rat trachea constriction in % of the constriction induced by 50 mM KCl, data represent average values of at least 2 independent experiments.

| Compound | 1 nM | 3 nM | 10 nM | 30 nM | 0.1 µM | 0.3 µM | 1 µM | 3 µM | 10 µM | 30 µM |
|---|---|---|---|---|---|---|---|---|---|---|
| Compound 1 | | n.d. | <5 | 61 | 118 | 126 | 119 | n.d. | | |
| Compound 2 | | n.d. | <5 | 70 | 106 | 160 | 142 | n.d. | | |
| Compound 3 | | | | | n.d. | <5 | <5 | | 43 | n.d. |
| Compound 4 | | | | | n.d. | <5 | <5 | | 86 | n.d. |
| Compound 5 | | | <5 | 80 | n.d. | 128 | 131 | n.d. | | |
| Compound 6 | <5 | <5 | 49 | 47 | n.d. | 131 | 89 | n.d. | | |
| Compound 7 | | n.d. | <5 | 14 | 55 | n.d. | 129 | n.d. | | |
| Compound 8 | | n.d. | <5 | 70 | 117 | n.d. | 130 | n.d. | | |
| Compound 9 | n.d. | <5 | 47 | 82 | n.d. | n.d. | 126 | n.d. | | |
| Compound 10 | | n.d. | <5 | <5 | 6 | n.d. | 118 | n.d. | | |
| Compound 11 | <5 | 34 | 95 | 116 | n.d. | | | | | |
| Example 1 | | | | n.d. | <5 | 53 | 96 | n.d. | | |
| Example 2 | | n.d. | <5 | <5 | <5 | 55 | 93 | n.d. | | |
| Example 3 | | | | | n.d. | <5 | <5 | <5 | <5 | |
| Example 4 | | | | | n.d. | <5 | <5 | <5 | <5 | |
| Example 5 | | n.d. | <5 | <5 | 66 | 84 | 124 | n.d. | | |
| Example 6 | | n.d. | <5 | <5 | <5 | 91 | 110 | n.d. | | |
| Example 7 | | n.d. | <5 | n.d. | <5 | <5 | 68 | n.d. | | |
| Example 35 | | n.d. | <5 | <5 | 86 | n.d. | 108 | n.d. | | |
| Example 41 | | n.d. | <5 | 10 | 56 | n.d. | 120 | n.d. | | |
| Example 45 | | | | | n.d. | <5 | <5 | | 52 | n.d. |
| Example 50 | | n.d. | <5 | 55 | 103 | n.d. | | | | |
| Example 54 | | | n.d. | <5 | 5.6 | 55 | 76 | n.d. | | | n.d. = not determined.
For experimental details and further data see Example 69.

The compounds of the present invention can be utilized alone or in combination with standard drugs inhibiting T-cell activation, to provide a new immunomodulating therapy with a reduced propensity for infections when compared to standard immunosuppressive therapy. Furthermore, the compounds of the present invention can be used in combination with reduced dosages of traditional immunosuppressant therapies, to provide on the one hand effective immunomodulating activity, while on the other hand reducing end organ damage associated with higher doses of standard immunosuppressive drugs. The observation of improved endothelial cell layer function associated with S1P1/EDG1 activation provides additional benefits of compounds to improve vascular function.

The nucleotide sequence and the amino acid sequence for the human S1P1/EDG1 receptor are known in the art and are published in e.g.: Hla, T., and Maciag, T., J. Biol. Chem. 265 (1990), 9308-9313; WO 91/15583 published 17 Oct. 1991; WO 99/46277 published 16 Sep. 1999. The potency and efficacy of the compounds of Formula (I) are assessed using a GTPγS assay to determine $EC_{50}$ values and by measuring the circulating lymphocytes in the rat after oral administration, respectively (see in experimental part).

i) In a first embodiment, the invention relates to pyridine compounds of the Formula (I),

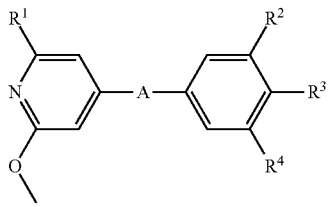

Formula (I)

wherein
A represents

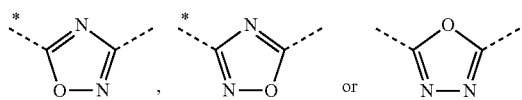

wherein the asterisks indicate the bond that is linked to the pyridine group of Formula (I);

$R^1$ represents cyclopentyl;
$R^2$ represents methyl, and $R^4$ represents ethyl or chloro; or $R^2$ represents methoxy, and $R^4$ represents chloro;
$R^3$ represents —OCH$_2$COOH, —OCH$_2$CH$_2$CH$_2$COOH, —OCH$_2$CONHCH$_2$CH$_2$OH, —OCH$_2$CH$_2$CH$_2$CONHCH$_2$CH$_2$OH, —OCH$_2$—(CH$_2$)$_n$—NH—(CH$_2$)$_m$—COOH, —OCH$_2$—(CH$_2$)$_n$—N(CH$_3$)—(CH$_2$)$_m$—COOH, 2-[(azetidine-3-carboxylic acid)-1-yl]-ethoxy, 2-[(pyrrolidin-3-carboxylic acid)-1-yl]-ethoxy, 3-[(azetidine-3-carboxylic acid)-1-yl]-propoxy, 3-[(pyrrolidin-3-carboxylic acid)-1-yl]-propoxy, —OCH$_2$CH(OH)—CH$_2$NH—CH$_2$COOH, —OCH$_2$CH(OH)—CH$_2$NH—CH$_2$CH$_2$COOH, —OCH$_2$CH(OH)—CH$_2$N(CH$_3$)—CH$_2$COOH, —OCH$_2$CH(OH)—CH$_2$N(CH$_3$)—CH$_2$CH$_2$COOH, 3-[(azetidine-3-carboxylic acid)-1-yl]-2-hydroxy-propoxy, 2-hydroxy-3-[(pyrrolidin-3-carboxylic acid)-1-yl]-propoxy, —OCH$_2$—(CH$_2$)$_n$—NH—CH$_2$CH$_2$OH, —OCH$_2$—(CH$_2$)$_n$—NH—CH(CH$_2$OH)$_2$, —OCH$_2$—(CH$_2$)$_n$—NH—CH$_2$CH(OH)—CH$_2$OH, —OCH$_2$CH(OH)—CH$_2$NH—CH$_2$CH$_2$OH, —OCH$_2$CH(OH)—CH$_2$NH—CH(CH$_2$OH)$_2$, —OCH$_2$—(CH$_2$)$_k$—NH—CO—CH$_2$OH, —OCH$_2$—(CH$_2$)$_n$—NH—CO—CH$_2$COOH, —OCH$_2$—(CH$_2$)$_n$—NH—CO—CH$_2$CH$_2$COOH, —OCH$_2$CH(OH)—CH$_2$NH—CO—(CH$_2$)$_n$COOH, —OCH$_2$—(CH$_2$)$_n$—N(CH$_3$)—CO—CH$_2$OH, —OCH$_2$—(CH$_2$)$_n$—N(CH$_3$)—CO—CH$_2$COOH, or —OCH$_2$—(CH$_2$)$_n$—N(CH$_3$)—CO—CH$_2$CH$_2$COOH;
n independently represents 1 or 2;
m independently represents 1, 2, or 3; and
k represents 1 or 2, such as especially 2.

ii) Another embodiment of the invention relates to pyridine derivatives according to the embodiment i), wherein the stereocenter of the $R^3$ groups 2-[(pyrrolidin-3-carboxylic acid)-1-yl]-ethoxy, 3-[(pyrrolidin-3-carboxylic acid)-1-yl]-propoxy, —O—CH$_2$CH(OH)—CH$_2$NH—CH$_2$COOH, —OCH$_2$CH(OH)—CH$_2$NH—CH$_2$CH$_2$COOH, —OCH$_2$CH(OH)—CH$_2$N(CH$_3$)—CH$_2$COOH, —OCH$_2$CH(OH)—CH$_2$N(CH$_3$)—CH$_2$CH$_2$COOH, 3-[(azetidine-3-carboxylic acid)-1-yl]-2-hydroxy-propoxy, —OCH$_2$—(CH$_2$)$_n$—NH—CH$_2$CH(OH)—CH$_2$OH, —OCH$_2$CH(OH)—CH$_2$NH—CH$_2$CH$_2$OH, —OCH$_2$CH(OH)—CH$_2$NH—CH(CH$_2$OH)$_2$, and —OCH$_2$CH(OH)—CH$_2$NH—CO—(CH$_2$)$_n$COOH is in the S-configuration.

iii) Another embodiment of the invention relates to pyridine derivatives according to the embodiment i), wherein the stereocenter of the $R^3$ groups 2-[(pyrrolidin-3-carboxylic acid)-1-yl]-ethoxy, 3-[(pyrrolidin-3-carboxylic acid)-1-yl]-propoxy, —O—CH$_2$CH(OH)—CH$_2$NH—CH$_2$COOH, —OCH$_2$CH(OH)—CH$_2$NH—CH$_2$CH$_2$COOH, —OCH$_2$CH(OH)—CH$_2$N(CH$_3$)—CH$_2$COOH, —OCH$_2$CH(OH)—CH$_2$N(CH$_3$)—CH$_2$CH$_2$COOH, 3-[(azetidine-3-carboxylic acid)-1-yl]-2-hydroxy-propoxy, —OCH$_2$—(CH$_2$)$_n$—NH—CH$_2$CH(OH)—CH$_2$OH, —OCH$_2$CH(OH)—CH$_2$NH—CH$_2$CH$_2$OH, —OCH$_2$CH(OH)—CH$_2$NH—CH(CH$_2$OH)$_2$, and —OCH$_2$CH(OH)—CH$_2$NH—CO—(CH$_2$)$_n$COOH is in the R-configuration.

iv) Another embodiment of the invention relates to pyridine derivatives according to any one of the embodiments i) to iii), wherein A represents

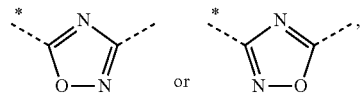

wherein the asterisks indicate the bond that is linked to the pyridine group of Formula (I).

v) Another embodiment of the invention relates to pyridine derivatives according to any one of the embodiments i) to iii), wherein A represents

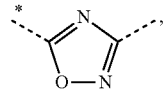

wherein the asterisk indicates the bond that is linked to the pyridine group of Formula (I).

vi) Another embodiment of the invention relates to pyridine derivatives according to any one of the embodiments i) to iii), wherein A represents

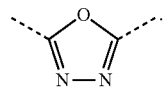

vii) Another embodiment of the invention relates to pyridine derivatives according to any one of the embodiments i) to vi), wherein $R^2$ represents methyl, and $R^4$ represents ethyl or chloro.

viii) Another embodiment of the invention relates to pyridine derivatives according to any one of the embodiments i) to vi), wherein $R^2$ represents methyl, and $R^4$ represents ethyl.

ix) Another embodiment of the invention relates to pyridine derivatives according to any one of the embodiments i) to vi), wherein $R^2$ represents methoxy, and $R^4$ represents chloro.

x) Another embodiment of the invention relates to pyridine derivatives according to any one of the embodiments i) to ix), wherein $R^3$ represents —OCH$_2$COOH, —OCH$_2$CH$_2$CH$_2$COOH, —OCH$_2$CONHCH$_2$CH$_2$OH, —OCH$_2$CH$_2$CH$_2$CONHCH$_2$CH$_2$OH, —OCH$_2$—(CH$_2$)$_n$—NH—(CH$_2$)$_m$—COOH, —OCH$_2$—(CH$_2$)$_n$—N(CH$_3$)—(CH$_2$)$_m$—COOH, 2-[(azetidine-3-carboxylic acid)-1-yl]- ethoxy, 2-[(pyrrolidin-3-carboxylic acid)-1-yl]-ethoxy, 3-[(azetidine-3-carboxylic acid)-1-yl]propoxy, —OCH$_2$CH(OH)—CH$_2$NH—CH$_2$COOH, —OCH$_2$CH(OH)—CH$_2$NH—CH$_2$CH$_2$COOH, —OCH$_2$CH(OH)—CH$_2$N(CH$_3$)—CH$_2$COOH, 3-[(azetidine-3-carboxylic acid)-1-yl]-2-hydroxy-propoxy, —OCH$_2$—(CH$_2$)$_n$—NH—CH$_2$CH$_2$OH, —OCH$_2$—(CH$_2$)$_n$—NH—CH(CH$_2$OH)$_2$, —OCH$_2$—(CH$_2$)$_n$—NH—CH$_2$CH(OH)—CH$_2$OH, —OCH$_2$CH(OH)—CH$_2$NH—CH$_2$CH$_2$OH, —OCH$_2$CH(OH)—CH$_2$NH—CH(CH$_2$OH)$_2$, —OCH$_2$—(CH$_2$)$_k$—NH—CO—CH$_2$OH, —OCH$_2$—(CH$_2$)$_n$—NH—CO—CH$_2$COOH, —OCH$_2$—(CH$_2$)$_n$—NH—CO—CH$_2$CH$_2$COOH, —OCH$_2$CH(OH)—CH$_2$NH—CO—(CH$_2$)$_n$COOH, —OCH$_2$—(CH$_2$)$_n$—N(CH$_3$)—CO—CH$_2$OH, —OCH$_2$—(CH$_2$)$_n$—N(CH$_3$)—CO—CH$_2$COOH, or —OCH$_2$—(CH$_2$)$_n$—N(CH$_3$)—CO—CH$_2$CH$_2$COOH.

xi) Another embodiment of the invention relates to pyridine derivatives according to any one of the embodiments i) to ix), wherein R$^3$ represents —OCH$_2$COOH, —OCH$_2$CH$_2$CH$_2$COOH, —OCH$_2$CONHCH$_2$CH$_2$OH, —OCH$_2$CH$_2$CH$_2$CONHCH$_2$CH$_2$OH, —OCH$_2$—(CH$_2$)$_n$—NH—(CH$_2$)$_m$—COOH, —OCH$_2$—(CH$_2$)$_n$—N(CH$_3$)—(CH$_2$)$_m$—COOH, 2-[(azetidine-3-carboxylic acid)-1-yl]-ethoxy, 2-[(pyrrolidin-3-carboxylic acid)-1-yl]-ethoxy, 3-[(azetidine-3-carboxylic acid)-1-yl]-propoxy, 3-[(pyrrolidin-3-carboxylic acid)-1-yl]propoxy, —O—CH$_2$CH(OH)—CH$_2$NH—CH$_2$COOH, —OCH$_2$CH(OH)—CH$_2$NH—CH$_2$CH$_2$COOH, —OCH$_2$CH(OH)—CH$_2$N(CH$_3$)—CH$_2$COOH, —OCH$_2$CH(OH)—CH$_2$N(CH$_3$)—CH$_2$CH$_2$COOH, 3-[(azetidine-3-carboxylic acid)-1-yl]-2-hydroxy-propoxy, 2-hydroxy-3-[(pyrrolidin-3-carboxylic acid)-1-yl]propoxy, —OCH$_2$—(CH$_2$)$_n$—NH—CH$_2$CH$_2$OH, —OCH$_2$—(CH$_2$)$_n$—NH—CH(CH$_2$OH)$_2$, —OCH$_2$—(CH$_2$)$_n$—NH—CH$_2$CH(OH)—CH$_2$OH, —OCH$_2$CH(OH)—CH$_2$NH—CH$_2$CH$_2$OH, —O—CH$_2$CH(OH)—CH$_2$NH—CH(CH$_2$OH)$_2$, —OCH$_2$—(CH$_2$)$_k$—NH—CO—CH$_2$OH, or —OCH$_2$—(CH$_2$)$_n$—N(CH$_3$)—CO—CH$_2$OH.

xii) Another embodiment of the invention relates to pyridine derivatives according to any one of the embodiments i) to ix), wherein R$^3$ represents —OCH$_2$COOH, —OCH$_2$CH$_2$CH$_2$COOH, —OCH$_2$CONHCH$_2$CH$_2$OH, —OCH$_2$CH$_2$CH$_2$CONHCH$_2$CH$_2$OH, —OCH$_2$—(CH$_2$)$_n$—NH—(CH$_2$)$_m$—COOH, —OCH$_2$—(CH$_2$)$_n$—N(CH$_3$)—(CH$_2$)$_m$—COOH, 2-[(azetidine-3-carboxylic acid)-1-yl]-ethoxy, 2-[(pyrrolidin-3-carboxylic acid)-1-yl]-ethoxy, 3-[(azetidine-3-carboxylic acid)-1-yl]-propoxy, 3-[(pyrrolidin-3-carboxylic acid)-1-yl]propoxy, —OCH$_2$CH(OH)—CH$_2$N(CH$_3$)—CH$_2$COOH, —OCH$_2$CH(OH)—CH$_2$N(CH$_3$)—CH$_2$CH$_2$COOH, 3-[(azetidine-3-carboxylic acid)-1-yl]-2-hydroxy-propoxy, 2-hydroxy-3-[(pyrrolidin-3-carboxylic acid)-1-yl]-propoxy, —OCH$_2$—(CH$_2$)$_n$—NH—CH$_2$CH$_2$OH, —OCH$_2$—(CH$_2$)$_n$—NH—CH(CH$_2$OH)$_2$, —OCH$_2$CH(OH)—CH$_2$NH—CH$_2$CH$_2$OH, —O—CH$_2$CH(OH)—CH$_2$NH—CH(CH$_2$OH)$_2$, —OCH$_2$—(CH$_2$)$_n$—NH—CO—CH$_2$COOH, —OCH$_2$—(CH$_2$)$_n$—NH—CO—CH$_2$CH$_2$COOH, —O—CH$_2$CH(OH)—CH$_2$NH—CO—(CH$_2$)$_n$COOH, —OCH$_2$—(CH$_2$)$_n$—N(CH$_3$)—CO—CH$_2$COOH, or —OCH$_2$—(CH$_2$)$_n$—N(CH$_3$)—CO—CH$_2$CH$_2$COOH.

xiii) Another embodiment of the invention relates to pyridine derivatives according to any one of the embodiments i) to ix), wherein R$^3$ represents —OCH$_2$COOH, —OCH$_2$CH$_2$CH$_2$COOH, —OCH$_2$CONHCH$_2$CH$_2$OH, —OCH$_2$CH$_2$CH$_2$CONHCH$_2$CH$_2$OH, —OCH$_2$—(CH$_2$)$_n$—NH—(CH$_2$)$_m$—COOH, —OCH$_2$—(CH$_2$)$_n$—N(CH$_3$)—(CH$_2$)$_m$—COOH, 2-[(azetidine-3-carboxylic acid)-1-yl]-ethoxy, 3-[(azetidine-3-carboxylic acid)-1-yl]propoxy, —OCH$_2$CH(OH)—CH$_2$N(CH$_3$)—CH$_2$COOH, —OCH$_2$CH(OH)—CH$_2$N(CH$_3$)—CH$_2$CH$_2$COOH, 3-[(azetidine-3-carboxylic acid)-1-yl]-2-hydroxy-propoxy, —OCH$_2$—(CH$_2$)$_n$—NH—CH$_2$CH$_2$OH, —OCH$_2$—(CH$_2$)$_n$—NH—CH(CH$_2$OH)$_2$, —O—CH$_2$CH(OH)—CH$_2$NH—CH$_2$CH$_2$OH, —OCH$_2$CH(OH)—CH$_2$NH—CH(CH$_2$OH)$_2$, —OCH$_2$—(CH$_2$)$_k$—NH—CO—CH$_2$OH, —OCH$_2$—(CH$_2$)$_n$—NH—CO—CH$_2$COOH, —OCH$_2$—(CH$_2$)$_n$—NH—CO—CH$_2$CH$_2$COOH, —OCH$_2$CH(OH)—CH$_2$NH—CO—(CH$_2$)$_n$COOH, —OCH$_2$—(CH$_2$)$_n$—N(CH$_3$)—CO—CH$_2$COOH, or —OCH$_2$—(CH$_2$)$_n$—N(CH$_3$)—CO—CH$_2$CH$_2$COOH.

xiv) Another embodiment of the invention relates to pyridine derivatives according to any one of the embodiments i) to ix), wherein R$^3$ represents —OCH$_2$COOH, —OCH$_2$CH$_2$CH$_2$COOH, —OCH$_2$—(CH$_2$)$_n$—NH—(CH$_2$)$_m$—COOH, —OCH$_2$—(CH$_2$)$_n$—N(CH$_3$)—(CH$_2$)$_m$—COOH, 2-[(azetidine-3-carboxylic acid)-1-yl]-ethoxy, 3-[(azetidine-3-carboxylic acid)-1-yl]-propoxy, or 3-[(azetidine-3-carboxylic acid)-1-yl]-2-hydroxy-propoxy.

xv) Another embodiment of the invention relates to pyridine derivatives according to any one of the embodiments i) to ix), wherein R$^3$ represents —OCH$_2$CONHCH$_2$CH$_2$OH, —OCH$_2$CH$_2$CH$_2$CONHCH$_2$CH$_2$OH, —OCH$_2$CH(OH)—CH$_2$N(CH$_3$)—CH$_2$COOH, —OCH$_2$CH(OH)—CH$_2$N(CH$_3$)—CH$_2$CH$_2$COOH, 3-[(azetidine-3-carboxylic acid)-1-yl]-2-hydroxy-propoxy, —OCH$_2$—(CH$_2$)$_n$—NH—CH$_2$CH$_2$OH, —OCH$_2$—(CH$_2$)$_n$—NH—CH(CH$_2$OH)$_2$, —O—CH$_2$CH(OH)—CH$_2$NH—CH$_2$CH$_2$OH, or —O—CH$_2$CH(OH)—CH$_2$NH—CH(CH$_2$OH)$_2$.

xvi) Another embodiment of the invention relates to pyridine derivatives according to any one of the embodiments i) to xiv), wherein m represents 1 or 2.

xvii) Another embodiment of the invention relates to pyridine derivatives according to any one of the embodiments i) to xvi), wherein n represents 1.

xviii) Another embodiment of the invention relates to pyridine derivatives according to the embodiment i), wherein A represents

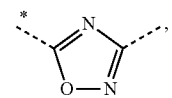

wherein the asterisk indicates the bond that is linked to the pyridine group of Formula (I);

R$^1$ represents cyclopentyl;

R$^2$ represents methyl, and R$^4$ represents ethyl or chloro; or R$^2$ represents methoxy, and R$^4$ represents chloro; and R$^3$ represents —OCH$_2$COOH, —OCH$_2$CH$_2$CH$_2$COOH, —OCH$_2$CONHCH$_2$CH$_2$OH, —OCH$_2$CH$_2$CH$_2$CONHCH$_2$CH$_2$OH, —OCH$_2$—(CH$_2$)$_{1-2}$—NH—(CH$_2$)$_{1-2}$—COOH, —OCH$_2$—CH$_2$—NH—(CH$_2$)$_3$—COOH, —OCH$_2$—(CH$_2$)$_{1-2}$—N(CH$_3$)—(CH$_2$)$_{1-2}$—COOH, 2-[(azetidine-3-carboxylic acid)-1-yl]-ethoxy, 2-[(pyrrolidin-3-carboxylic acid)-1-yl]-ethoxy, 3-[(azetidine-3-carboxylic acid)-1-yl]-propoxy, —OCH$_2$CH(OH)—CH$_2$NH—CH$_2$COOH, —OCH$_2$CH(OH)—CH$_2$NH—CH$_2$CH$_2$COOH, —OCH$_2$CH(OH)—CH$_2$N(CH$_3$)—CH$_2$COOH, 3-[(azetidine-3-carboxylic acid)-1-yl]-2-hydroxy-propoxy, —OCH$_2$—(CH$_2$)$_{1-2}$—NH—CH$_2$CH$_2$OH, —OCH$_2$—(CH$_2$)$_{1-2}$—NH—CH(CH$_2$OH)$_2$, —OCH$_2$—(CH$_2$)$_{1-2}$—NH—CH$_2$CH(OH)—CH$_2$OH, —OCH$_2$CH(OH)—CH$_2$NH—CH$_2$CH$_2$OH, —OCH$_2$CH(OH)—CH$_2$NH—CH(CH$_2$OH)$_2$, —OCH$_2$—(CH$_2$)$_2$—NH—CO—CH$_2$OH, —OCH$_2$—(CH$_2$)$_2$—NH—CO—

CH₂COOH, —OCH₂—(CH₂)₂—NH—CO—CH₂CH₂COOH, —OCH₂CH(OH)—CH₂NH—CO—(CH₂)₁₋₂COOH, —OCH₂—(CH₂)₂—N(CH₃)—CO—CH₂OH, —OCH₂—(CH₂)₂—N(CH₃)—CO—CH₂COOH, or —OCH₂—(CH₂)₂—N(CH₃)—CO—CH₂CH₂COOH.

xix) Another embodiment of the invention relates to pyridine derivatives according to the embodiment i), wherein R³ represents —OCH₂COOH, —OCH₂CH₂CH₂COOH, —OCH₂CONHCH₂CH₂OH, —OCH₂CH₂CH₂CONHCH₂CH₂OH, —OCH₂—(CH₂)₁₋₂—NH—(CH₂)₁₋₂—COOH, —OCH₂—CH₂—NH—(CH₂)₃—COOH, —OCH₂—(CH₂)₁₋₂—N(CH₃)—(CH₂)₁₋₂—COOH, 2-[(azetidine-3-carboxylic acid)-1-yl]-ethoxy, 2-[(pyrrolidin-3-carboxylic acid)-1-yl]-ethoxy, 3-[(azetidine-3-carboxylic acid)-1-yl]-propoxy, —OCH₂CH(OH)—CH₂NH—CH₂COOH, —OCH₂CH(OH)—CH₂NH—CH₂CH₂COOH, —OCH₂CH(OH)—CH₂N(CH₃)—CH₂COOH, —OCH₂CH(OH)—CH₂N(CH₃)—CH₂CH₂COOH, 3-[(azetidine-3-carboxylic acid)-1-yl]-2-hydroxy-propoxy, —OCH₂—(CH₂)₁₋₂—NH—CH₂CH₂OH, —OCH₂—(CH₂)₁₋₂—NH—CH(CH₂OH)₂, —OCH₂—(CH₂)₁₋₂—NH—CH₂CH(OH)—CH₂OH, —OCH₂CH(OH)—CH₂NH—CH₂CH₂OH, —OCH₂CH(OH)—CH₂NH—CH(CH₂OH)₂, —OCH₂—(CH₂)₂—NH—CO—CH₂OH, —OCH₂—(CH₂)₁₋₂—NH—CO—CH₂COOH, —OCH₂—(CH₂)₁₋₂—NH—CO—CH₂CH₂COOH, —OCH₂CH(OH)—CH₂NH—CO—(CH₂)₁₋₂COOH, —OCH₂—(CH₂)₂—N(CH₃)—CO—CH₂OH, —OCH₂—(CH₂)₂—N(CH₃)—CO—CH₂COOH, or —OCH₂—(CH₂)₂—N(CH₃)—CO—CH₂CH₂COOH.

The compounds of Formula (I) may contain one or more stereogenic or asymmetric centers, such as one or more asymmetric carbon atoms. The compounds of Formula (I) may thus be present as mixtures of stereoisomers or preferably as pure stereoisomers. Mixtures of stereoisomers may be separated in a manner known to a person skilled in the art.

Where the plural form is used for compounds, salts, pharmaceutical compositions, diseases and the like, this is intended to mean also a single compound, salt, or the like.

Any reference hereinbefore or hereinafter to a compound of Formula (I) is to be understood as referring also to salts, especially pharmaceutically acceptable salts, of a compound of Formula (I), as appropriate and expedient.

The term "pharmaceutically acceptable salts" refers to non-toxic, inorganic or organic acid and/or base addition salts. Reference can be made to "Salt selection for basic drugs", *Int. J. Pharm.* (1986), 33, 201-217.

The present invention also includes isotopically labelled, especially ²H (deuterium) labelled compounds of Formula (I), which compounds are identical to the compounds of Formula (I) except that one or more atoms have each been replaced by an atom having the same atomic number but an atomic mass different from the atomic mass usually found in nature. Isotopically labelled, especially ²H (deuterium) labelled compounds of Formula (I) and salts thereof are within the scope of the present invention. Substitution of hydrogen with the heavier isotope ²H (deuterium) may lead to greater metabolic stability, resulting e.g. in increased in vivo half-life or reduced dosage requirements, or may lead to reduced inhibition of cytochrome P450 enzymes, resulting e.g. in an improved safety profile. In one embodiment of the invention, the compounds of Formula (I) are not isotopically labelled, or they are labelled only with one or more deuterium atoms. In a sub-embodiment, the compounds of Formula (I) are not isotopically labelled at all. Isotopically labelled compounds of Formula (I) may be prepared in analogy to the methods described hereinafter, but using the appropriate isotopic variation of suitable reagents or starting materials.

Examples of pyridine compounds according to Formula (I) are selected from:

3-(2-{4-[5-(2-cyclopentyl-6-methoxy-pyridin-4-yl)-[1,2,4]oxadiazol-3-yl]-2-ethyl-6-methyl-phenoxy}-ethylamino)-propionic acid, 1-(2-{4-[5-(2-cyclopentyl-6-methoxy-pyridin-4-yl)-[1,2,4]oxadiazol-3-yl]-2-ethyl-6-methyl-phenoxy}-ethyl)-azetidine-3-carboxylic acid, (S)-1-{4-[5-(2-cyclopentyl-6-methoxy-pyridin-4-yl)-[1,2,4]oxadiazol-3-yl]-2-ethyl-6-methyl-phenoxy}-3-(2-hydroxy-ethylamino)-propan-2-ol, 2-((S)-3-{4-[5-(2-cyclopentyl-6-methoxy-pyridin-4-yl)-[1,2,4]oxadiazol-3-yl]-2-ethyl-6-methyl-phenoxy}-2-hydroxy-propylamino)-propane-1,3-diol, {4-[5-(2-cyclopentyl-6-methoxy-pyridin-4-yl)-[1,2,4]oxadiazol-3-yl]-2-ethyl-6-methyl-phenoxy}-acetic acid, 4-{4-[5-(2-cyclopentyl-6-methoxy-pyridin-4-yl)-[1,2,4]oxadiazol-3-yl]-2-ethyl-6-methyl-phenoxy}-butyric acid, (2-{4-[5-(2-cyclopentyl-6-methoxy-pyridin-4-yl)-[1,2,4]oxadiazol-3-yl]-2-ethyl-6-methyl-phenoxy}-ethylamino)acetic acid, 1-(2-{4-[5-(2-cyclopentyl-6-methoxy-pyridin-4-yl)-[1,2,4]oxadiazol-3-yl]-2-ethyl-6-methyl-phenoxy}-ethyl)-pyrrolidine-3-carboxylic acid, ((S)-3-{4-[5-(2-cyclopentyl-6-methoxy-pyridin-4-yl)-[1,2,4]oxadiazol-3-yl]-2-ethyl-6-methyl-phenoxy}-2-hydroxy-propylamino)-acetic acid, 3-((S)-3-{4-[5-(2-cyclopentyl-6-methoxy-pyridin-4-yl)-[1,2,4]oxadiazol-3-yl]-2-ethyl-6-methyl-phenoxy}-2-hydroxy-propylamino)-propionic acid,

[((S)-3-{4-[5-(2-cyclopentyl-6-methoxy-pyridin-4-yl)-[1,2,4]oxadiazol-3-yl]-2-ethyl-6-methyl-phenoxy}-2-hydroxy-propyl)-methyl-amino]-acetic acid, 1-((S)-3-{4-[5-(2-cyclopentyl-6-methoxy-pyridin-4-yl)-[1,2,4]oxadiazol-3-yl]-2-ethyl-6-methyl-phenoxy}-2-hydroxy-propyl)-azetidine-3-carboxylic acid, 2-{4-[5-(2-cyclopentyl-6-methoxy-pyridin-4-yl)-[1,2,4]oxadiazol-3-yl]-2-ethyl-6-methyl-phenoxy}-N-(2-hydroxy-ethyl)-acetamide, N—((S)-3-{4-[5-(2-cyclopentyl-6-methoxy-pyridin-4-yl)-[1,2,4]oxadiazol-3-yl]-2-ethyl-6-methyl-phenoxy}-2-hydroxy-propyl)-malonamic acid, N—((S)-3-{4-[5-(2-cyclopentyl-6-methoxy-pyridin-4-yl)-[1,2,4]oxadiazol-3-yl]-2-ethyl-6-methyl-phenoxy}-2-hydroxy-propyl)-succinamic acid,

[(2-{4-[5-(2-cyclopentyl-6-methoxy-pyridin-4-yl)-[1,2,4]oxadiazol-3-yl]-2-ethyl-6-methyl-phenoxy}-ethyl)-methyl-amino]-acetic acid, 3-[(2-{4-[5-(2-cyclopentyl-6-methoxy-pyridin-4-yl)-[1,2,4]oxadiazol-3-yl]-2-ethyl-6-methyl-phenoxy}-ethyl)-methyl-amino]-propionic acid, (3-{4-[5-(2-cyclopentyl-6-methoxy-pyridin-4-yl)-[1,2,4]oxadiazol-3-yl]-2-ethyl-6-methyl-phenoxy}-propylamino)-acetic acid, 3-(3-{4-[5-(2-cyclopentyl-6-methoxy-pyridin-4-yl)-[1,2,4]oxadiazol-3-yl]-2-ethyl-6-methyl-phenoxy}-propylamino)-propionic acid,

[(3-{4-[5-(2-cyclopentyl-6-methoxy-pyridin-4-yl)-[1,2,4]oxadiazol-3-yl]-2-ethyl-6-methyl-phenoxy}-propyl)-methyl-amino]-acetic acid, 3-[(3-{4-[5-(2-cyclopentyl-6-methoxy-pyridin-4-yl)-[1,2,4]oxadiazol-3-yl]-2-ethyl-6-methyl-phenoxy}-propyl)-methyl-amino]-propionic acid, 1-(3-{4-[5-(2-cyclopentyl-6-methoxy-pyridin-4-yl)-[1,2,4]oxadiazol-3-yl]-2-ethyl-6-methyl-phenoxy}-propyl)-azetidine-3-carboxylic acid,
2-(2-{4-[5-(2-cyclopentyl-6-methoxy-pyridin-4-yl)-[1,2,4]oxadiazol-3-yl]-2-ethyl-6-methyl-phenoxy}-ethylamino)-ethanol,
2-(3-{4-[5-(2-cyclopentyl-6-methoxy-pyridin-4-yl)-[1,2,4]oxadiazol-3-yl]-2-ethyl-6-methyl-phenoxy}-propylamino)-ethanol,
2-(2-{4-[5-(2-cyclopentyl-6-methoxy-pyridin-4-yl)-[1,2,4]oxadiazol-3-yl]-2-ethyl-6-methyl-phenoxy}-ethylamino)-propane-1,3-diol,
2-(3-{4-[5-(2-cyclopentyl-6-methoxy-pyridin-4-yl)-[1,2,4]oxadiazol-3-yl]-2-ethyl-6-methyl-phenoxy}-propylamino)-propane-1,3-diol,
3-(2-{4-[5-(2-cyclopentyl-6-methoxy-pyridin-4-yl)-[1,2,4]oxadiazol-3-yl]-2-ethyl-6-methyl-phenoxy}-ethylamino)-propane-1,2-diol,
3-(3-{4-[5-(2-cyclopentyl-6-methoxy-pyridin-4-yl)-[1,2,4]oxadiazol-3-yl]-2-ethyl-6-methyl-phenoxy}-propylamino)-propane-1,2-diol,
N-(3-{4-[5-(2-cyclopentyl-6-methoxy-pyridin-4-yl)-[1,2,4]oxadiazol-3-yl]-2-ethyl-6-methyl-phenoxy}-propyl)-2-hydroxy-acetamide,
N-(3-{4-[5-(2-cyclopentyl-6-methoxy-pyridin-4-yl)-[1,2,4]oxadiazol-3-yl]-2-ethyl-6-methyl-phenoxy}-propyl)-2-hydroxy-N-methyl-acetamide,
N-(3-{4-[5-(2-cyclopentyl-6-methoxy-pyridin-4-yl)-[1,2,4]oxadiazol-3-yl]-2-ethyl-6-methyl-phenoxy}-propyl)-malonamic acid,
N-(3-{4-[5-(2-cyclopentyl-6-methoxy-pyridin-4-yl)-[1,2,4]oxadiazol-3-yl]-2-ethyl-6-methyl-phenoxy}-propyl)-succinamic acid,
N-(3-{4-[5-(2-cyclopentyl-6-methoxy-pyridin-4-yl)-[1,2,4]oxadiazol-3-yl]-2-ethyl-6-methyl-phenoxy}-propyl)-N-methyl-malonamic acid,
N-(3-{4-[5-(2-cyclopentyl-6-methoxy-pyridin-4-yl)-[1,2,4]oxadiazol-3-yl]-2-ethyl-6-methyl-phenoxy}-propyl)-N-methyl-succinamic acid,
4-{2-chloro-4-[5-(2-cyclopentyl-6-methoxy-pyridin-4-yl)-[1,2,4]oxadiazol-3-yl]-6-methoxy-phenoxy}-butyric acid,
4-{2-chloro-4-[5-(2-cyclopentyl-6-methoxy-pyridin-4-yl)-[1,2,4]oxadiazol-3-yl]-6-methoxy-phenoxy}-N-(2-hydroxy-ethyl)-butyramide,
3-(2-{2-chloro-4-[5-(2-cyclopentyl-6-methoxy-pyridin-4-yl)-[1,2,4]oxadiazol-3-yl]-6-methoxy-phenoxy}-ethylamino)-propionic acid,
N-(3-{2-chloro-4-[5-(2-cyclopentyl-6-methoxy-pyridin-4-yl)-[1,2,4]oxadiazol-3-yl]-6-methoxy-phenoxy}-propyl)-2-hydroxy-acetamide,
4-((2-(4-(5-(2-cyclopentyl-6-methoxypyridin-4-yl)-1,2,4-oxadiazol-3-yl)-2-ethyl-6-methylphenoxy)ethyl)amino)butanoic acid, and
4-(2-chloro-4-(5-(2-cyclopentyl-6-methoxypyridin-4-yl)-1,2,4-oxadiazol-3-yl)-6-methylphenoxy)butanoic acid.

Additional Examples of pyridine compounds according to Formula (I) are selected from:
2-(2-chloro-4-(5-(2-cyclopentyl-6-methoxypyridin-4-yl)-1,2,4-oxadiazol-3-yl)-6-methylphenoxy)acetic acid,
2-(2-chloro-4-(5-(2-cyclopentyl-6-methoxypyridin-4-yl)-1,2,4-oxadiazol-3-yl)-6-methyl-phenoxy)-N-(2-hydroxy-ethyl)acetamide,
3-((2-(2-chloro-4-(5-(2-cyclopentyl-6-methoxypyridin-4-yl)-1,2,4-oxadiazol-3-yl)-6-methylphenoxy)ethyl)amino)propanoic acid,
1-(2-(2-chloro-4-(5-(2-cyclopentyl-6-methoxypyridin-4-yl)-1,2,4-oxadiazol-3-yl)-6-methylphenoxy)ethyl)azetidine-3-carboxylic acid,
2-((2-(2-chloro-4-(5-(2-cyclopentyl-6-methoxypyridin-4-yl)-1,2,4-oxadiazol-3-yl)-6-methylphenoxy)ethyl)amino)ethanol,
4-(4-(5-(2-cyclopentyl-6-methoxypyridin-4-yl)-1,2,4-oxadiazol-3-yl)-2-ethyl-6-methylphenoxy)-N-(2-hydroxyethyl)butanamide,
(S)-3-((3-(4-(5-(2-cyclopentyl-6-methoxypyridin-4-yl)-1,2,4-oxadiazol-3-yl)-2-ethyl-6-methylphenoxy)-2-hydroxypropyl)(methyl)amino)propanoic acid,
(R)-3-((3-(4-(5-(2-cyclopentyl-6-methoxypyridin-4-yl)-1,2,4-oxadiazol-3-yl)-2-ethyl-6-methylphenoxy)-2-hydroxypropyl)(methyl)amino)propanoic acid,
3-((2-(4-(5-(2-cyclopentyl-6-methoxypyridin-4-yl)-1,2,4-oxadiazol-3-yl)-2-ethyl-6-methylphenoxy)ethyl)amino)-3-oxopropanoic acid,
4-((2-(4-(5-(2-cyclopentyl-6-methoxypyridin-4-yl)-1,2,4-oxadiazol-3-yl)-2-ethyl-6-methylphenoxy)ethyl)amino)-4-oxobutanoic acid,
2-((2-(2-chloro-4-(5-(2-cyclopentyl-6-methoxypyridin-4-yl)-1,2,4-oxadiazol-3-yl)-6-methoxyphenoxy)ethyl)amino)acetic acid,
1-(2-(2-chloro-4-(5-(2-cyclopentyl-6-methoxypyridin-4-yl)-1,2,4-oxadiazol-3-yl)-6-methoxyphenoxy)ethyl)azetidine-3-carboxylic acid,
2-(4-(3-(2-cyclopentyl-6-methoxypyridin-4-yl)-1,2,4-oxadiazol-5-yl)-2-ethyl-6-methylphenoxy)acetic acid,
4-(4-(3-(2-cyclopentyl-6-methoxypyridin-4-yl)-1,2,4-oxadiazol-5-yl)-2-ethyl-6-methylphenoxy)butanoic acid,
2-((2-(4-(3-(2-cyclopentyl-6-methoxypyridin-4-yl)-1,2,4-oxadiazol-5-yl)-2-ethyl-6-methylphenoxy)ethyl)amino)acetic acid,
2-((2-(4-(3-(2-cyclopentyl-6-methoxypyridin-4-yl)-1,2,4-oxadiazol-5-yl)-2-ethyl-6-methylphenoxy)ethyl)(methyl)amino)acetic acid,
3-((2-(4-(3-(2-cyclopentyl-6-methoxypyridin-4-yl)-1,2,4-oxadiazol-5-yl)-2-ethyl-6-methylphenoxy)ethyl)amino)propanoic acid,
1-(2-(4-(3-(2-cyclopentyl-6-methoxypyridin-4-yl)-1,2,4-oxadiazol-5-yl)-2-ethyl-6-methylphenoxy)ethyl)azetidine-3-carboxylic acid,
2-((3-(4-(3-(2-cyclopentyl-6-methoxypyridin-4-yl)-1,2,4-oxadiazol-5-yl)-2-ethyl-6-methylphenoxy)propyl)amino)acetic acid,
2-(4-(5-(2-cyclopentyl-6-methoxypyridin-4-yl)-1,3,4-oxadiazol-2-yl)-2-ethyl-6-methylphenoxy)acetic acid,
4-(4-(5-(2-cyclopentyl-6-methoxypyridin-4-yl)-1,3,4-oxadiazol-2-yl)-2-ethyl-6-methylphenoxy)butanoic acid,
3-((2-(4-(5-(2-cyclopentyl-6-methoxypyridin-4-yl)-1,3,4-oxadiazol-2-yl)-2-ethyl-6-methylphenoxy)ethyl)amino)propanoic acid,
1-(2-(4-(5-(2-cyclopentyl-6-methoxypyridin-4-yl)-1,3,4-oxadiazol-2-yl)-2-ethyl-6-methylphenoxy)ethyl)azetidine-3-carboxylic acid,
(S)-1-(4-(5-(2-cyclopentyl-6-methoxypyridin-4-yl)-1,3,4-oxadiazol-2-yl)-2-ethyl-6-methylphenoxy)-3-((2-hydroxyethyl)amino)propan-2-ol,
(S)-2-((3-(4-(5-(2-cyclopentyl-6-methoxypyridin-4-yl)-1,3,4-oxadiazol-2-yl)-2-ethyl-6-methylphenoxy)-2-hydroxypropyl)amino)propane-1,3-diol, and
(S)-4-((3-(4-(5-(2-cyclopentyl-6-methoxypyridin-4-yl)-1,3,4-oxadiazol-2-yl)-2-ethyl-6-methylphenoxy)-2-hydroxypropyl)amino)-4-oxobutanoic acid.

The compounds of Formula (I) and their pharmaceutically acceptable salts can be used as medicaments, e.g. in the form of pharmaceutical compositions for enteral (such as especially oral) or parenteral (including topical application or inhalation) administration, and are suitable for decreasing the number of circulating lymphocytes and for the prevention and/or treatment of diseases or disorders associated with an activated immune system.

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the described compounds of Formula (I) or their pharmaceutically acceptable salts, optionally in combination with other therapeutically valuable substances, into a galenical administration form together with suitable, non-toxic, inert, pharmaceutically acceptable solid or liquid carrier materials and, if desired, usual pharmaceutical adjuvants.

The pharmaceutical compositions comprising a compound of Formula (I) are useful for the prevention and/or treatment of diseases or disorders associated with an activated immune system.

Such diseases or disorders associated with an activated immune system and to be prevented/treated with the compounds of Formula (I) are for example selected from the group consisting of rejection of transplanted organs, tissue or cells; graft-versus-host diseases brought about by transplantation; autoimmune syndromes including rheumatoid arthritis; systemic lupus erythematosus; antiphospholipid syndrome; Hashimoto's thyroiditis; lymphocytic thyroiditis; multiple sclerosis; myasthenia gravis; type I diabetes; uveitis; episcleritis; scleritis; Kawasaki's disease, uveo-retinitis; posterior uveitis; uveitis associated with Behcet's disease; uveo-meningitis syndrome; allergic encephalomyelitis; chronic allograft vasculopathy; post-infectious autoimmune diseases including rheumatic fever and post-infectious glomerulonephritis; inflammatory and hyperproliferative skin diseases; psoriasis; psoriatic arthritis; atopic dermatitis; myopathy; myositis; osteomyelitis; contact dermatitis; eczematous dermatitis; seborrhoeic dermatitis; lichen planus; pemphigus; bullous pemphigoid; epidermolysis bullosa; urticaria; angioedema; vasculitis; erythema; cutaneous eosinophilia; acne; scleroderma; alopecia greata; keratoconjunctivitis; vernal conjunctivitis; keratitis; herpetic keratitis; dystrophia epithelialis corneae; corneal leukoma; ocular pemphigus; Mooren's ulcer; ulcerative keratitis; scleritis; Graves' ophthalmopathy; Vogt-Koyanagi-Harada syndrome; sarcoidosis; pollen allergies; reversible obstructive airway disease; bronchial asthma; allergic asthma; intrinsic asthma; extrinsic asthma; dust asthma; chronic or inveterate asthma; late asthma and airway hyper-responsiveness; bronchiolitis; bronchitis; endometriosis; orchitis; gastric ulcers; ischemic bowel diseases; inflammatory bowel diseases; necrotizing enterocolitis; intestinal lesions associated with thermal burns; coeliac disease; proctitis; eosinophilic gastroenteritis; mastocytosis; Crohn's disease; ulcerative colitis; vascular damage caused by ischemic diseases and thrombosis; atherosclerosis; fatty heart; myocarditis; cardiac infarction; aortitis syndrome; cachexia due to viral disease; vascular thrombosis; migraine; rhinitis; eczema; interstitial nephritis; IgA-induced nephropathy; Goodpasture's syndrome; hemolytic-uremic syndrome; diabetic nephropathy; glomerulosclerosis; glomerulonephritis; tubulointerstitial nephritis; interstitial cystitis; multiple myositis; Guillain-Barré syndrome; Meniere's disease; polyneuritis; multiple neuritis; myelitis; mononeuritis; radiculopathy; hyperthyroidism; Basedow's disease; thyrotoxicosis; pure red cell aplasia; aplastic anemia; hypoplastic anemia; idiopathic thrombocytopenic purpura; autoimmune hemolytic anemia; autoimmune thrombocytopenia; agranulocytosis; pernicious anemia; megaloblastic anemia; anerythroplasia; osteoporosis; fibroid lung; idiopathic interstitial pneumonia; dermatomyositis; leukoderma vulgaris; ichthyosis vulgaris; photoallergic sensitivity; cutaneous T cell lymphoma; polyarteritis nodosa; Huntington's chorea; Sydenham's chorea; myocardosis; myocarditis; scleroderma; Wegener's granuloma; Sjogren's syndrome; adiposis; eosinophilic fasciitis; lesions of gingiva, periodontium, alveolar bone, substantia ossea dentis; male pattern alopecia or alopecia senilis; muscular dystrophy; pyoderma; Sezary's syndrome; hypophysitis; chronic adrenal insufficiency; Addison's disease; ischemia-reperfusion injury of organs which occurs upon preservation; endotoxin shock; pseudomembranous colitis; colitis caused by drug or radiation; ischemic acute renal insufficiency; chronic renal insufficiency; lung cancer; malignancy of lymphoid origin; acute or chronic lymphocytic leukemias; lymphoma; pulmonary emphysema; cataracta; siderosis; retinitis pigmentosa; senile macular degeneration; vitreal scarring; corneal alkali burn; dermatitis erythema; ballous dermatitis; cement dermatitis; gingivitis; periodontitis; sepsis; pancreatitis; peripheral artery disease; carcinogenesis; solid cancer tumors; metastasis of carcinoma; hypobaropathy; autoimmune hepatitis; primary biliary cirrhosis; sclerosing cholangitis; partial liver resection; acute liver necrosis; cirrhosis; alcoholic cirrhosis; hepatic failure; fulminant hepatic failure; late-onset hepatic failure; and "acute-on-chronic" liver failure.

Preferred diseases or disorders to be treated and/or prevented with the compounds of Formula (I) are selected from the group consisting of rejection of transplanted organs such as kidney, liver, heart, lung, pancreas, cornea, and skin; graft-versus-host diseases brought about by stem cell transplantation; autoimmune syndromes including rheumatoid arthritis, multiple sclerosis, inflammatory bowel diseases such as Crohn's disease and ulcerative colitis, psoriasis, psoriatic arthritis, thyroiditis such as Hashimoto's thyroiditis, uveo-retinitis; atopic diseases such as rhinitis, conjunctivitis, dermatitis; asthma; type I diabetes; post-infectious autoimmune diseases including rheumatic fever and post-infectious glomerulonephritis; solid cancers and tumor metastasis.

Particularly preferred diseases or disorders to be treated and/or prevented with the compounds of Formula (I) are selected from the group consisting of rejection of transplanted organs selected from kidney, liver, heart and lung; graft-versus-host diseases brought about by stem cell transplantation; autoimmune syndromes selected from rheumatoid arthritis, multiple sclerosis, psoriasis, psoriatic arthritis, Crohn's disease, and Hashimoto's thyroiditis; and atopic dermatitis. Very preferably the diseases or disorders to be treated and/or prevented with the compounds of Formula (I) are selected from multiple sclerosis and psoriasis.

The present invention also relates to a method for the prevention or treatment of a disease or disorder mentioned herein comprising administering to a subject a pharmaceutically active amount of a compound of Formula (I).

Furthermore, compounds of the Formula (I) are also useful, in combination with one or several immunomodulating agents, for the prevention and/or treatment of the diseases and disorders mentioned herein. According to a preferred embodiment of the invention, said agents are selected from the group consisting of immunosuppressants, corticosteroids, NSAID's, cytotoxic drugs, adhesion molecule inhibitors, cytokines, cytokine inhibitors, cytokine receptor antagonists and recombinant cytokine receptors.

The present invention also relates to the use of a compound of Formula (I) for the preparation of a pharmaceutical composition, optionally for use in combination with one or several immunomodulating agents, for the prevention or treatment of the diseases and disorders mentioned herein.

The compounds of Formula (I) can be manufactured by the methods given below, by the methods given in the Examples or by analogous methods. Optimum reaction conditions may vary with the particular reactants or solvents used, but such conditions can be determined by a person skilled in the art by routine optimisation procedures.

Compounds of the Formula (I) of the present invention can be prepared according to the general sequence of reactions outlined below. Only a few of the synthetic possibilities leading to compounds of Formula (I) are described.

Compounds of Formula (I) which represent a 5-pyridin-4-yl-[1,2,4]oxadiazole derivative are prepared by reacting a compound of Structure 1 in a solvent such as toluene, pyridine, DMF, THF, dioxane, DME, etc. at rt or elevated temperatures in the presence or absence of auxiliaries such as acids (e.g. TFA, acetic acid, HCl, etc.), bases (e.g. NaH, NaOAc, Na$_2$CO$_3$, K$_2$CO$_3$, NEt$_3$, etc.), tetraalkylammonium salts, or water removing agents (e.g. oxalyl chloride, a carboxylic acid anhydride, POCl$_3$, PCl$_5$, P$_4$O$_{10}$, molecular sieves, Burgess reagent, etc.) (Lit.: e.g. A. R. Gangloff, J. Litvak, E. J. Shelton, D. Sperandio, V. R. Wang, K. D. Rice, *Tetrahedron Lett.* 42 (2001), 1441-1443; T. Suzuki, K. Iwaoka, N. Imanishi, Y. Nagakura, K. Miyta, H. Nakahara, M. Ohta, T. Mase, *Chem. Pharm. Bull.* 47 (1999), 120-122; R. F. Poulain, A. L. Tartar, B. P. Déprez, *Tetrahedron Lett.* 42 (2001), 1495-1498; R. M. Srivastava, F. J. S. Oliveira, D. S. Machado, R. M. Souto-Maior, *Synthetic Commun.* 29 (1999), 1437-1450; E. O. John, J. M. Shreeve, *Inorganic Chemistry* 27 (1988), 3100-3104; B. Kaboudin, K. Navaee, *Heterocycles* 60 (2003), 2287-2292).

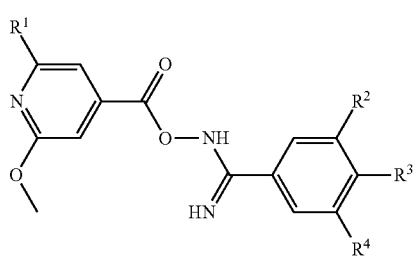

Structure 1

Compounds of Structure 1 may be prepared by reacting a compound of Structure 2 with a compound of Structure 3 in a solvent such as DMF, THF, DCM, etc. in the presence of one or more coupling agents such as TBTU, DCC, EDC, HBTU, CDI, etc. and in the presence or absence of a base such as NEt$_3$, DIPEA, NaH, K$_2$CO$_3$, etc. (Lit.: e.g. A. Hamze, J.-F. Hernandez, P. Fulcrand, J. Martinez, *J. Org. Chem.* 68 (2003), 7316-7321; and the literature cited above).

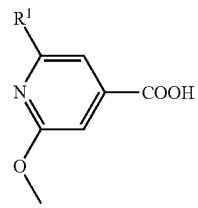

Structure 2

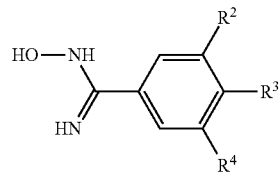

Structure 3

Compounds of Formula (I) which represent a 3-pyridin-4-yl-[1,2,4]oxadiazole derivative are prepared in an analogous fashion (Lit.: e.g. C. T. Brain, J. M. Paul, Y. Loong, P. J. Oakley, *Tetrahedron Lett.* 40 (1999), 3275-3278) by reacting a compound of Structure 4 with a compound of Structure 5 and subsequent cyclisation of the corresponding hydroxyamidine ester intermediate.

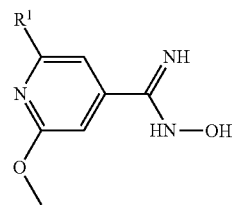

Structure 4

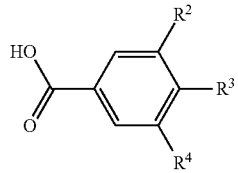

Structure 5

Compounds of Structure 3 and 4 may be prepared by reacting a compound of Structure 6 and 7, respectively, with hydroxylamine or one of its salts in a solvent such as MeOH, EtOH, pyridine, etc. in the presence or absence of a base such as Na$_2$CO$_3$, K$_2$CO$_3$, potassium tert.butylate, NEt$_3$, etc. (Lit.: e.g. E. Meyer, A. C. Joussef, H. Gallardo, Synthesis 2003, 899-905, WO 2004/035538 (Merck & Co., Inc., USA)).

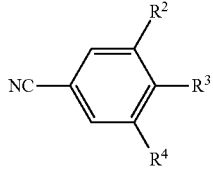

Structure 6

Structure 7

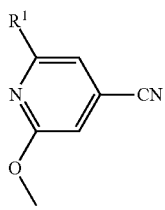

Depending on the nature of the functionalities present in residue $R^3$ in Structures 3, 5 and 6, these functionalities may require temporary protection. Appropriate protecting groups are known to a person skilled in the art and include e.g. a benzyl or a trialkylsilyl group to protect an alcohol, a ketal to protect a diol, etc. These protecting groups may be employed according to standard methodology (e.g. T. W. Greene, P. G. M. Wuts, Protective Groups in Organic Synthesis, $3^{rd}$ Edition, Wiley New York, 1991; P. J. Kocienski, Protecting Groups, Thieme Stuttgart, 1994). Alternatively, the desired residues $R^3$ and $R^4$, in particular $R^3$, may also be introduced in later steps that follow the coupling of the pyridine compounds of Structure 2 or 4 with the phenyl derivatives of Structure 3 or 5 by using a suitable precursor of a compound of Structure 3 and 5. The desired residues $R^3$ can be introduced by a series of one or several alkylating, acylating and/or displacement reactions known to a person skilled in the art. The phenyl compounds of Structure 3, 5 and 6 or their precursors are either commercially available or are prepared according to procedures known to a person skilled in the art.

Structure 8

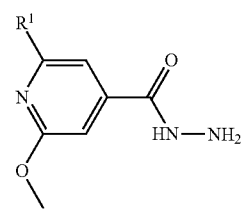

Structure 9

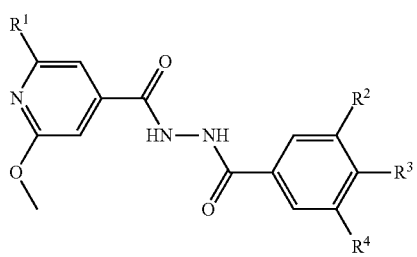

Compounds of Formula (I) which represent a 2-pyridin-4-yl-[1,3,4]oxadiazole are prepared similarly by reacting a compound of Structure 2 with hydrazine (by using a coupling reagent such as TBTU, DCC, EDC, HBTU, PyBOP, CDI, etc.) to form a compound of Structure 8 which is then coupled with a compound of Structure 5 to give a compound of Structure 9. A compound of Structure 9 can also be prepared by following the reverse reaction order i.e. by first coupling a compound of Structure 5 with hydrazine followed by reacting the corresponding hydrazide intermediate with a compound of Structure 2. Dehydration of a compound of Structure 9 to form the desired 2-pyridin-4-yl-[1,3,4]oxadiazole derivative is affected by treating a compound of Structure 9 with a reagent such as $POCl_3$, $CCl_4$ or $CBr_4$ in combination with $PPh_3$, $P_2O_5$, Burgess reagent, etc. in a solvent such as toluene, MeCN, dioxane, THF, $CHCl_3$, etc. at temperatures between 20 and 120° C. in the presence or absence of microwave irradiation. (Lit.: e.g. M. A. Garcia, S. Martin-Santamaria, M. Cacho, F. Moreno de la Llave, M. Julian, A. Martinez, B. De Pascual-Teresa, A. Ramos, J. Med. Chem. 48 (2005), 4068-4075; C. T. Brain, J. M. Paul, Y. Loong, P. J. Oakley, Tetrahedron Lett. 40 (1999), 3275-3278).

Methods that effect the transformation of a compound of Structure 2 or 5 into a compound of Structure 7 or 6, respectively, or the opposite, are known to a person skilled in the art.

Structure 10

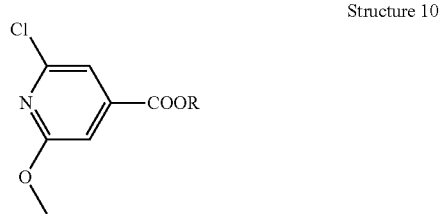

Compounds of Structure 2 may be prepared by reacting 2,6-dichloro-isonicotinic acid or a suitable ester derivative thereof with methanol in the presence or absence of a base such as NaOH, NaOMe, potassium tert. butoxide, etc. in a solvent such as methanol, THF, dioxane, etc. to give a compound of Structure 10 (R=H or preferably Me, Et, tert.-butyl, etc.) (Lit.: e.g. N. Wild, U. Groth, Eur. J. Org. Chem. 2003, 4445-4449). The compound of Structure 10 may then be reacted with a cyclopentyl Zn reagent under Negishi conditions (Lit.: e.g. H. Matsushita, E. Negishi, J. Org. Chem. 47 (1982), 4161-4165), with an appropriate cyclopentyl Grignard reagent for instance in the presence of $Fe(acac)_3$ in a solvent such as THF, dioxane, DMF, NMP, etc., or combinations thereof, at temperatures ranging from −78 to 25° C. under Furstner conditions (Lit.: e.g. A. Furstner, A. Leitner, M. Mendez, H. Krause, J. Am. Chem. Soc. 124 (2002), 13856-13863; A. Furstner, A. Leitner, Angew. Chem. 114 (2002), 632-635) or with cyclopentyl or a 1-cyclopentenyl boron derivative (Lit.: e.g. F. Kerins, D. F. O'Shea, J. Org. Chem. 67 (2002), 4968-4971) under Suzuki coupling conditions (Lit.: e.g. H. Doucet, Eur. J. Org. Chem. 2008, 2013-2030). In case 1-cyclopentenyl boron derivatives are used to introduce the carbon framework of $R^1$, a subsequent hydrogenation step is required to establish the desired cyclopentyl group. Finally, in case a pyridine-4-carboxylic acid ester has been employed in the steps described above, ester hydrolysis under basic or acid reaction conditions furnishes the desired compound of Structure 2.

Whenever the compounds of Formula (I) are obtained in the form of mixtures of enantiomers, the enantiomers can be separated using methods known to one skilled in the art: e.g. by formation and separation of diastereomeric salts or by HPLC over a chiral stationary phase such as a Regis Whelk-O1(R,R) (10 μm) column, a Daicel ChiralCel OD-H (5-10 μm) column, or a Daicel ChiralPak IA (10 μm) or AD-H (5 μm) column. Typical conditions of chiral HPLC are an isocratic mixture of eluent A (EtOH, in presence or absence of an amine such as $NEt_3$, diethylamine) and eluent B (hexane), at a flow rate of 0.8 to 150 mL/min.

EXPERIMENTAL PART

The following examples illustrate the invention but do not at all limit the scope thereof.

All temperatures are stated in ° C. Compounds are characterized by $^1$H-NMR (300 MHz) or $^{13}$C-NMR (75 MHz) (Varian Oxford; chemical shifts are given in ppm relative to the solvent used; multiplicities: s=singlet, d=doublet, t=triplet, p=pentuplet, hex=hexet, hept=heptet, m=multiplet, br=broad, coupling constants are given in Hz); by LC-MS (Finnigan Navigator with HP 1100 Binary Pump and DAD, column: 4.6×50 mm, Zorbax SB-AQ, 5 μm, 120 Å, gradient: 5-95% MeCN in water, 1 min, with 0.04% TFA, flow: 4.5 mL/min, $t_R$ is given in min; retention times or LC-MS marked with * refer to an LC run under the following conditions: Waters Xbridge C18, 2.5 μm, 4.6×30 mm, gradient: 5-95% MeCN in water, 1 min, with 0.04% TFA, flow: 4.5 mL/min; retention times or LC-MS marked with ** refer to an LC run under the following conditions: column: Zorbax Extended C18, 1.8 μm, 4.6×20 mm, gradient: 5-95% MeCN in water, 1 min, with 0.04% TFA, flow: 4.5 mL/min); by TLC (TLC-plates from Merck, Silica gel 60 $F_{254}$); or by melting point. Compounds are purified by prep. HPLC (column: X-terra RP18, 50×19 mm, 5 μm, gradient: 10-95% MeCN in water containing 0.5% of formic acid) or by MPLC (Labomatic MD-80-100 pump, Linear UVIS-201 detector, column: 350× 18 mm, Labogel-RP-18-5s-100, gradient: 10% MeOH in water to 100% MeOH).

ABBREVIATIONS

As Used Herein aq. aqueous
BSA bovine serum albumin
Burgess reagent methoxycarbonylsulfamoyl triethylammonium hydroxide
CC column chromatography
CDI carbonyl diimidazole
DCC N,N'-dicyclohexyl carbodiimide
DCM dichloromethane
DIPEA Hüning's base, diethylisopropylamine
DME 1,2-dimethoxyethane
DMF dimethylformamide
DMSO dimethylsulfoxide
dppf 1,1'-bis(diphenylphosphino)ferrocene
EA ethyl acetate
EDC N-(3-dimethylaminopropyl)-N'-ethyl-carbodiimide
Et ethyl
EtOH ethanol
FBS fetal bovine serum
Fe(acac)$_3$ iron (III) acetylacetone-complex
FRET fluorescence resonance energy transfer
h hour(s)
HBTU O-(benzotriazol-1-yl)-N,N,N',N'-tetramethyluronium hexafluorophosphate
HEPES 4-(2-hydroxyethyl)-1-piperazineethanesulfonic acid
HOBt 1-hydroxy-benzotriazole
HPLC high performance liquid chromatography
HV high vacuum conditions
LC-MS liquid chromatography-mass spectrometry
Lit. literature
Me methyl
MeCN acetonitrile
MeOH methanol
min minute(s)
MPLC medium pressure liquid chromatography
NaOAc sodium acetate
NEAA non-essential amino acids
NEt$_3$ triethylamine
NMP 1-methyl-2-pyrrolidone
org. organic
PEG polyethylene glycol
PPh$_3$ triphenylphosphine
PyBOP benzotriazol-1-yl-oxy-tris-pyrrolidino-phosphonium-hexafluoro-phosphate
prep. preparative
rt room temperature
sat. saturated
S1P sphingosine 1-phosphate
TBME tert.-butyl methyl ether
TBTU 2-(1H-benzotriazole-1-yl)-1,2,3,3-tetramethyluronium tetrafluoroborate
tert. tertiary
TFA trifluoroacetic acid
THF tetrahydrofuran
TLC thin layer chromatography
$t_R$ retention time Preparation of Intermediates 2-Cyclopentyl-6-methoxy-isonicotinic acid a) To a solution of 2,6-dichloroisonicotinic acid (200 g, 1.04 mol) in methanol (3 L), 32% aq. NaOH (770 mL) is added. The stirred mixture becomes warm (34° C.) and is then heated to 70° C. for 4 h before it is cooled to rt. The mixture is neutralised by adding 32% aq. HCl (100 mL) and 25% aq. HCl (700 mL). The mixture is stirred at rt overnight. The white precipitate that forms is collected, washed with methanol and dried. The filtrate is evaporated and the residue is suspended in water (200 mL). The resulting mixture is heated to 60° C. Solid material is collected, washed with water and dried. The combined crops give 2-chloro-6-methoxy-isonicotinic acid (183 g) as a white solid; LC-MS: $t_R$=0.80 min, [M+1]$^+$=187.93.

b) To a suspension of 2-chloro-6-methoxy-isonicotinic acid (244 g, 1.30 mol) in methanol (2.5 L), H$_2$SO$_4$ (20 mL) is added. The mixture is stirred at reflux for 24 h before it is cooled to 0° C. The solid material is collected, washed with methanol (200 mL) and water (500 mL) and dried under HV to give 2-chloro-6-methoxy-isonicotinic acid methyl ester (165 g) as a white solid; LC-MS: $t_R$=0.94 min, [M+1]$^+$=201.89.

c) Under argon, Pd(dppf) (2.00 g, 2.4 mmol) is added to a solution of 2-chloro-6-methoxy-isonicotinic acid methyl ester (32.0 g, 0.159 mol) in THF (100 mL). A 0.5 M solution of cyclopentylzincbromide in THF (330 mL) is added via dropping funnel. Upon complete addition, the mixture is heated to 85° C. for 3 h before it is cooled to rt. The reaction mixture is concentrated, diluted with 1 N aq. HCl (275 mL) and extracted with TBME (275 mL). The org. extract is washed with 1 N aq. HCl (275 mL), filtered over Celite and washed with water (275 mL). The org. extract is concentrated and dried to give crude 2-cyclopentyl-6-methoxy-isonicotinic acid methyl ester (34.8 g) as a brown oil. This material is dissolved in ethanol (180 mL), water (45 mL) and 32% aq. NaOH solution (45 mL). The mixture is stirred at 90° C. for 30 min before it is cooled to rt. The ethanol is evaporated and the remaining solution is diluted with water (150 mL) and extracted with DCM (200 mL). The aq. phase is acidified by adding 32% aq. HCl (45 mL) and then extracted twice with DCM (2×100 mL). The org. extracts are combined and concentrated. The crude product is purified by crystallisation from hot acetonitrile (174 mL). The crystalline material is collected and dried at 50° C. under HV. From the mother liquor a second crop of crystalline material can be obtained. The two crops are combined to give 2-cyclopentyl-6-methoxy-isonicotinic acid (24.1 g) as a pale grey crystalline powder; LC-MS: $t_R$=0.93 min, [M+1]$^+$=222.02; $^1$H NMR (CDCl$_3$): δ1.68-1.77 (m, 2H), 1.81-1.90 (m, 4H), 2.03-2.12 (m, 2H), 3.15-3.25 (m, 1H), 3.99 (s, 3H), 7.18 (d, J=1.0 Hz, 1H), 7.35 (d, J=0.8 Hz, 1H).

2-Cyclopentyl-N-hydroxy-6-methoxy-isonicotinamidine a) A solution of 2-cyclopentyl-6-methoxy-isonicotinic acid methyl ester (3.19 g, 13.6 mmol) in 7 N NH$_3$ in methanol (50 mL) is stirred at 60° C. for 18 h. The solvent is removed in vacuo and the residue is dried under HV to give crude 2-cyclopentyl-6-methoxy-isonicotinamide (3.35 g) as a pale yellow solid; LC-MS**: $t_R$=0.57 min, [M+1]$^+$=221.38.

b) Pyridine (8.86 g, 91.3 mmol) is added to a solution of 2-cyclopentyl-6-methoxy-isonicotinamide (3.35 g, 15.2 mmol) in DCM (100 mL). The mixture is cooled to 0° C. before trifluoroacetic acid anhydride (9.58 g, 45.6 mmol) is added portionwise. The mixture is stirred at 0° C. for 1 h before it is diluted with DCM (100 mL) and washed with sat. aq. NaHCO$_3$ solution (100 mL) and brine (100 mL). The separated org. phase is dried over MgSO$_4$, filtered and concentrated. The crude product is purified by CC on silica gel eluting with heptane:EA 9:1 to give 2-cyclopentyl-6-methoxy-isonicotinonitrile (2.09 g) as a pale yellow oil; LC-MS**: $t_R$=0.80 min, [M+1]$^+$=not detectable; $^1$H NMR (D$_6$-DMSO): δ 1.61-1.82 (m, 6H), 1.94-2.03 (m, 2H), 3.16 (quint, J=7.8 Hz, 1H), 3.89 (s, 3H), 7.15 (s, 1H), 7.28 (s, 1H).

c) To a solution of 2-cyclopentyl-6-methoxy-isonicotinonitrile (2.09 g, 10.3 mmol) in methanol (100 mL), hydroxylamine hydrochloride (2.15 g, 31.0 mmol) and NaHCO$_3$ (3.04 g, 36.2 mmol) are added. The mixture is stirred at 60° C. for 18 h before it is filtered and the filtrate is concentrated. The residue is dissolved in EA (300 mL) and washed with water (30 mL). The washings are extracted back with EA (4×100 mL) and DCM (4×100 mL). The combined org. extracts are dried over MgSO$_4$, filtered, concentrated and dried under HV to give the title compound (2.74 g) as a white solid; LC-MS**: $t_R$=0.47 min, [M+1]$^+$=236.24; $^1$H NMR (D$_6$-DMSO): δ 1.61-1.82 (m, 6H), 1.92-2.01 (m, 2H), 3.04-3.13 (m, 1H), 3.84 (s, 3H), 5.90 (s, 2H), 6.86 (s, 1H), 7.13 (s, 1H), 9.91 (s, 1H).

2-Cyclopentyl-6-methoxy-isonicotinic acid hydrazide a) To a solution of 2-cyclopentyl-6-methoxy-isonicotinic acid (2.00 g, 9.04 mmol), hydrazinecarboxylic acid benzyl ester (1.50 g, 9.04 mmol) and DIPEA (2.34 g, 18.1 mmol) in DCM (40 mL), TBTU (3.19 g, 9.94 mmol) is added. The mixture is stirred at rt for 2 h before it is diluted with EA (250 mL), washed twice with sat. aq. NaHCO$_3$ solution (150 mL) followed by brine (100 mL), dried over MgSO$_4$, filtered and concentrated. The crude product is purified by CC on silica gel eluting with heptane:EA 4:1 to give N'-(2-cyclopentyl-6-methoxy-pyridine-4-carbonyl)-hydrazinecarboxylic acid benzyl ester (2.74 g) as a pale yellow oil; LC-MS**: $t_R$=0.74 min, [M+1]$^+$=369.69; $^1$H NMR (D$_6$-DMSO): δ 1.62-1.83 (m, 6H), 1.95-2.05 (m, 2H), 3.10-3.21 (m, 1H), 3.88 (s, 3H), 5.13 (s, 2H), 6.97 (s, 1H), 7.23 (s, 1H), 7.28-7.40 (m, 5H), 9.45 (s, 1H), 10.52 (s, 1H).

b) Pd/C (500 mg, 10% Pd) is added to a solution of N'-(2-cyclopentyl-6-methoxy-pyridine-4-carbonyl)-hydrazinecarboxylic acid benzyl ester (2.74 g, 7.42 mmol) in THF (50 mL) and methanol (50 mL). The mixture is stirred at rt under 1 bar of H$_2$ for 25 h. The catalyst is removed by filtration and the filtrate is concentrated and dried under HV to give the title compound (1.58 g) as an off-white solid; LC-MS**: $t_R$=0.51 min, [M+1]$^+$=236.20; $^1$H NMR (D$_6$-DMSO): δ 1.60-1.82 (m, 6H), 1.94-2.03 (m, 2H), 3.08-3.19 (m, 1H), 3.86 (s, 3H), 4.56 (s br, 2H), 6.93 (d, J=1.0 Hz, 1H), 7.20 (d, J=1.0 Hz, 1H), 9.94 (s, 1H).

3-Ethyl-4-hydroxy-5-methyl-benzonitrile

The title compound is prepared from 3-ethyl-4-hydroxy-5-methyl-benzaldehyde following literature procedures (A. K. Chakraborti, G. Kaur, *Tetrahedron* 55 (1999) 13265-13268); LC-MS: $t_R$=0.90 min; $^1$H NMR (CDCl$_3$): δ1.24 (t, J=7.6 Hz, 3H), 2.26 (s, 3H), 2.63 (q, J=7.6 Hz, 2H), 5.19 (s, 1H), 7.30 (s, 2H).

3-Chloro-4-hydroxy-5-methyl-benzonitrile

The title compound is prepared from commercially available 2-chloro-6-methyl-phenol in analogy to literature procedures (see 3-ethyl-4-hydroxy-5-methyl-benzonitrile); LC-MS: $t_R$=0.85 min. $^1$H NMR (CDCl$_3$): δ2.33 (s, 3H), 6.10 (s, 1H), 7.38 (s, 1H), 7.53 (d, J=1.8 Hz, 1H).

3-Ethyl-4,N-dihydroxy-5-methyl-benzamidine

The title compound is prepared from 3-ethyl-4-hydroxy-5-methyl-benzonitrile or from commercially available 2-ethyl-6-methyl-phenol following literature procedures (G. Trapani, A. Latrofa, M. Franco, C. Altomare, E. Sanna, M. Usala, G. Biggio, G. Liso, *J. Med. Chem.* 41 (1998) 1846-1854; A. K. Chakraborti, G. Kaur, *Tetrahedron* 55 (1999) 13265-13268; E. Meyer, A. C. Joussef, H. Gallardo, *Synthesis* 2003, 899-905); LC-MS: $t_R$=0.55 min; $^1$H NMR (D$_6$-DMSO): δ 9.25 (s br, 1H), 7.21 (s, 2H), 5.56 (s, 2H), 2.55 (q, J=7.6 Hz, 2H), 2.15 (s, 3H), 1.10 (t, J=7.6 Hz, 3H).

3-Chloro-4,N-dihydroxy-5-methyl-benzamidine

The title compound is prepared from commercially available 2-chloro-6-methyl-phenol in analogy to literature procedures (e.g. B. Roth et al. *J. Med. Chem.* 31 (1988) 122-129; and literature cited for 3-ethyl-4,N-dihydroxy-5-methyl-benzamidine); 3-chloro-4-hydroxy-5-methyl-benzaldehyde: LC-MS: $t_R$=0.49 min, [M+1]$^+$=201.00; $^1$H NMR 82.24 (s, 2H), 2.35 (s, 4H), 5.98 (s br, 1H), 7.59 (d, J=1.8 Hz, 1H), 7.73 (d, J=1.8 Hz, 1H), 9.80 (s, 1H); 3-chloro-4,N-dihydroxy-5-methyl-benzamidine: $^1$H NMR (D$_6$-DMSO): δ 2.21 (s, 3H), 5.72 (s br, 2H), 7.40 (s, 1H), 7.48 (s, 1H), 9.29 (s br, 1H), 9.48 (s br, 1H).

3-Chloro-4,N-dihydroxy-5-methoxy-benzamidine

The title compound is prepared from commercially available 3-chloro-4-hydroxy-5-methoxy-benzaldehyde in analogy to the literature cited for 3-ethyl-4,N-dihydroxy-5-methyl-benzamidine; LC-MS: $t_R$=0.49 min, [M+1]$^+$=216.96; $^1$H NMR (D$_6$-DMSO): δ 3.84 (s, 3H), 5.79 (s, 2H), 7.22 (d, J=1.5 Hz, 1H), 7.27 (d, J=1.8 Hz, 1H), 9.52 (s, 1H), 9.58 (s br, 1H).

3-Chloro-4-(2,2-diethoxyethoxy)-N-hydroxy-5-methylbenzimidamide a) To a mixture of 3-chloro-4-hydroxy-5-methyl-benzonitrile (4.16 g, 24.8 mmol) and Cs$_2$SO$_3$ (16.2 g, 49.6 mmol) in DMF (60 mL) bromoacetaldehyde diethylacetal (5.90 g, 29.9 mmol) is added. The mixture is stirred at 80° C. for 18 h. The brown suspension is dissolved in water (200 mL) and extracted four times with EA (4×100 mL). The combined org. extracts are dried over MgSO$_4$, filtered and concentrated. The crude product is purified by MPLC on silica gel eluting with a gradient of EA in heptane to give 3-chloro-4-(2,2-diethoxy-ethoxy)-5-methylbenzonitrile (3.60 g) as a white solid; LC-MS: $t_R$=0.92 min, [M+1]$^+$=not detectable; $^1$H NMR (CDCl$_3$): δ 7.54 (d, J=1.6 Hz, 1H), 7.41 (d, J=0.8 Hz, 1H), 4.88 (t, J=5.2 Hz, 1H), 4.06 (d, J=5.2 Hz, 2H), 3.72-3.83 (m, 2H), 3.58-3.71 (m, 2H), 2.38 (s, 3H), 1.26 (t, J=7.1 Hz, 6H).

b) To a solution of 3-chloro-4-(2,2-diethoxyethoxy)-5-methylbenzonitrile (4.54 g, 16.0 mmol) in methanol (50 mL), hydroxylamine hydrochloride (3.34 g, 48.0 mmol) and NaHCO$_3$ (2.69 g, 32.0 mmol) is added. The mixture is stirred at 75° C. for 2 h before it is diluted with EA (120 mL) and washed with water (100 mL). The washing is extracted twice with EA (2×75 mL). The combined org. extracts are dried over MgSO$_4$, filtered and concentrated to give the title compound (4.43 g) as a beige wax which slowly solidifies upon standing; LC-MS: $t_R$=0.55 min, [M+1]$^+$=317.28.

3-Chloro-4-(2,2-dimethoxyethoxy)-N-hydroxy-5-methoxybenzimidamide

The title compound is prepared in analogy to 3-chloro-4-(2,2-diethoxyethoxy)-N-hydroxy-5-methylbenzimidamide; LC-MS: $t_R$=0.53 min, [M+1]$^+$=305.18.

4-Benzyloxy-3-ethyl-5-methyl-benzoic acid a) To a solution of 3-ethyl-4-hydroxy-5-methyl-benzaldehyde (34.9 g, 0.213 mol, prepared from 2-ethyl-6-methyl-phenol according to the literature cited for 3-ethyl-4,N-dihydroxy-5-methyl-benzamidine) in MeCN (350 mL), K$_2$CO$_3$ (58.7 g, 0.425 mol) and benzylbromide (36.4 g, 0.213 mol) are added. The mixture is stirred at 60° C. for 2 h before it is cooled to rt, diluted with water and extracted twice with EA. The org. extracts are washed with water and concentrated to give crude 4-benzyloxy-3-ethyl-5-methyl-benzaldehyde (45 g) as an orange oil. $^1$H NMR (CDCl$_3$): δ 1.29 (t, J=7.5 Hz, 3H), 2.40 (s, 3H), 2.77 (q, J=7.8 Hz, 2 H), 4.90 (s, 2H), 7.31-7.52 (m, 5H), 7.62 (d, J=1.5 Hz, 1H), 7.66 (d, J=1.8 Hz, 1H), 9.94 (s, 1H).

b) To a mixture of 4-benzyloxy-3-ethyl-5-methyl-benzaldehyde (132 g, 0.519 mol) and 2-methyl-2-butene (364 g, 5.19 mol) in tert.-butanol (1500 mL), a solution of NaH$_2$PO$_4$ dihydrate (249 g, 2.08 mol) in water (1500 mL) is added. To this mixture, NaClO$_2$ (187.8 g, 2.08 mol) is added in portions. The temperature of the reaction mixture is kept below 30° C., and evolution of gas is observed. Upon completion of the addition, the orange bi-phasic mixture is stirred well for 3 h before it is diluted with TBME (1500 mL). The org. layer is separated and washed with 20% aq. NaHS solution (1500 mL) and water (500 mL). The org. phase is then extracted three times with 0.5 N aq. NaOH (1000 mL), the aq. phase is acidified with 25% aq. HCl (500 mL) and extracted twice with TBME (1000 mL). These org. extracts are combined and evaporated to dryness to give the title compound; $^1$H NMR (D$_6$-DMSO): δ 1.17 (t, J=7.5 Hz, 3H), 2.31 (s, 3H), 2.67 (q, J=7.5 Hz, 2H), 4.86 (s, 2H), 7.34-7.53 (m, 5H), 7.68 (s, 2H), 12.70 (s, 1H).

Example 1

3-((2-(4-(5-(2-Cyclopentyl-6-methoxypyridin-4-yl)-1,2,4-oxadiazol-3-yl)-2-ethyl-6-methylphenoxy)ethyl)amino)propanoic acid a) A solution of 2-cyclopentyl-6-methoxy-isonicotinic acid (21.0 g, 102 mmol), 3-ethyl-4,N-dihydroxy-5-methyl-benzamidine (20.0 g, 103 mmol) and HOBt (1.24 g, 9 mmol) in THF (200 mL) is cooled to 5° C. before a solution of DCC (20.0 g, 97 mmol) in THF (100 mL) is added dropwise. Upon complete addition, the mixture is stirred at rt for 18 h then at 75° C. for 48 h. The solvent is evaporated and the remaining residue is dissolved in TBME (200 mL). The precipitate that forms is removed, filtered off and washed with additional TBME (200 mL). The filtrate is washed with approximately 4% aq. NaHCO$_3$ solution (100 mL) and water (100 mL) and concentrated. The crude product is recrystallised from hot acetonitrile (200 mL) to give 4-[5-(2-cyclopentyl-6-methoxy-pyridin-4-yl)-[1,2,4]oxadiazol-3-yl]-2-ethyl-6-methyl-phenol (28.6 g) as a white solid; $^1$H NMR (CDCl$_3$): δ1.33 (t, J=7.5 Hz, 3H), 1.70-1.80 (m, 2H), 1.84-1.96 (m, 4H), 2.05-2.16 (m, 2H), 2.36 (s, 3H), 2.74 (q, J=7.3 Hz, 2H), 3.25 (quint, J=7.5 Hz, 1H), 4.02 (s, 3H), 5.01 (s), 7.31 (s, 1H), 7.51 (s, 1H), 7.85 (s, 2H).

b) To a solution of 4-[5-(2-cyclopentyl-6-methoxy-pyridin-4-yl)-[1,2,4]oxadiazol-3-yl]-2-ethyl-6-methyl-phenol (1.26 g, 3.32 mmol) in DMF (20 mL), Cs$_2$CO$_3$ (6.49 g, 19.9 mmol) is added. The mixture is stirred at rt for 10 min before 2-bromoethanol (2.07 g, 16.6 mmol) is added. The mixture is stirred at 60° C. for 5 days. The mixture is cooled to rt, diluted with sat. aq. NaHCO$_3$ solution (50 mL) and extracted twice with EA (2×200 mL). The org. extracts are combined and concentrated. The crude product is purified by CC on silica gel eluting with heptane:EA 4:1 to give 2-(4-(5-(2-cyclopentyl-6-methoxypyridin-4-yl)-1,2,4-oxadiazol-3-yl)-2-ethyl-6-methylphenoxy)ethanol (639 mg) as a pale yellow oil; $^1$H NMR (CDCl$_3$): δ: 7.90 (s, 1H), 7.88 (s, 1H), 7.51 (s, 1H), 7.31 (s, 1H), 4.02 (s, 3H), 3.97-4.01 (m, 4H), 3.21-3.29 (m, 1H), 2.79 (q, J=7.6 Hz, 2H), 2.42 (s, 3H), 2.15 (t, J=5.5 Hz, 1H), 2.06-2.14 (m, 2H), 1.83-1.95 (m, 4H), 1.68-1.80 (m, 2H), 1.33 (t, J=7.6 Hz, 3H).

c) To a solution of 2-(4-(5-(2-cyclopentyl-6-methoxypyridin-4-yl)-1,2,4-oxadiazol-3-yl)-2-ethyl-6-methylphenoxy)ethanol (638 mg, 1.51 mmol) in THF, DIPEA (389 mg, 3.01 mmol) is added. The mixture is cooled to 0° C. before methanesulfonyl chloride (207 mg, 1.81 mmol) is added. The mixture is stirred at rt for 30 min before it is diluted with EA (100 mL) and washed with sat. aq. NaHCO$_3$ solution (50 mL) and brine (50 mL). The org. extract is dried over MgSO$_4$, filtered and concentrated to give 2-(4-(5-(2-cyclopentyl-6-methoxypyridin-4-yl)-1,2,4-oxadiazol-3-yl)-2-ethyl-6-methylphenoxy)ethyl methanesulfonate (733 mg) as a yellow oil; LC-MS: $t_R$=1.19 min, [M+H]$^+$=502.05.

d) A solution of 2-(4-(5-(2-cyclopentyl-6-methoxypyridin-4-yl)-1,2,4-oxadiazol-3-yl)-2-ethyl-6-methylphenoxy)ethyl methanesulfonate (245 mg, 0.488 mmol), ethyl 3-aminopropanoate (286 mg, 2.44 mmol, obtained from the corresponding HCl salt by exchanging the HCl using carbonate ion exchange) and Et$_3$N (247 mg, 2.44 mmol) in ethanol (6 mL) is stirred at 60° C. for 72 h. The mixture is diluted with sat. aq. NaHCO$_3$ solution and extracted twice with DCM. The combined org. extracts are dried over Na$_2$SO$_4$, filtered and concentrated. The crude product is purified on prep. TLC plates using DCM:MeOH 9:1 to give ethyl 3-((2-(4-(5-(2-cyclopentyl-6-methoxypyridin-4-yl)-1,2,4-oxadiazol-3-yl)-2-ethyl-6-methyl-phenoxy)ethyl)amino)propanoate (88 mg) as a pale yellow oil; LC-MS: $t_R$=0.99 min, [M+H]$^+$=523.13.

e) A solution of ethyl 3-((2-(4-(5-(2-cyclopentyl-6-methoxypyridin-4-yl)-1,2,4-oxadiazol-3-yl)-2-ethyl-6-methyl-phenoxy)ethyl)amino)propanoate (88 mg, 0.168 mmol) in MeOH (0.5 mL), THF (0.5 mL) and 2 N aq. LiOH (0.2 mL) is stirred at rt for 2 h. The mixture is concentrated, diluted with 2 N aq. HCl (10 mL) and extracted four times with DCM (4×20 mL). The combined org. extracts are dried over MgSO$_4$, filtered and concentrated. The crude product is purified by prep. HPLC to give the title compound (63 mg) as an off-white solid; LC-MS: t$_R$=0.93 min, [M+H]$^+$=495.12; $^1$H NMR (CDCl$_3$): δ 8.37 (s br, 2H), 7.78 (s, 1H), 7.72 (s, 1 H), 7.43 (s, 1H), 7.20 (s, 1H), 4.07-4.18 (m, 2H), 3.99 (s, 3H), 3.34-3.42 (m, 2H), 3.16-3.34 (m, 3H), 2.62-2.76 (m, 4H), 2.33 (s, 3H), 2.09 (m, 2H), 1.81-1.94 (m, 4H), 1.68-1.79 (m, 2H), 1.27 (t, J=7.5 Hz, 3H).

Example 2

1-(2-(4-(5-(2-Cyclopentyl-6-methoxypyridin-4-yl)-1,2,4-oxadiazol-3-yl)-2-ethyl-6-methylphenoxy)ethyl)azetidine-3-carboxylic acid The title compound (123 mg) is obtained as an off-white foam in analogy to Example 1 starting from 2-(4-(5-(2-cyclopentyl-6-methoxypyridin-4-yl)-1,2,4-oxadiazol-3-yl)-2-ethyl-6-methylphenoxy)ethyl methanesulfonate (500 mg, 0.997 mmol) and azetidine-3-carboxylic acid methyl ester (302 mg, 1.99 mmol); LC-MS: t$_R$=0.88 min, [M+H]$^+$=507.23; $^1$H NMR (CDCl$_3$): δ 8.20 (s, 1H), 7.92 (d, J=1.8 Hz, 1H), 7.89 (d, J=1.6 Hz, 1H), 7.55 (s, 1H), 4.37-4.48 (m, 4H), 4.08-4.13 (m, 2H), 4.01 (s, 3H), 3.69-3.74 (m, 2H), 3.49-3.59 (m, 1H), 3.26-3.31 (m, 1H), 2.79 (q, J=7.7 Hz, 2H), 2.42 (s, 3H), 2.08-2.17 (m, 2H), 1.86-1.98 (m, 4H), 1.74-1.82 (m, 2H), 1.34 (t, J=7.5 Hz, 3H).

Example 3

(S)-1-(4-(5-(2-Cyclopentyl-6-methoxypyridin-4-yl)-1,2,4-oxadiazol-3-yl)-2-ethyl-6-methylphenoxy)-3-(2-hydroxyethyl)amino)propan-2-ol a) To a solution of 4-[5-(2-cyclopentyl-6-methoxy-pyridin-4-yl)-[1,2,4]oxadiazol-3-yl]-2-ethyl-6-methyl-phenol (2.32 g, 4.91 mmol) in 2-propanol (60 mL) and 3 N aq. NaOH (6 mL), (R)-epichlorohydrine (4.55 g, 49.1 mmol) is added. The mixture is stirred at 45° C. for 6 h before it is diluted with EA (100 mL) and washed twice with 1 N aq. NaOH (2×15 mL) followed by brine (25 mL). The org. extract is dried over MgSO$_4$, filtered and concentrated. The crude product is purified by MPLC on silica gel eluting with heptane:EA 1:1 to give (S)-5-(2-cyclopentyl-6-methoxypyridin-4-yl)-3-(3-ethyl-5-methyl-4-(oxiran-2-ylmethoxy)phenyl)-1,2,4-oxadiazole (2.04 g) as a colourless wax; LC-MS: t$_R$=1.52 min, [M+H]$^+$=436.11; $^1$H NMR (CDCl$_3$): δ 7.88-7.90 (m, 1H), 7.85-7.88 (m, 1H), 7.51 (d, J=1.1 Hz, 1H), 7.31 (d, J=1.2 Hz, 1H), 4.14 (dd, J$_1$=11.1 Hz, J$_2$=3.1 Hz, 1H), 4.02 (s, 3H), 3.83 (dd, J$_1$=11.1 Hz, J$_2$=6.0 Hz, 1H), 3.40-3.44 (m, 1H), 3.19-3.29 (m, 1H), 2.94 (dd, J$_1$=4.9 Hz, J$_2$=4.3 Hz, 1H), 2.75-2.83 (m, 3H), 2.41 (s, 3H), 2.06-2.16 (m, 2H), 1.84-1.94 (m, 4H), 1.70-1.79 (m, 2H), 1.33 (t, J=7.5 Hz, 3H).

b) A solution of (S)-5-(2-cyclopentyl-6-methoxypyridin-4-yl)-3-(3-ethyl-5-methyl-4-(oxiran-2-ylmethoxy)phenyl)-1,2,4-oxadiazole (245 mg, 0.563 mmol) and ethanolamine (4.46 g, 4.39 mmol) in ethanol (8 mL) is stirred at 60° C. for 18 h. The solvent is evaporated and the crude product is purified by prep. HPLC to give the title compound (154 mg) as a white solid; LC-MS: t$_R$=0.73 min, [M+H]$^+$=497.25; $^1$H NMR (CD$_3$OD): δ 7.85 (s, 1H), 7.83 (s, 1H), 7.51 (s, 1H), 7.26 (s, 1H), 4.13-4.20 (m, 1H), 4.00 (s, 3H), 3.84-3.90 (m, 2H), 3.67-3.78 (m, 2H), 3.23-3.30 (m, 1H), 2.96 (dd, J$_1$=12.2 Hz, J$_2$=3.7 Hz, 1H), 2.76-2.89 (m, 5H), 2.41 (s, 3H), 2.05-2.17 (m, 2H), 1.85-1.98 (m, 4H), 1.71-1.83 (m, 2H), 1.31 (t, J=7.6 Hz, 3H).

Example 4

(S)-2-(3-(4-(5-(2-Cyclopentyl-6-methoxypyridin-4-yl)-1,2,4-oxadiazol-3-yl)-2-ethyl-6-methylphenoxy)-2-hydroxypropyl)amino)propane-1,3-diol The title compound (93 mg) is obtained as a pale yellow solid in following the procedure given for Example 3 and starting from (S)-5-(2-cyclopentyl-6-methoxypyridin-4-yl)-3-(3-ethyl-5-methyl-4-(oxiran-2-ylmethoxy)phenyl)-1,2,4-oxadiazole (100 mg, 0.230 mmol) and serinol (42 mg, 0.459 mmol); LC-MS*: t$_R$=0.92 min, [M+H]$^+$=527.27; $^1$H NMR (CDCl$_3$): δ 8.51 (s, 1H), 7.82 (s, 1H), 7.80 (s, 1H), 7.46 (s, 1H), 7.25 (s, 1H), 4.44-4.52 (m, 1H), 3.69-4.07 (m, 13H), 4.00 (s, 3H), 3.48-3.55 (m, 1H), 3.28-3.37 (m, 2H), 3.18-3.27 (m, 1 H), 2.71 (q, J=7.5 Hz, 2H), 2.35 (s, 3H), 2.05-2.14 (m, 2H), 1.82-1.94 (m, 4H), 1.68-1.80 (m, 2H), 1.29 (t, J=7.5 Hz, 3H) (formate salt); $^1$H NMR (CD$_3$OD): δ 8.51 (s, 1H), 7.89 (s, 1H), 7.87 (s, 1H), 7.55 (s, 1H), 7.30 (s, 1H), 4.29-4.37 (m, 1H), 4.01 (s, 3H), 3.83-4.00 (m, 4H), 3.72-3.83 (m, 2H), 3.47-3.55 (m, 1H), 3.22-3.30 (m, 3H), 2.82 (q, J=7.3 Hz, 2H), 2.43 (s, 3H), 2.06-2.17 (m, 2H), 1.85-1.98 (m, 4H), 1.70-1.84 (m, 2H), 1.33 (t, J=7.6 Hz, 3H) (formate salt).

Example 5

2-(4-(5-(2-Cyclopentyl-6-methoxypyridin-4-yl)-1,2,4-oxadiazol-3-yl)-2-ethyl-6-methylphenoxy)acetic acid To a solution of 4-[5-(2-cyclopentyl-6-methoxy-pyridin-4-yl)-[1,2,4]oxadiazol-3-yl]-2-ethyl-6-methyl-phenol (203 mg, 0.535 mmol) in DMF (5 mL), NaH (43 mg, 1.07 mmol, 60% in mineral oil) is added at 0° C. The mixture is stirred at 0° C. and ethyl bromoacetate (98 mg, 0.588 mmol) is added. Stirring is continued at 0° C. for 30 min, then at rt for 72 h. The reaction is quenched by adding water (2 mL) and the mixture is concentrated. The residue is dissolved in THF (10 mL), methanol (10 mL) and 2 N aq. LiOH (10 mL). The mixture is stirred at 60° C. for 2 h before it is cooled to rt, acidified by adding 2 N aq. HCl and extracted three times with EA (3×20 mL). The combined org. extracts are concentrated and the crude product is purified by prep. HPLC to give the title compound (146 mg) as a white solid; LC-MS: t$_R$=1.14 min, [M+H]$^+$=438.07; $^1$H NMR (CDCl$_3$): δ 7.90 (s, 1H), 7.88 (s, 1H), 7.79 (s br, 1H), 7.50 (s, 1H), 7.29 (s, 1H), 4.57 (s, 2H), 4.01 (s, 3H), 3.20-3.29 (m, 1H), 2.79 (q, J=7.5 Hz, 2H), 2.42 (s, 3H), 2.04-2.16 (m, 2H), 1.82-1.95 (m, 4H), 1.68-1.80 (m, 2H), 1.34 (t, J=7.5 Hz, 3H).

Example 6

4-(4-(5-(2-Cyclopentyl-6-methoxypyridin-4-yl)-1,2,4-oxadiazol-3-yl)-2-ethyl-6-methylphenoxy)butanoic acid The title compound (146 mg) is obtained as a white solid following the procedure given in Example 5 and starting from 4-[5-(2-cyclopentyl-6-methoxy-pyridin-4-yl)-[1,2,4]oxadiazol-3-yl]-2-ethyl-6-methyl-phenol (200 mg, 0.528 mmol) and ethyl 4-iodobutyrate (256 mg, 1.06 mmol); LC-MS: t$_R$=1.19 min, [M+H]$^+$=465.82; $^1$H NMR (CDCl$_3$): δ 7.87 (s, 1H), 7.86 (s, 1H), 7.51 (s, 1H), 7.30 (s, 1H), 4.02 (s, 3H), 3.90 (t, J=6.1 Hz, 2H), 3.19-3.30 (m, 1H), 2.70-2.78 (m, 4H), 2.38

(s, 3H), 2.21 (quint, J=6.5 Hz, 2H), 2.06-2.15 (m, 2H), 1.84-1.95 (m, 4H), 1.68-1.79 (m, 2H), 1.32 (t, J=7.5 Hz, 3H).

Example 7

2-((2-(4-(5-(2-Cyclopentyl-6-methoxypyridin-4-yl)-1,2,4-oxadiazol-3-yl)-2-ethyl-6-methylphenoxy)ethyl)amino)acetic acid The title compound (40 mg) is obtained as an off-white solid following the procedures given in Example 1 starting from 2-(4-(5-(2-cyclopentyl-6-methoxypyridin-4-yl)-1,2,4-oxadiazol-3-yl)-2-ethyl-6-methylphenoxy)ethyl methanesulfonate (200 mg, 0.399 mmol) and glycine ethyl ester hydrochloride (167 mg, 1.20 mmol); LC-MS: $t_R$=0.94 min, $[M+H]^+$=481.03; $^1$H NMR (CD$_3$OD): δ 7.92 (s, 1H), 7.90 (s, 1H), 7.55 (s, 1H), 7.31 (s, 1H), 4.13-4.18 (m, 2H), 4.02 (s, 3H), 3.66 (s, 2H), 3.49-3.55 (m, 3H), 2.82 (q, J=7.3 Hz, 2H), 2.45 (s, 3H), 2.08-2.17 (m, 2H), 1.86-1.98 (m, 4H), 1.73-1.82 (m, 2H), 1.35 (t, J=7.5 Hz, 3H).

Example 8 rac-1-(2-(4-(5-(2-Cyclopentyl-6-methoxypyridin-4-yl)-1,2,4-oxadiazol-3-yl)-2-ethyl-6-methylphenoxy)ethyl)pyrrolidine-3-carboxylic acid The title compound is obtained (68 mg) as a pale orange solid following the procedures given in Example 1 starting from 2-(4-(5-(2-cyclopentyl-6-methoxypyridin-4-yl)-1,2,4-oxadiazol-3-yl)-2-ethyl-6-methylphenoxy)ethyl methanesulfonate (250 mg, 0.498 mmol) and rac-methyl 3-pyrrolidine carboxylate hydrochloride (322 mg, 2.49 mmol); LC-MS: $t_R$=0.94 min, $[M+H]^+$=521.05; $^1$H NMR (CD$_3$OD): δ 8.25 (s, 1H), 7.92 (s, 1H), 7.90 (s, 1H), 7.54 (s, 1H), 4.20 (t, J=5.1 Hz, 2H), 4.01 (s, 3H), 3.79-3.85 (m, 1H), 3.50-3.77 (m, 5H), 3.21-3.31 (m, 2H), 2.82 (q, J=7.6 Hz, 2H), 2.45 (s, 3H), 2.30-2.44 (m, 2H), 2.07-2.16 (m, 2H), 1.87-1.97 (m, 4H), 1.73-1.82 (m, 2H), 1.35 (t, J=7.5 Hz, 3H).

Example 9

(S)-2-((3-(4-(5-(2-Cyclopentyl-6-methoxypyridin-4-yl)-1,2,4-oxadiazol-3-yl)-2-ethyl-6-methylphenoxy)-2-hydroxypropyl)amino)acetic acid a) A solution of (S)-5-(2-cyclopentyl-6-methoxypyridin-4-yl)-3-(3-ethyl-5-methyl-4-(oxiran-2-ylmethoxy)phenyl)-1,2,4-oxadiazole (500 mg, 1.15 mmol), glycine ethylester hydrochloride (320 mg, 2.30 mmol), of which the hydrochloride was removed by filtration over a carbonate loaded silica resin prior to use, and DIPEA (0.2 mL) in methanol (3 mL) is stirred at 60° C. for 3 days. The mixture is diluted with DCM and washed with sat. aq. NaHCO$_3$ solution. The aq. phase is extracted once with DCM. The combined org. extracts are dried over Na$_2$SO$_4$, filtered and concentrated. The crude product is purified by prep. TLC using DCM:methanol 9:1 to give (S)-2-((3-(4-(5-(2-cyclopentyl-6-methoxypyridin-4-yl)-1,2,4-oxadiazol-3-yl)-2-ethyl-6-methylphenoxy)-2-hydroxypropyl)amino)acetic acid ethyl ester (60 mg) as a white solid; LC-MS: $t_R$=1.03 min, $[M+H]^+$=537.29.

b) A solution of (S)-2-((3-(4-(5-(2-cyclopentyl-6-methoxypyridin-4-yl)-1,2,4-oxadiazol-3-yl)-2-ethyl-6-methylphenoxy)-2-hydroxypropyl)amino)acetic acid ethyl ester (60 mg, 0.114 mmol) in THF (3 mL), methanol (3 mL) and 2 N aq. LiOH (1 mL) is stirred at rt for 2 h. The solvent is evaporated and the residue is dissolved in 2 N aq. HCl (10 mL) and extracted four times with DCM (4×20 mL). The org. extracts are combined, dried over MgSO$_4$, filtered and concetrated. The crude product is purified by prep. HPLC to give the title compound (31 mg) as a white solid; LC-MS*: $t_R$=0.86 min, $[M+H]^+$=511.19; $^1$H NMR (CD$_3$OD): δ 7.88 (s, 1H), 7.86 (s, 1H), 7.54 (s, 1H), 7.30 (s, 1H), 4.30-4.36 (m, 1H), 4.01 (s, 3H), 3.87-3.98 (m, 2H), 3.63 (s, 2H), 3.46 (dd, $J_1$=12.5 Hz, $J_2$=2.9 Hz, 1H), 3.24-3.32 (m, 2H), 2.81 (q, J=7.6 Hz, 2H), 2.42 (s, 3H), 2.07-2.17 (m, 2H), 1.86-1.98 (m, 4H), 1.74-1.82 (m, 2H), 1.32 (t, J=7.6 Hz, 3H).

Example 10

(S)-3-(3-(4-(5-(2-Cyclopentyl-6-methoxypyridin-4-yl)-1,2,4-oxadiazol-3-yl)-2-ethyl-6-methylphenoxy)-2-hydroxypropyl)amino)propanoic acid The title compound is obtained (114 mg) as a white solid following the procedures given in Example 9 starting from (S)-5-(2-cyclopentyl-6-methoxypyridin-4-yl)-3-(3-ethyl-5-methyl-4-(oxiran-2-ylmethoxy)phenyl)-1,2,4-oxadiazole (1090 mg, 2.50 mmol) and β-alanine tert. butyl ester (682 mg, 3.75 mmol); LC-MS: $t_R$=0.95 min, $[M+H]^+$=525.15; $^1$H NMR (CDCl$_3$): δ 7.91 (s br, 3H), 7.75 (s, 1H), 7.71 (s, 1H), 7.40 (s, 1H), 7.17 (s, 1H), 4.46-4.59 (m, 1 H), 3.97 (s, 3H), 3.77-3.92 (m, 2H), 3.13-3.47 (m, 5H), 2.74-2.88 (m, 2H), 2.66 (q, J=7.3 Hz, 2H), 2.29 (s, 3H), 2.01-2.15 (m, 2H), 1.80-1.93 (m, 4H), 1.66-1.79 (m, 2H), 1.25 (t, J=7.5 Hz, 3H).

Example 11

(S)-2-((3-(4-(5-(2-Cyclopentyl-6-methoxypyridin-4-yl)-1,2,4-oxadiazol-3-yl)-2-ethyl-6-methylphenoxy)-2-hydroxypropyl)(methyl)amino)acetic acid The title compound is obtained (61 mg) as a pale brownish oil following the procedures given in Example 9 starting from (S)-5-(2-cyclopentyl-6-methoxypyridin-4-yl)-3-(3-ethyl-5-methyl-4-(oxiran-2-ylmethoxy)phenyl)-1,2,4-oxadiazole (300 mg, 0.689 mmol) and sarcosine methyl ester (184 mg, 2.07 mmol); LC-MS: $t_R$=0.95 min, $[M+H]^+$=525.04; $^1$H NMR (CDCl$_3$): δ 8.07 (s, 2H), 7.85 (s, 1H), 7.83 (s, 1H), 7.49 (s, 1H), 4.57-4.65 (m, 1H), 4.01 (s, 3H), 3.76-3.97 (m, 4H), 3.49-3.58 (m, 1H), 3.41-3.47 (m, 1H), 3.19-3.29 (m, 1H), 3.10 (s, 3H), 2.72 (q, J=7.8 Hz, 2H), 2.40 (s br, 2H), 2.37 (s, 3H), 2.05-2.16 (m, 2H), 1.83-1.94 (m, 4H), 1.69-1.79 (m, 2H), 1.31 (t, J=7.5 Hz, 3H) (formate salt).

Example 12

(S)-1-(3-(4-(5-(2-Cyclopentyl-6-methoxypyridin-4-yl)-1,2,4-oxadiazol-3-yl)-2-ethyl-6-methylphenoxy)-2-hydroxypropyl)azetidine-3-carboxylic acid The title compound is obtained (73 mg) as a pale brownish oil following the procedures given in Example 9 starting from (S)-5-(2-cyclopentyl-6-methoxypyridin-4-yl)-3-(3-ethyl-5-methyl-4-(oxiran-2-ylmethoxy)phenyl)-1,2,4-oxadiazole (200 mg, 0.459 mmol) and azetidine-3-carboxylic acid methyl ester (139 mg, 0.918 mmol); LC-MS: $t_R$=0.87 min, $[M+H]^+$=537.26; $^1$H NMR (CD$_3$OD): δ 8.18 (s, 2H), 7.89 (s, 1H), 7.87 (s, 1H), 7.55 (s, 1H), 7.31 (s, 1H), 4.32-4.43 (m, 4H), 4.21-4.28 (m, 1H), 4.02 (s, 3H), 3.88 (d, J=5.0 Hz, 2H), 3.42-3.64 (m, 4H), 2.81 (q, J=7.6 Hz, 2H), 2.42 (s, 3H), 2.07-2.17 (m, 2H), 1.87-1.97 (m, 4H), 1.73-1.83 (m, 2H), 1.33 (t, J=7.4 Hz, 3H) (formate salt).

Example 13

2-(4-(5-(2-Cyclopentyl-6-methoxypyridin-4-yl)-1,2,4-oxadiazol-3-yl)-2-ethyl-6-methylphenoxy)-N-(2-hydroxyethyl)acetamide To a solution of 2-(4-(5-(2-cyclopentyl-6-methoxypyridin-4-yl)-1,2,4-oxadiazol-3-yl)-2-ethyl-6-methylphenoxy)acetic acid (780 mg, 1.65 mmol) in THF (30 mL), HOBt (267 mg, 1.98 mmol) followed by EDC HCl (379 mg, 1.98 mmol) is added. The mixture is stirred at rt for 5 min before ethanolamine (121 mg, 1.98 mmol) is added. Stirring is continued for 3 h. The mixture is diluted with water and sat. aq. NaHCO$_3$ solution and extracted twice with EA. The combined org. extracts are dried over MgSO$_4$, filtered and concentrated. The crude product is purified by prep. HPLC to give the title compound (202 mg) as a colourless oil; LC-MS: $t_R$=1.07 min, [M+H]$^+$=481.01; $^1$H NMR (CDCl$_3$): δ 7.90 (s, 1H), 7.89 (s, 1H), 7.50 (d, J=0.5 Hz, 1H), 7.35 (t br, J=5.3 Hz, 1H), 7.30 (d, J=0.8 Hz, 1H), 4.39 (s, 2H), 4.02 (s, 3H), 3.87 (t, J=4.9 Hz, 2H), 3.63 (m, 2H), 3.51 (s, 2H), 3.20-3.29 (m, 1H), 2.73 (q, J=7.6 Hz, 2H), 2.38 (s, 3H), 2.06-2.15 (m, 2H), 1.84-1.95 (m, 4H), 1.70-1.80 (m, 2H), 1.33 (t, J=7.6 Hz, 3H).

Example 14

(S)-3-(3-(4-(5-(2-Cyclopentyl-6-methoxypyridin-4-yl)-1,2,4-oxadiazol-3-yl)-2-ethyl-6-methylphenoxy)-2-hydroxypropyl)amino)-3-oxopropanoic acid a) A solution of (S)-5-(2-cyclopentyl-6-methoxypyridin-4-yl)-3-(3-ethyl-5-methyl-4-(oxiran-2-ylmethoxy)phenyl)-1,2,4-oxadiazole (350 mg, 0.804 mmol) in 7 N NH$_3$ in methanol (15 mL) is stirred at 45° C. for 18 h. The solvent is evaporated and the crude product is purified by CC on silica gel eluting with DCM:7 N NH$_3$ in methanol 94:6 to give (S)-1-amino-3-(4-(5-(2-cyclopentyl-6-methoxypyridin-4-yl)-1,2,4-oxadiazol-3-yl)-2-ethyl-6-methylphenoxy)propan-2-ol (256 mg) as a pale yellow solid; LC-MS: $t_R$=0.83 min, [M+H]$^+$=453.22.

b) To a solution of mono-ethyl malonate (13 mg, 0.097 mmol) in DMF (1 mL), DIPEA (38 mg, 0.291 mmol) and TBTU (33 mg, 0.102 mmol) are added. The mixture is stirred at rt for 5 min before (S)-1-amino-3-(4-(5-(2-cyclopentyl-6-methoxypyridin-4-yl)-1,2,4-oxadiazol-3-yl)-2-ethyl-6-methylphenoxy)propan-2-ol (44 mg, 0.097 mmol) is added. Stirring is continued at rt for 2 h before the mixture is diluted with water and sat. aq. NaHCO$_3$ and extracted twice with EA. The combined org. extracts are dried over MgSO$_4$, filtered and concentrated to give crude (S)-ethyl 3-((3-(4-(5-(2-cyclopentyl-6-methoxypyridin-4-yl)-1,2,4-oxadiazol-3-yl)-2-ethyl-6-methylphenoxy)-2-hydroxypropyl)amino)-3-oxopropanoate (39 mg) as a yellow oil; LC-MS: $t_R$=1.03 min, [M+H]$^+$=567.11. This material is dissolved in methanol (5 mL) and 2 N aq. LiOH (5 mL) and the mixture is stirred at rt for 15 h. The reaction mixture is acidified by adding 2 N aq. HCl and then extracted with twice EA. The combined org. extracts are dried over MgSO$_4$, filtered and concentrated. The crude product is purified by prep. HPLC to give the title compound (23 mg) as a white solid; LC-MS: $t_R$=1.00 min, [M+H]$^+$=538.98; $^1$H NMR (CD$_3$OD): δ 7.86 (s, 1H), 7.84 (s, 1H), 7.53 (s, 1H), 7.29 (s, 1H), 4.10-4.19 (m, 1H), 4.01 (s, 3H), 3.83-3.93 (m, 2H), 3.62 (dd, J$_1$=13.7 Hz, J$_2$=4.8 Hz, 1H), 3.43 (dd, J$_1$=13.8 Hz, J$_2$=6.9 Hz, 1H), 3.24-3.32 (m, 2H), 2.80 (q, J=7.5 Hz, 2H), 2.41 (s, 3H), 2.06-2.18 (m, 2H), 1.85-1.97 (m, 4H), 1.73-1.82 (m, 2H), 1.31 (t, J=7.5 Hz, 3H).

Example 15

(S)-4-((3-(4-(5-(2-Cyclopentyl-6-methoxypyridin-4-yl)-1,2,4-oxadiazol-3-yl)-2-ethyl-6-methylphenoxy)-2-hydroxypropyl)amino)-4-oxobutanoic acid The title compound is obtained (162 mg) as a pale brownish oil following the procedures given in Example 14 starting from (S)-1-amino-3-(4-(5-(2-cyclopentyl-6-methoxypyridin-4-yl)-1,2,4-oxadiazol-3-yl)-2-ethyl-6-methylphenoxy)propan-2-ol (348 mg, 0.614 mmol) and mono-methyl succinate (128 mg, 0.921 mmol); LC-MS: $t_R$=1.05 min, [M+H]$^+$=553.20; $^1$H NMR (CD$_3$OD): δ 7.85 (s, 1H), 7.83 (s, 1H), 7.53 (s, 1H), 7.28 (s, 1H), 4.07-4.15 (m, 1H), 4.00 (s, 3H), 3.81-3.92 (m, 2H), 3.57 (dd, J$_1$=13.7 Hz, J$_2$=4.8 Hz, 1H), 3.34-3.42 (m, 1H), 3.23-3.31 (m, 1H), 2.80 (q, J=7.6 Hz, 2H), 2.64 (m, 2H), 2.51-2.58 (m, 2H), 2.41 (s, 3H), 2.07-2.17 (m, 2H), 1.85-1.98 (m, 4H), 1.72-1.82 (m, 2H), 1.31 (t, J=7.5 Hz, 3H).

Example 16

2-((2-(4-(5-(2-Cyclopentyl-6-methoxypyridin-4-yl)-1,2,4-oxadiazol-3-yl)-2-ethyl-6-methylphenoxy)ethyl)(methyl)amino)acetic acid The title compound is obtained (24 mg) as a beige solid following the procedures given in Example 1 starting from 2-(4-(5-(2-cyclopentyl-6-methoxypyridin-4-yl)-1,2,4-oxadiazol-3-yl)-2-ethyl-6-methylphenoxy)ethyl methanesulfonate (263 mg, 0.525 mmol) and sarcosine methyl ester hydrochloride (878 mg, 6.29 mmol); LC-MS: $t_R$=0.95 min, [M+H]$^+$=495.25; $^1$H NMR (CDCl$_3$): δ 7.77 (s, 1H), 7.73 (s, 1H), 7.41 (s, 1H), 7.18 (s, 1H), 3.95 (s, 3H), 3.88-3.95 (m, 2H), 3.47 (s br, 3H), 3.14-3.24 (m, 3H), 2.98 (s br, 2H), 2.68 (q, J=7.0 Hz, 2H), 2.47 (s, 3H), 2.31 (s, 3H), 2.02-2.11 (m, 2H), 1.79-1.93 (m, 4H), 1.67-1.77 (m, 2H), 1.26 (t, J=7.3 Hz, 3H).

Example 17

3-((2-(4-(5-(2-Cyclopentyl-6-methoxypyridin-4-yl)-1,2,4-oxadiazol-3-yl)-2-ethyl-6-methylphenoxy)ethyl)(methyl)amino)propanoic acid The title compound is obtained (7 mg) as a colourless glass following the procedures given in Example 1 starting from 2-(4-(5-(2-cyclopentyl-6-methoxypyridin-4-yl)-1,2,4-oxadiazol-3-yl)-2-ethyl-6-methylphenoxy)ethyl methanesulfonate (280 mg, 0.558 mmol) and ethyl 3-(methylamino)-propionate (148 mg, 1.13 mmol); LC-MS: $t_R$=0.94 min, [M+H]$^+$=509.26; $^1$H NMR (CD$_3$OD): δ 7.88 (s, 1H), 7.86 (s, 1H), 7.52 (s, 1H), 7.27 (s, 1H), 4.21 (t, J=5.0 Hz, 2H), 4.00 (s, 3H), 3.56 (t, J=5.0 Hz, 2H), 3.42 (t, J=6.5 Hz, 2H), 3.23-3.30 (m, 1H), 2.98 (s, 3H), 2.80 (q, J=7.5 Hz, 2H), 2.65 (t, J=6.5 Hz, 2H), 2.43 (s, 3H), 2.06-2.16 (m, 2H), 1.85-1.97 (m, 4H), 1.72-1.83 (m, 2H), 1.33 (t, J=7.5 Hz, 3H).

Example 18

2-((3-(4-(5-(2-Cyclopentyl-6-methoxypyridin-4-yl)-1,2,4-oxadiazol-3-yl)-2-ethyl-6-methylphenoxy)propyl)amino)acetic acid The title compound (59 mg) is prepared as a pale yellow solid in analogy to the procedures given in Example 1 starting from 3-(4-(5-(2-cyclopentyl-6-methoxypyridin-4-yl)-1,2,4-oxadiazol-3-yl)-2-ethyl-6-methylphenoxy)propyl methanesulfonate (150 mg, 0.291 mmol) and glycine ethyl ester hydrochloride (203 mg, 1.46 mmol); LC-MS: $t_R$=0.96 min, [M+H]$^+$=495.25; $^1$H NMR (CD$_3$OD): δ 7.88 (s, 1H), 7.86 (s, 1H), 7.53 (s, 1H), 7.28 (s, 1H), 3.98-4.03 (m, 2H), 4.00 (s, 3H), 3.84 (s, 2H), 3.38-3.44 (m, 2H), 3.24-3.31 (m, 1H), 2.78 (q, J=7.6 Hz, 2H), 2.41 (s, 3H), 2.23-2.32 (m, 2H), 2.06-2.17 (m, 2H), 1.85-1.97 (m, 4H), 1.72-1.82 (m, 2H), 1.32 (t, J=7.5 Hz, 3H).

Example 19

3-((3-(4-(5-(2-Cyclopentyl-6-methoxypyridin-4-yl)-1,2,4-oxadiazol-3-yl)-2-ethyl-6-methylphenoxy)propyl)amino)propanoic acid The title compound (6 mg) is prepared as a pale brownish solid in analogy to the procedures given in Example 1 starting from 3-(4-(5-(2-cyclopentyl-6-methoxypyridin-4-yl)-1,2,4-oxadiazol-3-yl)-2-ethyl-6-methylphenoxy)propyl methanesulfonate (100 mg, 0.194 mmol) and β-alanine ethyl ester hydrochloride (149 mg, 0.970 mmol); LC-MS: $t_R$=0.96 min, [M+H]$^+$=509.28; $^1$H NMR (CD$_3$OD): δ 7.88 (s, 1H), 7.87 (s, 1H), 7.57 (s, 1H), 7.35 (s, 1H), 4.04 (s, 3H), 4.01 (t, J=6.0 Hz, 2H), 3.36-3.46 (m, 4H), 3.23-3.32 (m, 1H), 2.84 (t, J=6.4 Hz, 2H), 2.79 (q, J=7.6 Hz, 2H), 2.42 (s, 3H), 2.25-2.34 (m, 2H), 2.07-2.19 (m, 2H), 1.85-1.97 (m, 4H), 1.73-1.83 (m, 2H), 1.33 (t, J=7.5 Hz, 3H).

Example 20

2-((3-(4-(5-(2-Cyclopentyl-6-methoxypyridin-4-yl)-1,2,4-oxadiazol-3-yl)-2-ethyl-6-methylphenoxy)propyl)(methyl)amino)acetic acid The title compound (102 mg) is prepared as a pale yellow oil in analogy to the procedures given in Example 1 starting from 3-(4-(5-(2-cyclopentyl-6-methoxypyridin-4-yl)-1,2,4-oxadiazol-3-yl)-2-ethyl-6-methylphenoxy)propyl methanesulfonate (150 mg, 0.291 mmol) and sarcosine methyl ester hydrochloride (203 mg, 1.46 mmol); LC-MS: $t_R$=0.97 min, [M+H]$^+$=509.26; $^1$H NMR (CD$_3$OD): δ 7.85 (s, 1H), 7.83 (s, 1H), 7.51 (s, 1H), 7.25 (s, 1H), 3.99 (s, 3H), 3.98 (t, J=5.9 Hz, 2H), 3.79 (s, 2H), 3.50-3.58 (m, 2H), 3.22-3.30 (m, 1H), 3.02 (s, 3H), 2.76 (q, J=7.5 Hz, 2H), 2.39 (s, 3H), 2.28-2.37 (m, 2H), 2.04-2.16 (m, 2H), 1.84-1.97 (m, 4H), 1.71-1.82 (m, 2H), 1.31 (t, J=7.5 Hz, 3H).

Example 21

3-((3-(4-(5-(2-Cyclopentyl-6-methoxypyridin-4-yl)-1,2,4-oxadiazol-3-yl)-2-ethyl-6-methylphenoxy)propyl)(methyl)amino)propanoic acid The title compound (46 mg) is prepared as a pale yellow oil in analogy to the procedures given in Example 1 starting from 3-(4-(5-(2-cyclopentyl-6-methoxypyridin-4-yl)-1,2,4-oxadiazol-3-yl)-2-ethyl-6-methylphenoxy)propyl methanesulfonate (150 mg, 0.291 mmol) and ethyl 3-(methylamino)propanoate (244 mg, 1.46 mmol); LC-MS: $t_R$=0.97 min, [M+H]$^+$=523.26; $^1$H NMR (CD$_3$OD): δ 7.87 (s, 1H), 7.85 (s, 1H), 7.54 (s, 1H), 7.31 (s, 1H), 4.02 (s, 3H), 3.96-4.01 (m, 2H), 3.57-3.73 (m, 2H), 3.48-3.56 (m, 1H), 3.39-3.48 (m, 1H), 3.23-3.31 (m, 1H), 3.01 (s, 3H), 2.94 (t, J=6.7 Hz, 2H), 2.78 (q, J=7.5 Hz, 2H), 2.41 (s, 3H), 2.30-2.39 (m, 2H), 2.07-2.19 (m, 2H), 1.84-1.96 (m, 4H), 1.72-1.83 (m, 2H), 1.32 (t, J=7.5 Hz, 3H).

Example 22

1-(3-(4-(5-(2-Cyclopentyl-6-methoxypyridin-4-yl)-1,2,4-oxadiazol-3-yl)-2-ethyl-6-methylphenoxy)propyl)azetidine-3-carboxylic acid The title compound (29 mg) is prepared as a white solid in analogy to the procedures given in Example 1 starting from 3-(4-(5-(2-cyclopentyl-6-methoxypyridin-4-yl)-1,2,4-oxadiazol-3-yl)-2-ethyl-6-methylphenoxy)propyl methanesulfonate (150 mg, 0.291 mmol) and azetidine-3-carboxylic acid methyl ester hydrochloride (220 mg, 1.46 mmol); LC-MS: $t_R$=0.96 min, [M+H]$^+$=521.39; $^1$H NMR (CD$_3$OD): δ 7.89 (d, J=1.4 Hz, 1H), 7.87 (d, J=1.4 Hz, 1H), 7.55 (d, J=1.0 Hz, 1H), 7.31 (d, J=1.1 Hz, 1H), 4.24-4.40 (m, 4H), 4.01 (s, 3H), 3.97 (t, J=5.8 Hz, 2H), 3.53-3.60 (m, 2H), 3.43-3.48 (m, 1H), 3.26-3.31 (m, 1H), 2.78 (q, J=7.5 Hz, 2H), 2.41 (s, 3H), 2.06-2.19 (m, 4H), 1.86-1.97 (m, 4H), 1.72-1.83 (m, 2H), 1.33 (t, J=7.5 Hz, 3H).

Example 23

2-((2-(4-(5-(2-Cyclopentyl-6-methoxypyridin-4-yl)-1,2,4-oxadiazol-3-yl)-2-ethyl-6-methylphenoxy)ethyl)amino)ethanol A mixture of 2-(4-(5-(2-cyclopentyl-6-methoxypyridin-4-yl)-1,2,4-oxadiazol-3-yl)-2-ethyl-6-methylphenoxy)ethyl methanesulfonate (184 mg, 0.367 mmol) and ethanolamine (112 mg, 1.83 mmol) in acetonitrile (6 mL) is stirred at 65° C. for 18 h before it is separated by prep. HPLC to give the title compound (77 mg) as a white solid; LC-MS: $t_R$=0.92 min, [M+H]$^+$=467.25; $^1$H NMR (CD$_3$OD): δ 7.91 (s, 1H), 7.88 (s, 1H), 7.62 (s, 1H), 7.41 (s, 1H), 4.20 (t, J=5.0 Hz, 2H), 4.07 (s, 3H), 3.93 (t, J=5.1 Hz, 2H), 3.60 (t, J=4.9 Hz, 2H), 3.34-3.38 (m, 2H), 3.24-3.31 (m, 1H), 2.82 (q, J=7.5 Hz, 2H), 2.45 (s, 3H), 2.10-2.19 (m, 2H), 1.85-1.97 (m, 4H), 1.72-1.84 (m, 2H), 1.35 (t, J=7.5 Hz, 3H).

Example 24

2-((3-(4-(5-(2-Cyclopentyl-6-methoxypyridin-4-yl)-1,2,4-oxadiazol-3-yl)-2-ethyl-6-methylphenoxy)propyl)amino)ethanol The title compound (54 mg) is obtained as a pale yellow solid in analogy to Example 23 starting from 3-(4-(5-(2-cyclopentyl-6-methoxypyridin-4-yl)-1,2,4-oxadiazol-3-yl)-2-ethyl-6-methylphenoxy)propyl methanesulfonate (200 mg, 0.388 mmol) and ethanolamine (72 mg, 1.16 mmol); LC-MS: $t_R$=0.95 min, [M+H]$^+$=481.10; $^1$H NMR (CD$_3$OD): 7.92 (s, 1H), 7.91 (s, 1H), 7.89 (s, 1H), 7.81 (s, 1H), 4.27 (s, 3H), 4.02 (t, J=5.9 Hz, 2H), 3.87 (m, 2H), 3.38-3.46 (m, 2H), 3.34-3.38 (m, 1H), 3.23-3.28 (m, 2H), 2.79 (q, J=7.5 Hz, 2H), 2.42 (s, 3H), 2.19-2.34 (m, 4H), 1.80-2.02 (m, 6H), 1.33 (t, J=7.5 Hz, 3H).

Example 25

2-((2-(4-(5-(2-Cyclopentyl-6-methoxypyridin-4-yl)-1,2,4-oxadiazol-3-yl)-2-ethyl-6-methylphenoxy)ethyl)amino)propane-1,3-diol The title compound (66 mg) is obtained as a white solid in analogy to Example 23 starting from 2-(4-(5-(2-cyclopentyl- 6-methoxypyridin-4-yl)-1,2,4-oxadiazol-3-yl)-2-ethyl-6-methylphenoxy)ethyl methanesulfonate (227 mg, 0.453 mmol) and serinol (165 mg, 1.81 mmol); LC-MS: $t_R$=0.91 min, [M+H]$^+$=497.11; $^1$H NMR (CD$_3$OD): δ 7.80 (s, 1H), 7.78 (s, 1H), 7.46 (s, 1H), 7.20 (s, 1H), 4.00 (t, J=5.2 Hz, 2H), 3.97 (s, 3H), 3.71 (dd, J$_1$=11.1 Hz, J$_2$=5.3 Hz, 2H), 3.62 (dd, J$_1$=11.0 Hz, H$_2$=6.0 Hz, 2H), 3.19-3.29 (m, 1H), 3.14 (t, J=5.2 Hz, 2H), 2.85 (quint, J=5.6 Hz, 1H), 2.77 (q, J=7.5 Hz, 2H), 2.38 (s, 3H), 2.04-2.16 (m, 2H), 1.83-1.95 (m, 4H), 1.70-1.81 (m, 2H), 1.30 (t, J=7.5 Hz, 3H).

Example 26

2-((3-(4-(5-(2-Cyclopentyl-6-methoxypyridin-4-yl)-1,2,4-oxadiazol-3-yl)-2-ethyl-6-methylphenoxy) propyl)amino)propane-1,3-diol The title compound (54 mg) is obtained as a pale brownish oil in analogy to Example 23 starting from 3-(4-(5-(2-cyclopentyl-6-methoxypyridin-4-yl)-1,2,4-oxadiazol-3-yl)-2-ethyl-6-methylphenoxy)propyl methanesulfonate (200 mg, 0.388 mmol) and serinol (106 mg, 1.16 mmol); LC-MS: $t_R$=0.93 min, [M+H]$^+$=511.28; $^1$H NMR (D$_6$-DMSO): δ 7.79 (s, 2H), 7.54 (s, 1H), 7.27 (s, 1H), 4.38-4.45 (m, 2H), 3.94 (s, 3H), 3.88 (t, J=6.1 Hz, 2H), 3.36-3.45 (m, 2H), 3.23-3.33 (m, 1H), 2.81 (t, J=6.7 Hz, 2H), 2.71 (q, J=7.5 Hz, 2H), 2.52-2.58 (m, 1H), 2.34 (s, 3H), 1.98-2.10 (m, 2H), 1.86-1.94 (m, 2H), 1.76-1.85 (m, 4H), 1.63-1.73 (m, 2H), 1.23 (t, J=7.5 Hz, 3H).

Example 27 rac-3-((2-(4-(5-(2-Cyclopentyl-6-methoxypyridin-4-yl)-1,2,4-oxadiazol-3-yl)-2-ethyl-6-methylphenoxy) ethyl)amino)propane-1,2-diol A mixture of 2-(4-(5-(2-cyclopentyl-6-methoxypyridin-4-yl)-1,2,4-oxadiazol-3-yl)-2-ethyl-6-methylphenoxy)ethyl methanesulfonate (195 mg, 0.389 mmol) and rac-2,2-dimethyl-1,3-dioxolane-4-methanamine (51 mg, 0.389 mmol) in acetonitrile (6 mL) is stirred at 65° C. for 16 h. The mixture is separated by prep. HPLC to give rac-2-(4-(5-(2-cyclopentyl-6-methoxypyridin-4-yl)-1,2,4-oxadiazol-3-yl)-2-ethyl-6-methylphenoxy)-N-((2,2-dimethyl-1,3-dioxolan-4-yl)methyl)ethanamine (180 mg) as a white solid. This material is dissolved in 2 N aq. HCl (1 mL) and dioxane (5 mL) and stirred at 60° C. for 1 h. The solvent is evaporated and the crude product is purified by prep. TLC eluting with DCM containing 15% of methanol followed by prep. HPLC to give the title compound (16 mg) as a white solid; LC-MS: $t_R$=0.91 min, [M+H]$^+$=497.11; $^1$H NMR (CD$_3$OD): δ 7.82 (s, 1H), 7.80 (s, 1H), 7.48 (s, 1H), 7.22 (s, 1H), 4.00 (t, J=5.0 Hz, 2H), 3.98 (s, 3H), 3.82-3.89 (m, 1H), 3.53-3.63 (m, 2H), 3.20-3.30 (m, 1H), 3.08 (t, J=5.0 Hz, 2H), 2.88 (dd, J$_1$=12.1 Hz, J$_2$=3.7 Hz, 1H), 2.70-2.81 (m, 3H), 2.38 (s, 3H), 2.05-2.15 (m, 2H), 1.84-1.95 (m, 4H), 1.69-1.81 (m, 2H), 1.30 (t, J=7.5 Hz, 3H).

Example 28 rac-3-((3-(4-(5-(2-Cyclopentyl-6-methoxypyridin-4-yl)-1,2,4-oxadiazol-3-yl)-2-ethyl-6-methylphenoxy) propyl)amino)propane-1,2-diol The title compound (94 mg) is obtained as a pale brownish oil in analogy to Example 27 starting from 3-(4-(5-(2-cyclopentyl-6-methoxypyridin-4-yl)-1,2,4-oxadiazol-3-yl)-2-ethyl-6-methylphenoxy)propyl methanesulfonate (200 mg, 0.388 mmol) and rac-2,2-dimethyl-1,3-dioxolane-4-methanamine (153 mg, 1.16 mmol); LC-MS: $t_R$=0.93 min, [M+H]$^+$=511.28; $^1$H NMR (D$_6$-DMSO): δ 7.80 (s, 2H), 7.55 (s, 1H), 7.28 (s, 1H), 4.55 (d br, J=4.0 Hz, 1H), 3.95 (s, 3H), 3.88 (t, J=6.1 Hz, 2H), 3.50-3.58 (m, 1H), 3.24-3.32 (m, 2H), 2.67-2.79 (m, 4H), 2.63 (dd, J$_1$=11.7 Hz, J$_2$=4.5 Hz, 1H), 2.47 (dd, J$_1$=11.8 Hz, J$_2$=7.0 Hz, 1H), 2.34 (s, 3H), 1.99-2.08 (m, 2H), 1.87-1.95 (m, 2H), 1.76-1.87 (m, 4H), 1.64-1.73 (m, 2H), 1.23 (t, J=7.5 Hz, 3H).

Example 29

N-(3-(4-(5-(2-Cyclopentyl-6-methoxypyridin-4-yl)-1,2,4-oxadiazol-3-yl)-2-ethyl-6-methylphenoxy) propyl)-2-hydroxyacetamide a) A solution of 3-(4-(5-(2-cyclopentyl-6-methoxypyridin-4-yl)-1,2,4-oxadiazol-3-yl)-2-ethyl-6-methylphenoxy)propyl methanesulfonate (1.30 g, 2.52 mmol) in 7 N NH$_3$ in methanol (30 mL) is stirred at 55° C. for 24 h. The mixture is concentrated and dried to give crude 3-(4-(5-(2-cyclopentyl-6-methoxypyridin-4-yl)-1,2,4-oxadiazol-3-yl)-2-ethyl-6-methylphenoxy)propan-1-amine (1.24 g) as a pale yellow foam; LC-MS: $t_R$=0.95 min, [M+H]$^+$=437.33.

b) To a solution of 3-(4-(5-(2-cyclopentyl-6-methoxypyridin-4-yl)-1,2,4-oxadiazol-3-yl)-2-ethyl-6-methylphenoxy)propan-1-amine (200 mg, 0.458 mmol), glycolic acid (52 mg, 0.687 mmol) and DIPEA (178 mg, 1.37 mmol) in DMF (5 mL), TBTU (191 mg, 0.596 mmol) is added. The mixture is stirred at rt for 18 h before it is diluted with EA (50 mL) and washed twice with sat. aq. NaHCO$_3$ solution (50 mL) followed by brine (50 mL). The org. extract is dried over Na$_2$SO$_4$, filtered, and concentrated. The crude product is purified by prep. HPLC to give the title compound (116 mg) as a pale yellow oil; LC-MS: $t_R$=1.14 min, [M+H]$^+$=495.25; $^1$H NMR (CD$_3$OD): δ 7.85 (s, 1H), 7.83 (s, 1H), 7.53 (s, 1H), 7.28 (s, 1H), 4.01 (s, 2H), 4.00 (s, 3H), 3.94 (t, J=6.1 Hz, 2H), 3.57 (t, J=6.9 Hz, 2H), 3.24-3.31 (m, 1H), 2.77 (q, J=7.6 Hz, 2H), 2.38 (s, 3H), 2.05-2.16 (m, 4H), 1.86-1.96 (m, 4H), 1.72-1.82 (m, 2H), 1.31 (t, J=7.5 Hz, 3H).

Example 30

N-(3-(4-(5-(2-Cyclopentyl-6-methoxypyridin-4-yl)-1,2,4-oxadiazol-3-yl)-2-ethyl-6-methylphenoxy) propyl)-2-hydroxy-N-methylacetamide a) 3-(4-(5-(2-Cyclopentyl-6-methoxypyridin-4-yl)-1,2,4-oxadiazol-3-yl)-2-ethyl-6-methylphenoxy)-N-methylpropan-1-amine (941 mg) is prepared in analogy to Example 29 starting from 3-(4-(5-(2-cyclopentyl-6-methoxypyridin-4-yl)-1,2,4-oxadiazol-3-yl)-2-ethyl-6-methylphenoxy)propyl methanesulfonate (700 mg, 1.36 mmol) and 2 M methyl amine solution in THF (20 mL); LC-MS: $t_R$=0.96 min, [M+H]$^+$=451.29.

b) The title compound (155 mg) is obtained as a pale yellow oil in analogy to Example 29 starting from 3-(4-(5-(2-cyclopentyl-6-methoxypyridin-4-yl)-1,2,4-oxadiazol-3-yl)-2-ethyl-6-methylphenoxy)-N-methylpropan-1-amine (206 mg, 0.458 mmol) and glycolic acid (52 mg, 0.687 mmol); LC-MS: $t_R$=1.19 min, [M+H]$^+$=509.40; $^1$H NMR (CD$_3$OD): δ 7.84-7.86 (m, 1H), 7.81-7.84 (m, 1H), 7.51-7.53 (m, 1H), 7.26-7.28 (m, 1H), 4.35 (s, 0.7; H), 4.25 (s, 1.3 H), 4.00 (s, 3H), 3.91 (q, J=5.8 Hz, 2H), 3.69 (m, 1.3; H), 3.55-3.61 (m, 0.7; H), 3.24-3.31 (m, 1H), 3.06 (s, 1.05; H), 3.04 (s, 1.95; H), 2.72-2.79 (m, 2H), 2.38 (s, 3H), 2.07-2.19 (m, 4H), 1.85-1.96 (m, 4H), 1.71-1.83 (m, 2H), 1.28-1.35 (m, 3H) (1:2 mixture of atropisomers).

Example 31

3-((3-(4-(5-(2-Cyclopentyl-6-methoxypyridin-4-yl)-1,2,4-oxadiazol-3-yl)-2-ethyl-6-methylphenoxy) propyl)amino)-3-oxopropanoic acid To a solution of 3-(4-(5-(2-cyclopentyl-6-methoxypyridin-4-yl)-1,2,4-oxadiazol-3-yl)-2-ethyl-6-methylphenoxy)propan-1-amine (200 mg, 0.458 mmol), monoethylmalonate (91 mg, 0.687 mmol) and DIPEA (178 mg, 1.37 mmol) in DMF (5 mL) is added TBTU (191 mg, 0.596 mmol). The mixture is stirred at rt for 18 h. The solution is diluted with EA (50 mL) and washed twice with sat aq. NaHCO$_3$ solution (50 mL) followed by brine (50 mL). The org. extract is dried over Na$_2$SO$_4$, filtered and concentrated to give crude ethyl 3-((3-(4-(5-(2-cyclopentyl-6-methoxypyridin-4-yl)-1,2,4-oxadiazol-3-yl)-2-ethyl-6-methylphenoxy) propyl)amino)-3-oxopropanoate (298 mg) as a yellow oil; LC-MS: t$_R$=1.19 min, [M+H]$^+$=551.38. This material is dissolved in methanol (2 mL), THF (2 mL) and 2 N aq. LiOH (1 mL). The solution is stirred at rt for 2 h before it is concentrated, diluted with DCM (20 mL) and washed with 2 N aq. HCl (10 mL). The aq. phase is extracted three times with DCM (3×20 mL). The combined org. extracts are dried over MgSO$_4$, filtered and concentrated. The crude product is purified by prep. HPLC to give the title compound (105 mg) as a white solid; LC-MS: t$_R$=1.14 min, [M+H]$^+$=523.21; $^1$H NMR (CD$_3$OD): δ 7.82 (s, 1H), 7.79 (s, 1H), 7.49 (s, 1H), 7.23 (s, 1H), 3.99 (s, 3H), 3.92 (t, J=6.2 Hz, 2H), 3.52 (t, J=6.9 Hz, 2H), 3.31 (s, 2H), 3.22-3.31 (m, 1H), 2.75 (q, J=7.5 Hz, 2H), 2.36 (s, 3H), 2.04-2.15 (m, 4H), 1.85-1.95 (m, 4H), 1.73-1.82 (m, 2H), 1.29 (t, J=7.5 Hz, 3H).

Example 32

4-((3-(4-(5-(2-Cyclopentyl-6-methoxypyridin-4-yl)-1,2,4-oxadiazol-3-yl)-2-ethyl-6-methylphenoxy) propyl)amino)-4-oxobutanoic acid The title compound (106 mg) is obtained as a white solid in analogy to Example 31 starting from 3-(4-(5-(2-cyclopentyl-6-methoxypyridin-4-yl)-1,2,4-oxadiazol-3-yl)-2-ethyl-6-methylphenoxy)propan-1-amine (200 mg, 0.458 mmol) and mono methyl succinate (96 mg, 0.687 mmol); LC-MS: t$_R$=1.13 min, [M+H]$^+$=537.22; $^1$H NMR (CD$_3$OD): δ 7.81 (s, 1H), 7.79 (s, 1H), 7.48 (s, 1H), 7.22 (s, 1H), 3.98 (s, 3H), 3.90 (t, J=6.2 Hz, 2H), 3.47 (t, J=7.0 Hz, 2H), 3.21-3.30 (m, 1H), 2.74 (q, J=7.5 Hz, 2H), 2.63 (t, J=7.0 Hz, 2H), 2.51 (t, J=6.7 Hz, 2H), 2.36 (s, 3H), 2.02-2.14 (m, 4H), 1.83-1.95 (m, 4H), 1.71-1.80 (m, 2H), 1.29 (t, J=7.5 Hz, 3H).

Example 33

3-((3-(4-(5-(2-Cyclopentyl-6-methoxypyridin-4-yl)-1,2,4-oxadiazol-3-yl)-2-ethyl-6-methylphenoxy) propyl)(methyl)amino)-3-oxopropanoic acid The title compound (103 mg) is obtained as a pale yellow oil in analogy to Example 31 starting from 3-(4-(5-(2-cyclopentyl-6-methoxypyridin-4-yl)-1,2,4-oxadiazol-3-yl)-2-ethyl-6-methylphenoxy)-N-methylpropan-1-amine (206 mg, 0.458 mmol) and monoethylmalonate (91 mg, 0.687 mmol); LC-MS: t$_R$=1.16 min, [M+H]$^+$=537.37; $^1$H NMR (CD$_3$OD): δ 7.81-7.84 (m, 1H), 7.78-7.81 (m, 1H), 7.49-7.50 (m, 1H), 7.23-7.24 (m, 1H), 3.99 (s, 3H), 3.88-3.95 (m, 2H), 3.66-3.74 (m, 2H), 3.59-3.62 (m, 0.3; H), 3.52-3.54 (m, 0.7; H), 3.23-3.30 (m, 1H), 3.16 (s, 2.1; H), 3.05 (s, 0.9; H), 2.75 (q, J=7.5 Hz, 2H), 2.37 (s, 0.9; H), 2.36 (s, 2.1; H), 2.06-2.22 (m, 4H), 1.84-1.95 (m, 4H), 1.73-1.81 (m, 2H), 1.26-1.33 (m, 3H) (mixture of atropisomers).

Example 34

4-((3-(4-(5-(2-Cyclopentyl-6-methoxypyridin-4-yl)-1,2,4-oxadiazol-3-yl)-2-ethyl-6-methylphenoxy) propyl)(methyl)amino)-4-oxobutanoic acid The title compound (168 mg) is obtained as a pale yellow oil in analogy to Example 31 starting from 3-(4-(5-(2-cyclopentyl-6-methoxypyridin-4-yl)-1,2,4-oxadiazol-3-yl)-2-ethyl-6-methylphenoxy)-N-methylpropan-1-amine (206 mg, 0.458 mmol) and mono methyl succinate (96 mg, 0.687 mmol); LC-MS: t$_R$=1.16 min, [M+H]$^+$=551.37; $^1$H NMR (CD$_3$OD): δ 7.80-7.83 (m, 1H), 7.77-7.80 (m, 1H), 7.47-7.49 (m, 1H), 7.22-7.24 (m, 1H), 3.98 (s, 3H), 3.94 (t, J=5.9 Hz, 0.8; H), 3.87 (t, J=6.4 Hz, 1.2; H), 3.70-3.75 (m, 0.8; H), 3.63-3.68 (m, 1.2; H), 3.21-3.30 (m, 1H), 3.16 (s, 2H), 3.01 (s, 1H), 2.60-2.80 (m, 6H), 2.37 (s, 1.2; H), 2.35 (s, 1.8; H), 2.06-2.23 (m, 4H), 1.84-1.96 (m, 4H), 1.71-1.82 (m, 2H), 1.26-1.33 (m, 3H).

Example 35

4-(2-Chloro-4-(5-(2-cyclopentyl-6-methoxypyridin-4-yl)-1,2,4-oxadiazol-3-yl)-6-methoxyphenoxy)butanoic acid a) 2-Chloro-4-(5-(2-cyclopentyl-6-methoxypyridin-4-yl)-1,2,4-oxadiazol-3-yl)-6-methoxyphenol (900 mg) is obtained as a white solid in analog to Example 1 step a) starting from 2-cyclopentyl-6-methoxy-isonicotinic acid (3.00 g, 13.6 mmol) and 3-chloro-4,N-dihydroxy-5-methoxy-benzamidine (3.08 g, 14.24 mmol); LC-MS: t$_R$=1.18 min, [M+H]$^+$=401.98.

b) The title compound (182 mg) is obtained as a colourless oil in analogy to Example 6 starting from 2-chloro-4-(5-(2-cyclopentyl-6-methoxypyridin-4-yl)-1,2,4-oxadiazol-3-yl)-6-methoxyphenol (225 mg, 0.56 mmol) and ethyl-4-bromobutyrate (169 mg, 0.84 mmol); LC-MS: t$_R$=1.12 min, [M+H]$^+$=488.17; $^1$H NMR (CDCl$_3$): δ 7.86 (d, J=1.9 Hz, 1H), 7.62 (d, J=1.8 Hz, 1H), 7.50 (d, J=0.8 Hz, 1H), 7.30 (d, J=0.9 Hz, 1H), 4.17 (t, J=5.9 Hz, 2H), 4.02 (s, 3H), 3.99 (s, 3H), 3.20-3.29 (m, 1H), 2.78 (t, J=7.3 Hz, 2H), 2.06-2.21 (m, 4H), 1.84-1.95 (m, 4H), 1.69-1.79 (m, 2H).

Example 36

4-(2-Chloro-4-(5-(2-cyclopentyl-6-methoxypyridin-4-yl)-1,2,4-oxadiazol-3-yl)-6-methoxyphenoxy)-N-(2-hydroxyethyl)butanamide The title compound (51 mg) is obtained as a colourless oil in analogy to Example 13 starting from 4-(2-chloro-4-(5-(2-cyclopentyl-6-methoxypyridin-4-yl)-1,2,4-oxadiazol-3-yl)-6-methoxyphenoxy)butanoic acid (75 mg, 0.154 mmol) and ethanolamine (11 mg, 0.184 mmol); LC-MS: t$_R$=1.06 min, [M+H]$^+$=531.15; $^1$H NMR (CDCl$_3$): δ 7.86 (d, J=1.8 Hz, 1H), 7.62 (d, J=1.8 Hz, 1H), 7.49 (s, 1H), 7.30 (s, 1H), 6.23 (s br, 1H), 4.17 (t, J=5.7 Hz, 2H), 4.02 (s, 3H), 3.99 (s, 3H), 3.76 (t, J=4.8 Hz, 2H), 3.48 (q, J=5.4 Hz, 2H), 3.19-3.29 (m, 1H), 2.60 (t, J=7.2 Hz, 2H), 2.14-2.22 (m, 2H), 2.06-2.15 (m, 2H), 1.84-1.95 (m, 4H), 1.69-1.80 (m, 2H).

Example 37

3-((2-(2-Chloro-4-(5-(2-cyclopentyl-6-methoxypyridin-4-yl)-1,2,4-oxadiazol-3-yl)-6-methoxyphenoxy)ethyl)amino)propanoic acid The title compound is prepared in analogy to Example 1 starting from 2-chloro-4-(5-(2-cyclopentyl-6-methoxypyridin-4-yl)-1,2,4-oxadiazol-3-yl)-6-methoxyphenol; LC-MS: $t_R$=0.86 min, [M+H]$^+$=517.17.

Example 38

N-(3-(2-Chloro-4-(5-(2-cyclopentyl-6-methoxypyridin-4-yl)-1,2,4-oxadiazol-3-yl)-6-methoxyphenoxy)propyl)-2-hydroxyacetamide The title compound is prepared in analgoy to Example 29 starting from 2-chloro-4-(5-(2-cyclopentyl-6-methoxypyridin-4-yl)-1,2,4-oxadiazol-3-yl)-6-methoxyphenol; LC-MS: $t_R$=1.08 min, [M+H]$^+$=517.19; $^1$H NMR (CDCl$_3$): δ 7.88 (d, J=1.7 Hz, 1H), 7.64 (d, J=1.7 Hz, 1H), 7.50 (s, 1H), 7.31 (s, 1H), 7.02 (s br, 1H), 4.19 (t, J=5.6 Hz, 2H), 4.16 (s, 2H), 4.02 (s, 3H), 4.01 (s, 3H), 3.70 (q, J=6.1 Hz, 2H), 3.20-3.29 (m, 1H), 2.03-2.16 (m, 4H), 1.84-1.95 (m, 4H), 1.70-1.80 (m, 2H).

Example 39

4-((2-(4-(5-(2-Cyclopentyl-6-methoxypyridin-4-yl)-1,2,4-oxadiazol-3-yl)-2-ethyl-6-methylphenoxy)ethyl)amino)butanoic acid The title compound (88 mg) is obtained as beige solid in analogy to Example 1 starting from 2-(4-(5-(2-cyclopentyl-6-methoxypyridin-4-yl)-1,2,4-oxadiazol-3-yl)-2-ethyl-6-methyl-phenoxy)ethyl methanesulfonate (292 mg, 0.582 mmol) and tert.-butyl γ-amino butyrate hydrochloride (263 mg, 1.34 mmol); LC-MS: $t_R$=0.93 min, [M+H]$^+$=509.27; $^1$H NMR (D$_6$-DMSO): δ 7.79 (s, 2H), 7.53 (s, 1H), 7.26 (s, 1H), 4.04 (s br, 2H), 3.94 (s, 3H), 3.90 (t, J=5.4 Hz, 2H), 3.23-3.33 (m, 1H), 2.99 (t, J=5.4 Hz, 2H), 2.66-2.77 (m, 4H), 2.35 (s, 3 H), 2.30 (t, J=7.0 Hz, 2H), 1.99-2.09 (m, 2H), 1.75-1.88 (m, 4H), 1.62-1.73 (m, 4H), 1.23 (t, J=7.5 Hz, 3H).

Example 40

4-(2-Chloro-4-(5-(2-cyclopentyl-6-methoxypyridin-4-yl)-1,2,4-oxadiazol-3-yl)-6-methylphenoxy)butanoic acid a) A mixture of 3-chloro-4-hydroxy-5-methyl-benzonitrile (1.15 g, 6.87 mmol) and Cs$_2$CO$_3$ (13.43 g, 41.2 mmol) in DMF (45 mL) is stirred at rt for 30 min before tert.-butyl 4-bromobutanoate (1.55 g, 6.95 mmol) is added. The orange suspension is stirred at 65° C. for 72 h. Another portion of tert.-butyl 4-bromobutanoate (1.55 g, 6.95 mmol) is added and stirring is continued at 65° C. for 24 h. The mixture is diluted with water (150 mL) and extracted three times with DCM (3×50 mL) and EA (3×50 mL). The org. extracts are combined, dried over MgSO$_4$, filtered and concentrated. The crude product is purified by MPLC on silica gel eluting with heptane:EA:methanol to give tert-butyl 4-(2-chloro-4-cyano-6-methylphenoxy)butanoate (645 mg) as a colourless oil; LC-MS: $t_R$=1.01 min, [M+H]$^+$=no mass detectable; $^1$H NMR (D$_6$-DMSO): δ 7.94 (d, J=1.7 Hz, 1H), 7.75 (d, J=1.3 Hz, 1H), 3.95 (t, J=6.3 Hz, 2H), 2.46 (t, J=7.2 Hz, 2H), 2.30 (s, 3H), 1.98 (quint, J=6.6 Hz, 2H), 1.41 (s, 9H).

b) A solution of tert-butyl 4-(2-chloro-4-cyano-6-methylphenoxy)butanoate (640 mg, 2.07 mmol), triethylamine (418 mg, 4.13 mmol) and hydroxylamine hydrochloride (215 mg, 3.10 mmol) in ethanol (5 mL) is stirred at 65° C. for 72 h. The mixture is concentrated and the crude product is purified by prep. HPLC to give tert-butyl 4-(2-chloro-4-(N-hydroxycarbamimidoyl)-6-methylphenoxy)butanoate (145 mg) as a pale grey solid; LC-MS: $t_R$=0.65 min, [M+H]$^+$=343.20.

c) A mixture of 2-cyclopentyl-6-methoxy-isonicotinic acid (33 mg, 0.149 mmol), TBTU (50 mg, 0.156 mmol) and DIPEA (62 mg, 0.479 mmol) in DMF (2 mL) is stirred at rt for 15 min before tert-butyl 4-(2-chloro-4-(N-hydroxycarbamimidoyl)-6-methylphenoxy)butanoate (51 mg, 0.149 mmol) is added. The mixture is stirred at rt for 1 h before another portion of TBTU (50 mg, 0.156 mmol) is added. Stirring is continued at rt for 2 h. The mixture is heated to 110° C. and stirring is continued for another hour. The mixture is concentrated and the crude product is purified by prep. HPLC to give tert-butyl 4-(2-chloro-4-(5-(2-cyclopentyl-6-methoxypyridin-4-yl)-1,2,4-oxadiazol-3-yl)-6-methylphenoxy)butanoate (33 mg) as a colourless glass; LC-MS: $t_R$=1.28 min, [M+H]$^+$=528.37.

d) A solution of tert-butyl 4-(2-chloro-4-(5-(2-cyclopentyl-6-methoxypyridin-4-yl)-1,2,4-oxadiazol-3-yl)-6-methylphenoxy)butanoate (90 mg, 170 μmol) in DCM (5 mL) is cooled to 0° C. before TFA (1 mL) is added. The mixture is stirred at 0° C. for 10 min, then at rt for 30 min. The mixture is again cooled to 0° C. before another portion of TFA (1 mL) is added. Stirring is continued at rt for 2 h. The mixture is concentrated and the crude product is purified by prep. HPLC to give the title compound (59 mg) as white solid; LC-MS: $t_R$=1.14 min, [M+H]$^+$=472.29; $^1$H NMR (CDCl$_3$): δ 8.13 (s br, 1H), 8.02 (d, J=1.4 Hz, 1H), 7.88 (d, J=0.7 Hz, 1H), 7.47 (s, 1H), 7.25 (s, 1H), 4.05 (t, J=5.9 Hz, 2H), 4.00 (s, 3H), 3.17-3.28 (m, 1H), 2.74 (t, J=7.3 Hz, 2H), 2.39 (s, 3H), 2.21 (quint, J=6.5 Hz, 2H), 2.05-2.15 (m, 2H), 1.81-1.95 (m, 4H), 1.68-1.80 (m, 2H).

Example 41

2-(2-Chloro-4-(5-(2-cyclopentyl-6-methoxypyridin-4-yl)-1,2,4-oxadiazol-3-yl)-6-methylphenoxy)acetic acid a) tert-Butyl 2-(2-chloro-4-(N-hydroxycarbamimidoyl)-6-methylphenoxy)acetate is prepared in analogy to tert-butyl 4-(2-chloro-4-(N-hydroxycarbamimidoyl)-6-methylphenoxy)butanoate (Example 40); LC-MS: $t_R$=0.57 min, [M+H]$^+$=315.2.

b) The title compound is obtained as a white solid starting from the above tert-butyl 2-(2-chloro-4-(N-hydroxycarbamimidoyl)-6-methylphenoxy)acetate and 2-cyclopentyl-6-methoxy-isonicotinic acid in analogy to Example 40; LC-MS: $t_R$=1.16 min, [M+H]$^+$=444.24; $^1$H NMR (CDCl$_3$): δ 8.99 (s br, 1H), 8.07 (d, J=1.8 Hz, 1H), 7.94 (d, J=1.2 Hz, 1H), 7.48 (s, 1H), 7.27 (s, 1H), 4.75 (s, 2H), 4.01 (s, 3H), 3.18-3.30 (m, 1H), 2.47 (s, 3H), 2.05-2.17 (m, 2H), 1.82-1.95 (m, 4H), 1.69-1.81 (m, 2H).

Example 42

2-(2-Chloro-4-(5-(2-cyclopentyl-6-methoxypyridin-4-yl)-1,2,4-oxadiazol-3-yl)-6-methyl-phenoxy)-N-(2-hydroxyethyl)acetamide The title compound is obtained as a beige wax starting from Example 41 in analogy to Example 13; LC-MS: $t_R$=1.09 min,

[M+H]⁺=487.24; ¹H NMR (CDCl₃): δ 8.01 (s, 1H), 7.89 (s, 1H), 7.47 (t br, J=5.3 Hz, 1H), 7.44 (s, 1H), 7.22 (s, 1H), 4.48 (s, 2H), 3.99 (s, 3H), 3.84 (t, J=4.9 Hz, 2H), 3.61 (q, J=5.4 Hz, 2H), 3.16-3.27 (m, 1H), 3.05 (s br, 1H), 2.39 (s, 3H), 2.04-2.15 (m, 2H), 1.81-1.93 (m, 4H), 1.68-1.78 (m, 2H).

Example 43

3-((2-(2-Chloro-4-(5-(2-cyclopentyl-6-methoxypyridin-4-yl)-1,2,4-oxadiazol-3-yl)-6-methylphenoxy)ethyl)amino)propanoic acid a) To a solution of 2-cyclopentyl-6-methoxy-isonicotinic acid (704 mg, 3.18 mmol) in DMF (5 mL) TBTU (1.43 g, 4.45 mmol) and Hünig's base is added. The mixture is stirred at rt for 15 min before 3-chloro-4-(2,2-diethoxyethoxy)-N-hydroxy-5-methylbenzimidamide (907 mg, 2.86 mmol) is added. Stirring is continued for 18 h before another portion of 3-chloro-4-(2,2-diethoxyethoxy)-N-hydroxy-5-methylbenzimidamide (503 mg, 1.59 mmol) and TBTU (510 mg, 1.59 mmol) is added. Stirring is continued for 4 h. The mixture is diluted with EA (100 mL) and washed with water (50 mL). The washing is extracted three times with EA (3×50 mL). The combined org. extracts are dried over MgSO₄, filtered and concentrated. The residue is dissolved in dioxane (35 mL) and the resulting solution is stirred at 110° C. for 18 h. The solvent is evaporated and the crude product is purified by MPLC on silica gel eluting with heptane:EA 7:3 to give 3-(3-chloro-4-(2,2-diethoxyethoxy)-5-methylphenyl)-5-(2-cyclopentyl-6-methoxypyridin-4-yl)-1,2,4-oxadiazole (1.01 g) as a yellow oil; LC-MS: t_R=1.43 min, [M+H]⁺=502.29; ¹H NMR (CDCl₃): δ 8.06 (d, J=1.9 Hz, 1H), 7.92 (d, J=1.4 Hz, 1H), 7.50 (d, J=0.9 Hz, 1H), 7.29 (d, J=1.1 Hz, 1H), 4.94 (t, J=5.3 Hz, 1H), 4.08 (d, J=5.3 Hz, 2H), 4.02 (s, 3H), 3.77-3.86 (m, 2H), 3.64-3.73 (m, 2H), 3.19-3.29 (m, 1H), 2.44 (s, 3H), 2.08-2.14 (m, 2H), 1.83-1.94 (m, 4H), 1.71-1.77 (m, 2H), 1.28 (t, J=7.1 Hz, 6H).

b) A solution of 3-(3-chloro-4-(2,2-diethoxyethoxy)-5-methylphenyl)-5-(2-cyclopentyl-6-methoxypyridin-4-yl)-1,2,4-oxadiazole (1.01 g, 2.01 mmol) in dioxane (15 mL) and 2 M aq. H₂SO₄ (5 mL) is stirred at 80° C. for 3 h. The mixture is extracted with EA (100 mL) and the org. extract is washed twice with brine (2×35 mL), dried over MgSO₄, filtered and concentrated to give crude 2-(2-chloro-4-(5-(2-cyclopentyl-6-methoxypyridin-4-yl)-1,2,4-oxadiazol-3-yl)-6-methylphenoxy)acetaldehyde (1.02 g) as a yellow oil; LC-MS: t_R=1.11 min, [M+H]⁺=428.19. Part of this material (345 mg, 0.806 mmol.) is dissolved in DCM (10 mL), methanol (10 mL) and acetic acid (0.7 ml) before β-alanine (72 mg, 0.806 mmol) is added. The mixture is degassed and put under argon before Na(BH₃CN) (23 mg, 0.364 mmol) is added. The clear solution is stirred at rt for 2 h before the reaction is quenched by adding water (2 mL). The mixture is concentrated and the crude product is purified by prep. HPLC to give the title compound (77 mg) as a brownish solid; LC-MS: t_R=0.95 min, [M+H]⁺=501.23; ¹H NMR (CDCl₃): δ 8.53 (s br, 2H), 7.83 (s, 1H), 7.67 (s, 1H), 7.33 (s, 1H), 7.07 (s, 1H), 4.20-4.30 (m, 2H), 3.95 (s, 3H), 3.39-3.49 (m, 2H), 3.25-3.36 (m, 2H), 3.12-3.22 (m, 1H), 2.64-2.75 (m, 2H), 2.32 (s, 3H), 2.02-2.12 (m, 2H), 1.78-1.91 (m, 4H), 1.68-1.78 (m, 2H).

Example 44

1-(2-(2-Chloro-4-(5-(2-cyclopentyl-6-methoxypyridin-4-yl)-1,2,4-oxadiazol-3-yl)-6-methylphenoxy)ethyl)azetidine-3-carboxylic acid The title compound is obtained as a beige solid using azetidine-3-carboxylic acid in analogy to Example 43; LC-MS: t_R=0.95 min, [M+H]⁺=514.06.

Example 45

2-((2-(2-Chloro-4-(5-(2-cyclopentyl-6-methoxypyridin-4-yl)-1,2,4-oxadiazol-3-yl)-6-methylphenoxy)ethyl)amino)ethanol The title compound is obtained as a beige wax using ethanolamine in analogy to Example 43; LC-MS: t_R=0.93 min, [M+H]⁺=473.23; ¹H NMR (CDCl₃): δ 8.03 (d, J=1.8 Hz, 1H), 7.89 (d, J=1.3 Hz, 1H), 7.46 (s, 1H), 7.25 (s, 1H), 4.12 (t, J=5.0 Hz, 2H), 4.00 (s, 3H), 3.74 (t, J=5.0 Hz, 2H), 3.18-3.27 (m, 1H), 3.10 (t, J=5.0 Hz, 2H), 2.93 (t, J=5.2 Hz, 2H), 2.54 (s br, 2H), 2.41 (s, 3H), 2.04-2.14 (m, 2H), 1.81-1.93 (m, 4H), 1.67-1.79 (m, 2H).

Example 46

4-(4-(5-(2-Cyclopentyl-6-methoxypyridin-4-yl)-1,2,4-oxadiazol-3-yl)-2-ethyl-6-methylphenoxy)-N-(2-hydroxyethyl)butanamide The title compound is prepared starting from Example 6 in analogy to Example 13; LC-MS: t_R=1.10 min, [M+H]⁺=509.49; ¹H NMR (CDCl₃): δ 7.85 (s, 1H), 7.83 (s, 1H), 7.49 (s, 1H), 7.28 (s, 1H), 6.29 (t, J=5.0 Hz, 1H), 4.00 (s, 3H), 3.87 (t, J=5.9 Hz, 2H), 3.73-3.79 (m, 2H), 3.45-3.52 (m, 2H), 3.18-3.27 (m, 1H), 3.03 (s br, 1H), 2.72 (q, J=7.5 Hz, 2H), 2.54 (t, J=7.3 Hz, 2H), 2.35 (s, 3H), 2.15-2.24 (m, 2H), 2.04-2.14 (m, 2H), 1.82-1.96 (m, 4H), 1.66-1.78 (m, 2H), 1.30 (t, J=7.5 Hz, 3H).

Example 47

(S)-3-((3-(4-(5-(2-Cyclopentyl-6-methoxypyridin-4-yl)-1,2,4-oxadiazol-3-yl)-2-ethyl-6-methylphenoxy)-2-hydroxypropyl)(methyl)amino)propanoic acid The title compound is prepared starting from (S)-5-(2-cyclopentyl-6-methoxypyridin-4-yl)-3-(3-ethyl-5-methyl-4-(oxiran-2-ylmethoxy)phenyl)-1,2,4-oxadiazole and ethyl-3-(methylamino)-propanoate in analogy to Example 9; LC-MS: t_R=0.95 min, [M+H]⁺=539.53; ¹H NMR (CDCl₃): δ 7.84 (s, 1H), 7.82 (s, 1H), 7.48 (s, 1H), 7.27 (s, 1H), 6.49 (s br, 2H), 4.52-4.60 (m, 1H), 4.00 (s, 3H), 3.90-3.96 (m, 1H), 3.84-3.90 (m, 1H), 3.41-3.51 (m, 2H), 3.18-3.39 (m, 3H), 2.97 (s, 3H), 2.68-2.80 (m, 4H), 2.36 (s, 3H), 2.04-2.14 (m, 2H), 1.82-1.94 (m, 4H), 1.68-1.78 (m, 2H), 1.30 (t, J=7.5 Hz, 3H).

Example 48

(R)-3-(3-(4-(5-(2-Cyclopentyl-6-methoxypyridin-4-yl)-1,2,4-oxadiazol-3-yl)-2-ethyl-6-methylphenoxy)-2-hydroxypropyl)(methyl)amino)propanoic acid The title compound is prepared in analogy to Example 47; LC-MS: t_R=0.94 min, [M+H]⁺=539.35.

Example 49

3-((2-(4-(5-(2-Cyclopentyl-6-methoxypyridin-4-yl)-1,2,4-oxadiazol-3-yl)-2-ethyl-6-methylphenoxy)ethyl)amino)-3-oxopropanoic acid a) 2-(4-(5-(2-Cyclopentyl-6-methoxypyridin-4-yl)-1,2,4-oxadiazol-3-yl)-2-ethyl-6-methylphenoxy)ethanamine (2.10 g) is obtained starting from 2-(4-(5-(2-cyclopentyl-6-methoxypyridin-4-yl)-1,2,4-oxadiazol-3-yl)-2-ethyl-6-methylphenoxy)ethyl methanesulfonate (2.14 g, 4.27 mmol) and 7 N ammonia in methanol in analogy to Example 29; LC-MS: $t_R$=0.91 min, [M+H]$^+$=464.29.

b) The title compound is prepared from the above amine and mono tert.-butyl malonate in analogy to Example 31; LC-MS: $t_R$=1.11 min, [M+H]$^+$=509.21; $^1$H NMR (CDCl$_3$): δ 7.54 (s, 1H), 7.47 (s, 1H), 7.21 (s, 1H), 6.95 (s, 1H), 4.99 (s br, 2H), 3.85 (s, 3H), 3.68-3.77 (m, 2H), 3.57-3.65 (m, 2H), 3.41 (s, 2H), 3.02-3.12 (m, 1H), 2.50 (q, J=7.0 Hz, 2H), 2.12 (s, 3H), 1.93-2.03 (m, 2H), 1.70-1.85 (m, 4H), 1.61-1.70 (m, 2H), 1.12 (t, J=7.4 Hz, 3H).

Example 50

4-((2-(4-(5-(2-Cyclopentyl-6-methoxypyridin-4-yl)-1,2,4-oxadiazol-3-yl)-2-ethyl-6-methylphenoxy)ethyl)amino)-4-oxobutanoic acid The title compound is prepared in analogy to Example 49 using mono methyl succinate; LC-MS: $t_R$=1.17 min, [M+H]$^+$=537.25.

Example 51

2-((2-(2-Chloro-4-(5-(2-cyclopentyl-6-methoxypyridin-4-yl)-1,2,4-oxadiazol-3-yl)-6-methoxyphenoxy)ethyl)amino)acetic acid The title compound is prepared starting from 2-cyclopentyl-6-methoxy-isonicotinic acid, 3-chloro-4-(2,2-dimethoxyethoxy)-N-hydroxy-5-methoxybenzimidamide and ethyl glycinate in analogy to Example 43 and 1 (saponification); LC-MS: $t_R$=0.88 min, [M+H]$^+$=503.11.

Example 52

1-(2-(2-Chloro-4-(5-(2-cyclopentyl-6-methoxypyridin-4-yl)-1,2,4-oxadiazol-3-yl)-6-methoxyphenoxy)ethyl)azetidine-3-carboxylic acid The title compound is prepared starting from 2-cyclopentyl-6-methoxy-isonicotinic acid, 3-chloro-4-(2,2-dimethoxyethoxy)-N-hydroxy-5-methoxybenzimidamide and ethyl azetidine-3-carboxylate in analogy to Example 43 and 1 (saponification); LC-MS: $t_R$=0.88 min, [M+H]$^+$=528.92; $^1$H NMR (CDCl$_3$): δ 7.79 (d, J=1.5 Hz, 1H), 7.57 (d, J=1.4 Hz, 1H), 7.45 (s, 1H), 7.24 (s, 1H), 5.96 (s br, 1H), 4.55-4.64 (m, 2H), 4.44-4.54 (m, 2H), 4.32-4.38 (m, 2H), 4.00 (s, 6H), 3.65-3.74 (m, 1H), 3.58-3.65 (m, 2H), 3.18-3.27 (m, 1H), 2.05-2.14 (m, 2H), 1.82-1.94 (m, 4H), 1.75 (m, 2H).

Example 53

2-(4-(3-(2-Cyclopentyl-6-methoxypyridin-4-yl)-1,2,4-oxadiazol-5-yl)-2-ethyl-6-methylphenoxy)acetic acid a) To a solution of 2-cyclopentyl-N-hydroxy-6-methoxy-isonicotinamidine (870 mg, 3.70 mmol), 4-benzyloxy-3-ethyl-5-methyl-benzoic acid (1.00 g, 3.70 mmol) and DIPEA (1.44 g, 11.1 mmol) in DCM (30 mL), TBTU (1.43 g, 4.44 mmol) is added. The mixture is stirred at rt for 1 h before diluted with EA (150 mL) and water (50 mL). The org. phase is separated, washed with sat. aq. NaHCO$_3$ solution (50 mL) followed by brine (50 mL), dried over MgSO$_4$, filtered and concentrated. The remaining pale brown oil is dissolved in dioxane (40 mL) and then stirred at 115° C. for 48 h. The solvent is evaporated and the crude product is purified by CC on silica gel eluting with heptane:EA 1:9 to give 4-[5-(4-benzyloxy-3-ethyl-5-methyl-phenyl)-[1,2,4]oxadiazol-3-yl]-2-cyclopentyl-6-methoxy-pyridine (1040 mg) as a pale yellow oil; LC-MS**: $t_R$=1.11 min, [M+H]$^+$=470.26.

b) Pd/C (150 mg, 10% Pd) is added to a solution of 4-[5-(4-benzyloxy-3-ethyl-5-methyl-phenyl)-[1,2,4]oxadiazol-3-yl]-2-cyclopentyl-6-methoxy-pyridine (1040 mg, 2.22 mmol) in THF (20 mL) and methanol (20 mL). The mixture is stirred under 1 bar of H$_2$ at rt for 24 h. The catalyst is removed by filtration and the filtrate is concentrated and dried to give 4-[3-(2-cyclopentyl-6-methoxy-pyridin-4-yl)-[1,2,4]oxadiazol-5-yl]-2-ethyl-6-methyl-phenol (672 mg) as an off-white solid; LC-MS**: $t_R$=0.97 min, [M+H]$^+$=380.27.

c) The title compound is prepared from the above phenol using ethyl bromoacetate in analogy to Example 5; LC-MS: $t_R$=1.15 min, [M+H]$^+$=438.21; $^1$H NMR (CDCl$_3$): δ 7.87 (s, 1H), 7.83 (s, 1H), 7.42 (s, 1H), 7.22 (s, 1H), 6.85 (s br, 1H), 4.41 (s, 2H), 3.97 (s, 3H), 3.13-3.25 (m, 1H), 2.73 (q, J=7.5 Hz, 2H), 2.36 (s, 3H), 2.01-2.13 (m, 2H), 1.81-1.93 (m, 4H), 1.66-1.76 (m, 2H), 1.29 (t, J=7.5 Hz, 3H).

Example 54

4-(4-(3-(2-Cyclopentyl-6-methoxypyridin-4-yl)-1,2,4-oxadiazol-5-yl)-2-ethyl-6-methylphenoxy)butanoic acid The title compound is prepared in analogy to Example 53 using ethyl 4-iodobutyrate in step c); LC-MS: $t_R$=1.21 min, [M+H]$^+$=465.99; $^1$H NMR (CDCl$_3$): δ 8.53 (s br, 1H), 7.92 (s, 1H), 7.91 (s, 1H), 7.48 (s, 1H), 7.29 (s, 1H), 4.00 (s, 3H), 3.91 (t, J=6.1 Hz, 2H), 3.16-3.27 (m, 1H), 2.69-2.79 (m, 4H), 2.39 (s, 3H), 2.17-2.26 (m, 2H), 2.04-2.14 (m, 2H), 1.82-1.95 (m, 4H), 1.67-1.79 (m, 2H), 1.32 (t, J=7.5 Hz, 3H).

Example 55

2-((2-(4-(3-(2-Cyclopentyl-6-methoxypyridin-4-yl)-1,2,4-oxadiazol-5-yl)-2-ethyl-6-methylphenoxy)ethyl)amino)acetic acid The title compound is prepared starting from 4-[3-(2-cyclopentyl-6-methoxy-pyridin-4-yl)-[1,2,4]oxadiazol-5-yl]-2-ethyl-6-methyl-phenol (Example 53, step b) in analogy to Example 1 using tert.-butyl glycinate; LC-MS: $t_R$=0.93 min, [M+H]$^+$=481.12.

Example 56

2-((2-(4-(3-(2-Cyclopentyl-6-methoxypyridin-4-yl)-1,2,4-oxadiazol-5-yl)-2-ethyl-6-methylphenoxy)ethyl)(methyl)amino)acetic acid The title compound is prepared starting from 4-[3-(2-cyclopentyl-6-methoxy-pyridin-4-yl)-[1,2,4]oxadiazol-5-yl]-2-ethyl-6-methyl-phenol (Example 53, step b) in analogy to Example 1 using sarcosine methyl ester; LC-MS: $t_R$=0.95 min, [M+H]$^+$=495.23; $^1$H NMR (CDCl$_3$): δ 7.84 (s, 1H), 7.81

(d, J=1.6 Hz, 1H), 7.40 (s, 1H), 7.20 (d, J=0.7 Hz, 1H), 6.42 (s br, 1H), 4.18-4.24 (m, 2H), 3.96 (s, 3H), 3.88 (s, 2H), 3.66-3.73 (m, 2H), 3.11-3.21 (m, 1H), 3.10 (s, 3H), 2.70 (q, J=7.5 Hz, 2H), 2.36 (s, 3H), 2.00-2.11 (m, 2H), 1.79-1.92 (m, 4H), 1.65-1.77 (m, 2H), 1.28 (t, J=7.5 Hz, 3H).

Example 57

3-((2-(4-(3-(2-Cyclopentyl-6-methoxypyridin-4-yl)-1,2,4-oxadiazol-5-yl)-2-ethyl-6-methylphenoxy) ethyl)amino)propanoic acid The title compound is prepared starting from 4-[3-(2-cyclopentyl-6-methoxy-pyridin-4-yl)-[1,2,4]oxadiazol-5-yl]-2-ethyl-6-methyl-phenol (Example 53, step b) in analogy to Example 1 using β-alanine ethyl ester; LC-MS: $t_R$=0.94 min, [M+H]$^+$=495.20.

Example 58

1-(2-(4-(3-(2-Cyclopentyl-6-methoxypyridin-4-yl)-1,2,4-oxadiazol-5-yl)-2-ethyl-6-methylphenoxy)ethyl) azetidine-3-carboxylic acid The title compound is prepared starting from 4-[3-(2-cyclopentyl-6-methoxy-pyridin-4-yl)-[1,2,4]oxadiazol-5-yl]-2-ethyl-6-methyl-phenol (Example 53, step b) in analogy to Example 1 using azetidine-3-carboxylic acid methyl ester; LC-MS: $t_R$=0.95 min, [M+H]$^+$=507.21.

Example 59

2-((3-(4-(3-(2-Cyclopentyl-6-methoxypyridin-4-yl)-1,2,4-oxadiazol-5-yl)-2-ethyl-6-methylphenoxy) propyl)amino)acetic acid The title compound is prepared starting from 4-[3-(2-cyclopentyl-6-methoxy-pyridin-4-yl)-[1,2,4]oxadiazol-5-yl]-2-ethyl-6-methyl-phenol (Example 53, step b) in analogy to Example 1 using 3-bromo-propanol and glycine tert.-butyl ester; LC-MS: $t_R$=0.97 min, [M+H]$^+$=495.24; $^1$H NMR (CDCl$_3$): δ 7.84 (s, 1H), 7.80 (s, 1H), 7.41 (s, 1H), 7.22 (s, 1H), 3.97 (s, 3H), 3.91 (t, J=5.3 Hz, 2H), 3.66 (s, 2H), 3.34-3.41 (m, 2H), 3.13-3.23 (m, 1H), 2.68 (q, J=7.4 Hz, 2H), 2.35-2.43 (m, 2H), 2.33 (s, 3H), 2.02-2.11 (m, 2H), 1.81-1.93 (m, 4H), 1.67-1.76 (m, 2H), 1.29 (t, J=7.5 Hz, 3H); $^{13}$C NMR (CDCl$_3$): δ 175.7, 170.8, 167.7, 165.0, 164.2, 158.8, 137.9, 136.7, 131.9, 129.0, 127.3, 120.0, 111.9, 105.5, 70.0, 53.5, 50.0, 47.5, 45.4, 33.3, 27.2, 25.9, 22.8, 16.5, 14.7.

Example 60

2-(4-(5-(2-Cyclopentyl-6-methoxypyridin-4-yl)-1,3,4-oxadiazol-2-yl)-2-ethyl-6-methylphenoxy)acetic acid a) To a solution of 2-cyclopentyl-6-methoxy-isonicotinic acid hydrazide (870 mg, 3.70 mmol), 4-benzyloxy-3-ethyl-5-methyl-benzoic acid (1.00 g, 3.70 mmol) and DIPEA (1.44 g, 11.1 mmol) in DCM (30 mL), TBTU (1.43 g, 4.44 mmol) is added. The mixture is stirred at rt for 1 h before diluted with EA (150 mL) and water (50 mL). The org. phase is separated, washed with sat. aq. NaHCO$_3$ solution (50 mL) followed by brine (50 mL), dried over MgSO$_4$, filtered and concentrated. The remaining pale yellow oil is dissolved in THF (50 mL) and Burgess reagent (1.23 g, 5.18 mmol) is added. The mixture is stirred at 110° C. for 15 min under microwave irradiation before it is diluted with EA (200 mL) and washed twice with water (50 mL). The org. extract is dried over MgSO$_4$, filtered and concentrated and the crude product is purified by CC on silica gel eluting with heptane:EA 1:9 to give 4-[5-(4-benzyloxy-3-ethyl-5-methyl-phenyl)-[1,3,4]oxadiazol-2-yl]-2-cyclopentyl-6-methoxy-pyridine (750 mg) as a pale yellow oil; LC-MS**: $t_R$=1.06 min, [M+H]$^+$=470.21.

b) Pd/C (150 mg, 10% Pd) is added to a solution of 4-[5-(4-benzyloxy-3-ethyl-5-methyl-phenyl)-[1,3,4]oxadiazol-2-yl]-2-cyclopentyl-6-methoxy-pyridine (750 mg, 1.60 mmol) in THF (20 mL) and methanol (20 mL). The mixture is stirred under 1 bar of H$_2$ at rt for 24 h. The catalyst is removed by filtration and the filtrate is concentrated and dried to give 4-[5-(2-cyclopentyl-6-methoxy-pyridin-4-yl)-[1,3,4]oxadiazol-2-yl]-2-ethyl-6-methyl-phenol (495 mg) as a white solid; LC-MS**: $t_R$=0.91 min, [M+H]$^+$=380.25; $^1$H NMR (D$_6$-DMSO): δ 1.20 (t, J=7.5 Hz, 3H), 1.65-1.74 (m, 2H), 1.76-1.88 (m, 4H), 1.99-2.09 (m, 2H), 2.29 (s, 3H), 2.69 (q, J=7.5 Hz, 2H), 3.94 (s, 3H), 7.26 (d, J=1.0 Hz, 1H), 7.50 (d, J=0.8 Hz, 1H), 7.76 (d, J=2.0 Hz, 1H), 7.78 (d, J=2.0 Hz, 1H).

c) The title compound is prepared from the above phenol using ethyl bromoacetate in analogy to Example 5; LC-MS: $t_R$=1.03 min, [M+H]$^+$=438.33.

Example 61

4-(4-(5-(2-Cyclopentyl-6-methoxypyridin-4-yl)-1,3,4-oxadiazol-2-yl)-2-ethyl-6-methylphenoxy)butanoic acid The title compound is prepared in analogy to Example 60 using ethyl 4-iodobutyrate in step c); LC-MS: $t_R$=1.09 min, [M+H]$^+$=466.38; $^1$H NMR (D$_6$-DMSO): δ 7.88 (s, 1H), 7.87 (s, 1H), 7.52 (s, 1H), 7.29 (s, 1H), 3.94 (s, 3H), 3.84 (t, J=6.3 Hz, 2H), 3.21-3.31 (m, 1H), 2.70 (q, J=7.5 Hz, 2H), 2.43 (t, J=7.3 Hz, 2H), 2.34 (s, 3H), 1.96-2.09 (m, 4H), 1.76-1.88 (m, 4H), 1.63-1.74 (m, 2H), 1.23 (t, J=7.5 Hz, 3H).

Example 62

3-((2-(4-(5-(2-Cyclopentyl-6-methoxypyridin-4-yl)-1,3,4-oxadiazol-2-yl)-2-ethyl-6-methylphenoxy) ethyl)amino)propanoic acid The title compound is prepared starting from 4-[5-(2-cyclopentyl-6-methoxy-pyridin-4-yl)-[1,3,4]oxadiazol-2-yl]-2-ethyl-6-methyl-phenol (Example 60, step b) in analogy to Example 1 using β-alanine ethyl ester; LC-MS: $t_R$=0.85 min, [M+H]$^+$=495.37; $^1$H NMR (CDCl$_3$): δ 7.73 (s, 1H), 7.67 (s, 1H), 7.38 (s, 1H), 7.12 (s, 1H), 4.13-4.18 (m, 2H), 3.98 (s, 3H), 3.37-3.42 (m, 2H), 3.23-3.29 (m, 2H), 3.15-3.23 (m, 1H), 2.64-2.74 (m, 4H), 2.35 (s, 3H), 2.02-2.13 (m, 2H), 1.81-1.93 (m, 4H), 1.67-1.78 (m, 2H), 1.27 (t, J=7.5 Hz, 3H).

Example 63

1-(2-(4-(5-(2-Cyclopentyl-6-methoxypyridin-4-yl)-1,3,4-oxadiazol-2-yl)-2-ethyl-6-methylphenoxy)ethyl) azetidine-3-carboxylic acid The title compound is prepared starting from 4-[5-(2-cyclopentyl-6-methoxy-pyridin-4-yl)-[1,3,4]oxadiazol-2-yl]-2-ethyl-6-methyl-phenol (Example 60, step b) in analogy to Example 1 using azetidine-3-carboxylic acid methyl ester; LC-MS: $t_R$=0.84 min, [M+H]$^+$=507.37.

Example 64

(S)-1-(4-(5-(2-Cyclopentyl-6-methoxypyridin-4-yl)-1,3,4-oxadiazol-2-yl)-2-ethyl-6-methylphenoxy)-3-((2-hydroxyethyl)amino)propan-2-ol The title compound is prepared starting from 4-[5-(2-cyclopentyl-6-methoxy-pyridin-4-yl)-[1,3,4]oxadiazol-2-yl]-2-ethyl-6-methyl-phenol (Example 60, step b) in analogy to Example 3; LC-MS: $t_R$=0.82 min, [M+H]$^+$=498.24; $^1$H NMR (CDCl$_3$): δ 7.81 (s, 1H), 7.79 (s, 1H), 7.44 (s, 1H), 7.18 (s, 1H), 4.15-4.23 (m, 1H), 3.99 (s, 3H), 3.86 (d, J=5.0 Hz, 2H), 3.76 (t, J=4.7 Hz, 2H), 3.15-3.34 (m, 4H), 2.84-2.98 (m, 4H), 2.74 (q, J=7.5 Hz, 2H), 2.38 (s, 3H), 2.02-2.12 (m, 2H), 1.80-1.93 (m, 4H), 1.65-1.77 (m, 2H), 1.29 (t, J=7.5 Hz, 3H).

Example 65

(S)-2-(3-(4-(5-(2-Cyclopentyl-6-methoxypyridin-4-yl)-1,3,4-oxadiazol-2-yl)-2-ethyl-6-methylphenoxy)-2-hydroxypropyl)amino)propane-1,3-diol The title compound is prepared starting from 4-[5-(2-cyclopentyl-6-methoxy-pyridin-4-yl)-[1,3,4]oxadiazol-2-yl]-2-ethyl-6-methyl-phenol (Example 60, step b) in analogy to Example 4; LC-MS: $t_R$=0.82 min, [M+H]$^+$=527.37.

Example 66

(S)-4-(3-(4-(5-(2-Cyclopentyl-6-methoxypyridin-4-yl)-1,3,4-oxadiazol-2-yl)-2-ethyl-6-methylphenoxy)-2-hydroxypropyl)amino)-4-oxobutanoic acid The title compound is prepared starting from (S)-2-(2-cyclopentyl-6-methoxypyridin-4-yl)-5-(3-ethyl-5-methyl-4-(oxiran-2-ylmethoxy)phenyl)-1,3,4-oxadiazole (obtained from 4-[5-(2-cyclopentyl-6-methoxy-pyridin-4-yl)-[1,3,4]oxadiazol-2-yl]-2-ethyl-6-methyl-phenol (Example 60, step b) in analog to Example 3, step a) in analogy to Example 14 using mono tert.-butyl succinate; LC-MS: $t_R$=0.94 min, [M+H]$^+$=553.19; $^1$H NMR (CD$_3$OD): δ 7.83 (d, J=1.8 Hz, 1H), 7.79 (d, J=1.6 Hz, 1H), 7.43 (d, J=0.7 Hz, 1H), 7.16 (d, J=0.9 Hz, 1H), 4.08-4.15 (m, 1H), 3.97 (s, 3H), 3.81-3.91 (m, 2H), 3.57 (dd, J$_1$=13.7 Hz, J$_2$=4.7 Hz, 1H), 3.33-3.39 (m, 1H), 3.19-3.28 (m, 1H), 2.80 (q, J=7.5 Hz, 2H), 2.52 (s, 4H), 2.40 (s, 3H), 2.04-2.14 (m, 2H), 1.84-1.96 (m, 4H), 1.71-1.80 (m, 2H), 1.31 (t, J=7.5 Hz, 3H).

Example 67

S1P$_1$ β-Arrestin Recruitment (Tango) Assay to Determine EC$_{50}$ Values

Assay Principle:

Upon ligand activation, G protein-coupled receptors (GPCR) trigger two pathways that independently transduce signals to the cell: one through heterotrimeric GTP-binding proteins (G proteins) and one through β-arrestins. Agonist-induced GPCRs recruit β-arrestin proteins, which then bind to the carboxy-terminal domain of ligand-activated GPCRs. The amount of β-arrestin recruitment can be used to assess the potency and efficacy of GPCR activating ligands.

To measure the potency and efficacy of compounds as S1P$_1$ (EDG1) receptor agonists, Tango™-EDG1 bla U2OS cells (Invitrogen, USA, Catalog #K1520) are used. The Tango™ GPCR technology is based on GeneBLAzer β-lactamase reporter cell assays, which uses a mammalian-optimized β-lactamase reporter gene (bla) combined with a FRET-enabled substrate. The host cells, U2OS, stably express a human S1P$_1$ (EDG1) receptor/transcription factor (TF) fusion protein. The cells also express a recombinant protease tagged β-arrestin protein, which is recruited to the S1P$_1$ receptor upon ligand stimulation and specifically cleaves the S1P$_1$-TF fusion protein. The released TF activates the β-lactamase (bla) reporter gene. To measure the reporter gene activity, cells are loaded with a fluorescent substrate containing two chemically coupled fluorophores, coumarin and fluorescein. In the absence of bla expression, the substrate molecule remains intact, and the excitation at 410 nm results in an emission of green fluorescent light (520 nM) due to internal FRET. In the presence of bla, the chemical bond is cleaved and FRET is inhibited. In this situation, excitation at 410 nM results in a blue fluorescence emission signal (450 nm). The amount of β-arrestin recruitment is proportional to the increase in blue fluorescence.

Cell Culture:

Tango™-EDG1 bla U2OS cells are cultivated in McCoy's 5A containing 10% dialyzed FBS, 0.1 mM NEAA, 25 mM HEPES, 1 mM sodium pyruvate, 1% Penicillin/Streptomycin, 200 µg/ml zeocin, 50 µg/ml hygromycin and 100 µg/ml geneticin (Invitrogen, USA). Cells are detached with trypsin, resuspended in medium and then counted. Cells are centrifuged, then washed with Assay Medium (Freestyle™ expression medium for HEK-293 (Invitrogen, USA)) and seeded at 5000 cells/well in 384-well black plates with clear bottom (Greiner, Germany) in 30 µl/well of Assay Medium.

Agonist Assay:

Compounds (10 mM stock in DMSO) are diluted first in DMSO. The pre-diluted compounds solutions are then transferred into Assay Medium/0.1% fatty acid free BSA to reach a fourfold concentrated compound stock, which is applied to the cells to reach the final compound concentrations that range from 10 µM to 0.0005 nM (0.5% final DMSO). Cells are then incubated for 16 h at 37° C. and 5% CO$_2$.

Detection:

The substrate (1 µM LiveBLAzer™ FRET-B/G (with CCF$_4$-AM) substrate, 1 mg/mL Pluronic® F-127 surfactant, 0.001% acetic acid, 4% w/w PEG 400, 3% TR-40 by volume in water (Invitrogen, USA)) is added to each well and the cells are incubated for 2 h at rt in the dark. The plates are read with a Synergy4™ (Biotek, USA) using 410 nM excitation wavelength and emission wavelengths 450 nm and 520 nm.

Data Analysis:

The EC$_{50}$ of a test compound is the concentration of a compound inducing 50% of its maximal activity. For EC$_{50}$ calculations, 450 nM/520 nM ratios are calculated after background subtraction (i.e. lanes without cells) and the maximal effect of the compound is used as 100% and as upper asymptote.

Agonistic activities (Tango EC$_{50}$ values) have been measured for all exemplified compounds and are in the range of 0.02 and 69 nM with an average of 3.3 nM. EC$_{50}$ values of these compounds are displayed in Table 2.

TABLE 2

| Compound of Example | EC$_{50}$ [nM] |
|---|---|
| 1 | 0.04 |
| 2 | 0.4 |
| 3 | 8.3 |
| 4 | 6.6 |
| 5 | 1.6 |
| 6 | 0.2 |
| 7 | 1.5 |

TABLE 2-continued

| Compound of Example | EC$_{50}$ [nM] |
|---|---|
| 8 | 0.3 |
| 9 | 0.07 |
| 10 | 0.06 |
| 11 | 0.2 |
| 12 | 0.3 |
| 13 | 2.4 |
| 14 | 0.03 |
| 15 | 0.02 |
| 16 | 0.2 |
| 17 | 0.2 |
| 18 | 0.3 |
| 19 | 0.4 |
| 20 | 1.5 |
| 21 | 0.659 |
| 22 | 2.95 |
| 23 | 24.7 |
| 24 | 69 |
| 25 | 4.23 |
| 26 | 15.1 |
| 27 | 10.3 |
| 28 | 25.6 |
| 29 | 0.265 |
| 30 | 7.98 |
| 31 | 0.0716 |
| 32 | 0.072 |
| 33 | 0.501 |
| 34 | 0.515 |
| 35 | 0.627 |
| 36 | 1.7 |
| 37 | 0.2 |
| 38 | 0.893 |
| 39 | 0.1 |
| 40 | 0.05 |
| 41 | 1.1 |
| 42 | 0.4 |
| 43 | 0.1 |
| 44 | 0.1 |
| 45 | 1.7 |
| 46 | 1.8 |
| 47 | 0.1 |
| 48 | 0.6 |
| 49 | 0.05 |
| 50 | 0.1 |
| 51 | 0.7 |
| 52 | 0.6 |
| 53 | 1.2 |
| 54 | 0.1 |
| 55 | 0.1 |
| 56 | 0.1 |
| 57 | 0.05 |
| 58 | 0.2 |
| 59 | 2.7 |
| 60 | 7.2 |
| 61 | 0.1 |
| 62 | 0.2 |
| 63 | 1.1 |
| 64 | 3.0 |
| 65 | 0.7 |
| 66 | 0.05 |

Example 68

Assessment of In Vivo Efficacy

The efficacy of the compounds of Formula (I) is assessed by measuring the circulating lymphocytes after oral administration of 3 to 30 mg/kg of a compound of Formula (I) to normotensive male Wistar rats. The animals are housed in climate-controlled conditions with a 12 h-light/dark cycle, and have free access to normal rat chow and drinking water. Blood is collected before and 3, 6 and 24 h after drug administration. Full blood is subjected to hematology using Advia Hematology system (Bayer Diagnostics, Zurich, Switzerland).

All data are presented as mean±SEM. Statistical analyses are performed by analysis of variance (ANOVA) using Statistica (StatSoft) and the Student-Newman-Keuls procedure for multiple comparisons. The null hypothesis is rejected when $p<0.05$.

As an example, Table 3 shows the effect on lymphocyte counts 6 h after oral administration of 10 mg/kg of a compound of the present invention to normotensive male Wistar rats as compared to a group of animals treated with vehicle only. Lymphocyte counts 6 h after oral administration have been measured for 49 out of 66 exemplified compounds and are in the range of −24% to −82% with an average of −63% (excluding the compounds of Examples 49 and 51 which were dosed at 3 mg/kg).

TABLE 3

| Compound of Example | Lymphocyte counts |
|---|---|
| 1 | −69 |
| 2 | −70 |
| 3 | −25 |
| 4 | −65 |
| 5 | −35 |
| 6 | −53 |
| 7 | −70 |
| 8 | −66 |
| 9 | −72 |
| 10 | −51 |
| 11 | −60 |
| 12 | −61 |
| 13 | −77 |
| 15 | −55 |
| 16 | −75 |
| 18 | −24 |
| 20 | −57 |
| 21 | −74 |
| 27 | −42 |
| 29 | −76 |
| 30 | −75 |
| 31 | −68 |
| 32 | −65 |
| 33 | −78 |
| 34 | −66 |
| 35 | −71 |
| 36 | −73 |
| 37 | −71 |
| 39 | −66 |
| 40 | −65 |
| 41 | −49 |
| 42 | −75 |
| 43 | −62 |
| 44 | −62 |
| 45 | −72 |
| 47 | −64 |
| 49 | −49* |
| 50 | −57 |
| 51 | −22* |
| 52 | −71 |
| 53 | −72 |
| 54 | −72 |
| 55 | −72 |
| 57 | −74 |
| 59 | −82 |
| 60 | −35 |
| 61 | −27 |
| 62 | −63 |
| 63 | −71 |

*at an oral dose of 3 mg/kg.

Example 69

Measurement of Isometric Force Development

Animals are obtained from RCC Ltd (Füllinsdorf, Switzerland). Female Wistar rats are euthanized by exposure to $CO_2$.

The tracheae are excised and rings from the lower segments are prepared. Rings of trachea are suspended in tissue baths (10 mL) containing Krebs-Henseleit buffer of the following composition (mM): NaCl 115; KCl 4.7; $MgSO_4$ 1.2; $KH_2PO_4$ 1.5; $CaCl_2$ 2.5; $NaHCO_3$ 25; glucose 10. Bathing solution is maintained at 37° C. and aerated with 95%$O_2$/5% $CO_2$ (pH 7.4). A resting force of 2 g (20 mN) is applied to the ring preparation, and changes in force generation are measured using an isometric force recorder (EMKA Technologies Inc., Paris, France). Viability of rings is assessed by exposure to a depolarizing concentration of KCl (50 mM). Contraction of trachea is expressed as a percentage of the response to KCl.

The compounds are prepared as stock solutions of 0.3 mM in pure DMSO. Compounds are added to the bath (10 mL) in a volume of 33 μL to give a final bath concentration of DMSO of 0.33%.

Contraction of female rat trachea was measured for 14 out of 66 exemplified compounds. The results are compiled in Table 4.

TABLE 4

| Compound | % trachea constriction at | | | | | | | | |
|---|---|---|---|---|---|---|---|---|---|
| | 3 nM | 10 nM | 30 nM | 0.1 μM | 0.3 μM | 1 μM | 3 μM | 10 μM | 30 μM |
| Example 1 | | | n.d. | <5 | 53 | 96 | n.d. | | |
| Example 2 | n.d. | <5 | <5 | <5 | 55 | 93 | n.d. | | |
| Example 3 | | | | n.d. | <5 | <5 | <5 | <5 | <5 |
| Example 4 | | | | n.d. | <5 | <5 | <5 | <5 | <5 |
| Example 5 | n.d. | <5 | <5 | 66 | 84 | 124 | n.d. | | |
| Example 6 | n.d. | <5 | <5 | <5 | 91 | 110 | n.d. | | |
| Example 7 | n.d. | <5 | n.d. | <5 | <5 | 68 | n.d. | | |
| Example 13 | | | | n.d. | <5 | n.d. | | <5 | n.d. |
| Example 32 | | | n.d. | 27 | 50 | 105 | n.d. | | |
| Example 35 | n.d. | <5 | <5 | 86 | n.d. | 108 | n.d. | | |
| Example 41 | n.d. | <5 | 10 | 56 | n.d. | 120 | n.d. | | |
| Example 45 | | | | n.d. | <5 | <5 | <5 | 52 | n.d. |
| Example 50 | n.d. | <5 | 55 | 103 | n.d. | | | | |
| Example 54 | | n.d. | <5 | 5.6 | 55 | 76 | n.d. | | |

The invention claimed is:

1. A compound of the Formula (I),

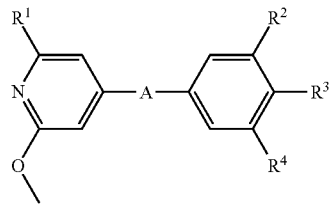

Formula (I)

wherein
A represents

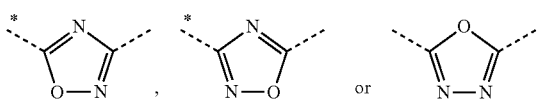

wherein the asterisks indicate the bond that is linked to the pyridine group of Formula (I);

$R^1$ represents cyclopentyl;
$R^2$ represents methyl, and $R^4$ represents ethyl or chloro; or
$R^2$ represents methoxy, and $R^4$ represents chloro;

$R^3$ represents —$OCH_2COOH$, —$OCH_2CH_2CH_2COOH$, —$OCH_2CONHCH_2CH_2OH$, —$OCH_2CH_2CH_2CONHCH_2CH_2OH$, —$OCH_2$—$(CH_2)_n$—NH—$(CH_2)_m$—COOH, —$OCH_2$—$(CH_2)_n$—N($CH_3$)—$(CH_2)_m$—COOH, 2-[(azetidine-3-carboxylic acid)-1-yl]-ethoxy, 2-[(pyrrolidin-3-carboxylic acid)-1-yl]-ethoxy, 3-[(azetidine-3-carboxylic acid)-1-yl]-propoxy, 3-[(pyrrolidin-3-carboxylic acid)-1-yl]-propoxy, —$OCH_2CH(OH)$—$CH_2NH$—$CH_2COOH$, —$OCH_2CH(OH)$—$CH_2NH$—$CH_2CH_2COOH$, —$OCH_2CH(OH)$—$CH_2N(CH_3)$—$CH_2COOH$, —$OCH_2CH(OH)$—$CH_2N(CH_3)$—$CH_2CH_2COOH$, 3-[(azetidine-3-carboxylic acid)-1-yl]-2-hydroxy-propoxy, 2-hydroxy-3-[(pyrrolidin-3-carboxylic acid)-1-yl]-propoxy, —$OCH_2$—$(CH_2)_n$—NH—$CH_2CH_2OH$, —$OCH_2$—$(CH_2)_n$—NH—$CH(CH_2OH)_2$, —$OCH_2$—$(CH_2)_n$—NH—$CH_2CH(OH)$—$CH_2OH$, —$OCH_2CH(OH)$—$CH_2NH$—$CH_2CH_2OH$, —$OCH_2CH(OH)$—$CH_2NH$—$CH(CH_2OH)_2$, —$OCH_2$—$(CH_2)_k$—NH—CO—$CH_2OH$, —$OCH_2$—$(CH_2)_n$—NH—CO—$CH_2COOH$, —$OCH_2$—$(CH_2)_n$—NH—CO—$CH_2CH_2COOH$, —$OCH_2CH(OH)$—$CH_2NH$—CO—$(CH_2)$—COOH, —$OCH_2$—$(CH_2)_n$—N($CH_3$)—CO—$CH_2OH$, —$OCH_2$—$(CH_2)_n$—N($CH_3$)—CO—$CH_2COOH$, or —$OCH_2$—$(CH_2)_n$—N($CH_3$)—CO—$CH_2CH_2COOH$;

n independently represents 1 or 2;
m independently represents 1, 2, or 3; and
k represents 1 or 2;
or a salt thereof.

2. A compound according to claim 1, wherein the stereocenter of the $R^3$ groups 2-[(pyrrolidin-3-carboxylic acid)-1-yl]-ethoxy, 3-[(pyrrolidin-3-carboxylic acid)-1-yl]-propoxy, —O—$CH_2CH(OH)$—$CH_2NH$—$CH_2COOH$, —$OCH_2CH(OH)$—$CH_2NH$—$CH_2CH_2COOH$, —$OCH_2CH(OH)$—$CH_2N(CH_3)$—$CH_2COOH$, —$OCH_2CH(OH)$—$CH_2N(CH_3)$—$CH_2CH_2COOH$, 3-[(azetidine-3-carboxylic acid)-1-yl]-2-hydroxy-propoxy, —$OCH_2$—$(CH_2)_n$—NH—$CH_2CH(OH)$—$CH_2OH$, —$OCH_2CH(OH)$—$CH_2NH$—$CH_2CH_2OH$, —$OCH_2CH(OH)$—$CH_2NH$—$CH(CH_2OH)_2$, and —$OCH_2CH(OH)$—$CH_2NH$—CO—$(CH_2)$—COOH is in the S-configuration, or a salt of such compound.

3. A compound according to claim 1, wherein the stereocenter of the $R^3$ groups 2-[(pyrrolidin-3-carboxylic acid)-1-yl]-ethoxy, 3-[(pyrrolidin-3-carboxylic acid)-1-yl]-propoxy, —O—$CH_2CH(OH)$—$CH_2NH$—$CH_2COOH$, —$OCH_2CH(OH)$—$CH_2NH$—$CH_2CH_2COOH$, —$OCH_2CH(OH)$—

CH₂N(CH₃)—CH₂COOH, —OCH₂CH(OH)—CH₂N(CH₃)—CH₂CH₂COOH, 3-[(azetidine-3-carboxylic acid)-1-yl]-2-hydroxy-propoxy, —OCH₂—(CH₂)$_n$—NH—CH₂CH(OH)—CH₂OH, —OCH₂CH(OH)—CH₂NH—CH₂CH₂OH, —OCH₂CH(OH)—CH₂NH—CH(CH₂OH)₂, and —OCH₂CH(OH)—CH₂NH—CO—(CH₂)$_n$—COOH is in the R-configuration, or a salt of such compound.

4. A compound according to claim 1, wherein A represents

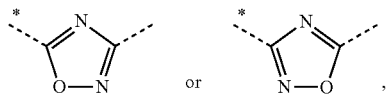

wherein the asterisks indicate the bond that is linked to the pyridine group of Formula (I), or a salt of such compound.

5. A compound according to claim 1, wherein A represents

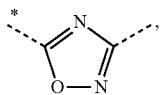

wherein the asterisk indicates the bond that is linked to the pyridine group of Formula (I), or a salt of such compound.

6. A compound according to claim 1, wherein A represents

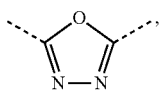

or a salt of such compound.

7. A compound according to claim 1, wherein R² represents methyl, and R⁴ represents ethyl or chloro, or a salt of such compound.

8. A compound according to claim 1, wherein R² represents methyl, and R⁴ represents ethyl, or a salt of such compound.

9. A compound according to claim 1, wherein R² represents methoxy, and R⁴ represents chloro, or a salt of such compound.

10. A compound according to claim 1, wherein R³ represents —OCH₂COOH, —OCH₂CH₂CH₂COOH, —OCH₂CONHCH₂CH₂OH, —OCH₂CH₂CH₂CONHCH₂CH₂OH, —OCH₂—(CH₂)$_n$—NH—(CH₂)$_m$—COOH, —OCH₂—(CH₂)$_n$—N(CH₃)—(CH₂)$_m$—COOH, 2-[(azetidine-3-carboxylic acid)-1-yl]-ethoxy, 2-[(pyrrolidin-3-carboxylic acid)-1-yl]-ethoxy, 3-[(azetidine-3-carboxylic acid)-1-yl]-propoxy, —OCH₂CH(OH)—CH₂NH—CH₂COOH, —OCH₂CH(OH)—CH₂NH—CH₂CH₂COOH, —OCH₂CH(OH)—CH₂N(CH₃)—CH₂COOH, 3-[(azetidine-3-carboxylic acid)-1-yl]-2-hydroxy-propoxy, —OCH₂—(CH₂)$_n$—NH—CH₂CH₂OH, —OCH₂—(CH₂)$_n$—NH—CH(CH₂OH)₂, —OCH₂—(CH₂)$_n$—NH—CH₂CH(OH)—CH₂OH, —OCH₂CH(OH)—CH₂NH—CH₂CH₂OH, —OCH₂CH(OH)—CH₂NH—CH(CH₂OH)₂, —OCH₂—(CH₂)$_k$—NH—CO—CH₂OH, —OCH₂—(CH₂)$_n$—NH—CO—CH₂COOH, —OCH₂—(CH₂)$_n$—NH—CO—CH₂CH₂COOH, —OCH₂CH(OH)—CH₂NH—CO(CH₂)—COOH, —OCH₂—(CH₂)$_n$—N(CH₃)—CO—CH₂OH, —OCH₂—(CH₂)$_n$—N(CH₃)—CO—CH₂COOH, or —OCH₂—(CH₂)$_n$—N(CH₃)—CO—CH₂CH₂COOH, or a salt of such compound.

11. A compound according to claim 1, wherein R³ represents —OCH₂COOH, —OCH₂CH₂CH₂COOH, —OCH₂CONHCH₂CH₂OH, —OCH₂CH₂CH₂CONHCH₂CH₂OH, —OCH₂—(CH₂)$_n$—NH—(CH₂)$_m$—COOH, —OCH₂—(CH₂)$_n$—N(CH₃)—(CH₂)$_m$—COOH, 2-[(azetidine-3-carboxylic acid)-1-yl]-ethoxy, 2-[(pyrrolidin-3-carboxylic acid)-1-yl]-ethoxy, 3-[(azetidine-3-carboxylic acid)-1-yl]-propoxy, 3-[(pyrrolidin-3-carboxylic acid)-1-yl]-propoxy, —O—CH₂CH(OH)—CH₂NH—CH₂COOH, —OCH₂CH(OH)—CH₂NH—CH₂CH₂COOH, —OCH₂CH(OH)—CH₂N(CH₃)—CH₂COOH, —OCH₂CH(OH)—CH₂N(CH₃)—CH₂CH₂COOH, 3-[(azetidine-3-carboxylic acid)-1-yl]-2-hydroxy-propoxy, 2-hydroxy-3-[(pyrrolidin-3-carboxylic acid)-1-yl]-propoxy, —OCH₂—(CH₂)$_n$—NH—CH₂CH₂OH, —OCH₂—(CH₂)$_n$—NH—CH(CH₂OH)₂, —OCH₂—(CH₂)$_n$—NH—CH₂CH(OH)—CH₂OH, —OCH₂CH(OH)—CH₂NH—CH₂CH₂OH, —O—CH₂CH(OH)—CH₂NH—CH(CH₂OH)₂, —OCH₂—(CH₂)$_k$—NH—CO—CH₂OH, or —OCH₂—(CH₂)$_k$—N(CH₃)—CO—CH₂OH, or a salt of such compound.

12. A compound according to claim 1, wherein R³ represents —OCH₂COOH, —OCH₂CH₂CH₂COOH, —OCH₂CONHCH₂CH₂OH, —OCH₂CH₂CH₂CONHCH₂CH₂OH, —OCH₂—(CH₂)$_n$—NH—(CH₂)$_m$—COOH, —OCH₂—(CH₂)$_n$—N(CH₃)—(CH₂)$_m$—COOH, 2-[(azetidine-3-carboxylic acid)-1-yl]-ethoxy, 2-[(pyrrolidin-3-carboxylic acid)-1-yl]-ethoxy, 3-[(azetidine-3-carboxylic acid)-1-yl]-propoxy, 3-[(pyrrolidin-3-carboxylic acid)-1-yl]-propoxy, —OCH₂CH(OH)—CH₂N(CH₃)—CH₂COOH, —OCH₂CH(OH)—CH₂N(CH₃)—CH₂CH₂COOH, 3-[(azetidine-3-carboxylic acid)-1-yl]-2-hydroxy-propoxy, 2-hydroxy-3-[(pyrrolidin-3-carboxylic acid)-1-yl]-propoxy, —OCH₂—(CH₂)$_n$—NH—CH₂CH₂OH, —OCH₂—(CH₂)$_n$—NH—CH(CH₂OH)₂, —OCH₂CH(OH)—CH₂NH—CH₂CH₂OH, —O—CH₂CH(OH)—CH₂NH—CH(CH₂OH)₂, —OCH₂—(CH₂)$_n$—NH—CO—CH₂COOH, —OCH₂—(CH₂)$_n$—NH—CO—CH₂CH₂COOH, —O—CH₂CH(OH)—CH₂NH—CO—(CH₂)—COOH, —OCH₂—(CH₂)$_n$—N(CH₃)—CO—CH₂COOH, or —OCH₂—(CH₂)$_n$—N(CH₃)—CO—CH₂CH₂COOH, or a salt of such compound.

13. A compound according to claim 1, wherein R³ represents —OCH₂COOH, —OCH₂CH₂CH₂COOH, —OCH₂CONHCH₂CH₂OH, —OCH₂CH₂CH₂CONHCH₂CH₂OH, —OCH₂—(CH₂)$_n$—NH—(CH₂)$_m$—COOH, —OCH₂—(CH₂)$_n$—N(CH₃)—(CH₂)$_m$—COOH, 2-[(azetidine-3-carboxylic acid)-1-yl]-ethoxy, 3-[(azetidine-3-carboxylic acid)-1-yl]-propoxy, —OCH₂CH(OH)—CH₂N(CH₃)—CH₂COOH, —OCH₂CH(OH)—CH₂N(CH₃)—CH₂CH₂COOH, 3-[(azetidine-3-carboxylic acid)-1-yl]-2-hydroxy-propoxy, —OCH₂—(CH₂)$_n$—NH—CH₂CH₂OH, —OCH₂—(CH₂)$_n$—NH—CH(CH₂OH)₂, —O—CH₂CH(OH)—CH₂NH—CH₂CH₂OH, —OCH₂CH(OH)—CH₂NH—CH(CH₂OH)₂, —OCH₂—(CH₂)$_k$—NH—CO—CH₂OH, —OCH₂—(CH₂)$_n$—NH—CO—CH₂COOH, —OCH₂—(CH₂)$_n$—NH—CO—CH₂CH₂COOH, —OCH₂CH(OH)—CH₂NH—CO—(CH₂)—COOH, —OCH₂—(CH₂)$_n$—N(CH₃)—CO—CH₂COOH, or —OCH₂—(CH₂)$_n$—N(CH₃)—CO—CH₂CH₂COOH, or a salt of such compound.

14. A compound according to claim 1, wherein R³ represents —OCH₂COOH, —OCH₂CH₂CH₂COOH, —OCH₂—(CH₂)$_n$—NH—(CH₂)$_m$—COOH, —OCH₂—(CH₂)$_n$—N (CH₃)—(CH₂)ₘ—COOH, 2-[(azetidine-3-carboxylic acid)-1-yl]-ethoxy, 3-[(azetidine-3-carboxylic acid)-1-yl]-propoxy, or 3-[(azetidine-3-carboxylic acid)-1-yl]-2-hydroxy-propoxy, or a salt of such compound.

15. A compound according to claim 1, wherein R³ represents —OCH₂CONHCH₂CH₂OH, —OCH₂CH₂CH₂CONHCH₂CH₂OH, —OCH₂CH(OH)—CH₂N(CH₃)—CH₂COOH, —OCH₂CH(OH)—CH₂N(CH₃)—CH₂CH₂COOH, 3-[(azetidine-3-carboxylic acid)-1-yl]-2-hydroxy-propoxy, —OCH₂—(CH₂)ₙ—NH—CH₂CH₂OH, —OCH₂—(CH₂)ₙ—NH—CH(CH₂OH)₂, —O—CH₂CH(OH)—CH₂NH—CH₂CH₂OH, or —O—CH₂CH(OH)—CH₂NH—CH(CH₂OH)₂, or a salt of such compound.

16. A compound according to claim 1, wherein m represents 1 or 2, or a salt of such compound.

17. A compound according to claim 1, wherein n represents 1, or a salt of such compound.

18. A compound according to claim 1, wherein
A represents

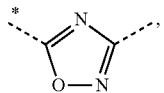

wherein the asterisk indicates the bond that is linked to the pyridine group of Formula (I);
R¹ represents cyclopentyl;
R² represents methyl, and R⁴ represents ethyl or chloro; or
R² represents methoxy, and R⁴ represents chloro; and
R³ represents —OCH₂COOH, —OCH₂CH₂CH₂COOH, —OCH₂CONHCH₂CH₂OH, —OCH₂CH₂CH₂CONHCH₂CH₂OH, —OCH₂—(CH₂)₁₋₂—NH—(CH₂)₁₋₂—COOH, —OCH₂—CH₂—NH—(CH₂)₃—COOH, —OCH₂—(CH₂)₁₋₂—N(CH₃)—(CH₂)₁₋₂—COOH, 2-[(azetidine-3-carboxylic acid)-1-yl]-ethoxy, 2-[(pyrrolidin-3-carboxylic acid)-1-yl]-ethoxy, 3-[(azetidine-3-carboxylic acid)-1-yl]-propoxy, —OCH₂CH(OH)—CH₂NH—CH₂COOH, —OCH₂CH(OH)—CH₂NH—CH₂CH₂COOH, —OCH₂CH(OH)—CH₂N(CH₃)—CH₂COOH, 3-[(azetidine-3-carboxylic acid)-1-yl]-2-hydroxy-propoxy, —OCH₂—(CH₂)₁₋₂—NH—CH₂CH₂OH, —OCH₂—(CH₂)₁₋₂—NH—CH(CH₂OH)₂, —OCH₂—(CH₂)₁₋₂—NH—CH₂CH(OH)—CH₂OH, —OCH₂CH(OH)—CH₂NH—CH₂CH₂OH, —OCH₂CH(OH)—CH₂NH—CH(CH₂OH)₂, —OCH₂—(CH₂)₂—NH—CO—CH₂OH, —OCH₂—(CH₂)₂—NH—CO—CH₂COOH, —OCH₂—(CH₂)₂—NH—CO—CH₂CH₂COOH, —OCH₂CH(OH)—CH₂NH—CO—(CH₂)₁₋₂COOH, —OCH₂—(CH₂)₂—N(CH₃)—CO—CH₂OH, —OCH₂—(CH₂)₂—N(CH₃)—CO—CH₂COOH, or —OCH₂—(CH₂)₂—N(CH₃)—CO—CH₂CH₂COOH, or a salt of such compound.

19. A compound according to claim 1, wherein R³ represents —OCH₂COOH, —OCH₂CH₂CH₂COOH, —OCH₂CONHCH₂CH₂OH, —OCH₂CH₂CH₂CONHCH₂CH₂OH, —OCH₂—(CH₂)₁₋₂—NH—(CH₂)₁₋₂—COOH, —OCH₂—CH₂—NH—(CH₂)₃—COOH, —OCH₂—(CH₂)₁₋₂—N(CH₃)—(CH₂)₁₋₂—COOH, 2-[(azetidine-3-carboxylic acid)-1-yl]-ethoxy, 2-[(pyrrolidin-3-carboxylic acid)-1-yl]-ethoxy, 3-[(azetidine-3-carboxylic acid)-1-yl]-propoxy, —OCH₂CH(OH)—CH₂NH—CH₂COOH, —OCH₂CH(OH)—CH₂NH—CH₂CH₂COOH, —OCH₂CH(OH)—CH₂N(CH₃)—CH₂COOH, —OCH₂CH(OH)—CH₂N(CH₃)—CH₂CH₂COOH, 3-[(azetidine-3-carboxylic acid)-1-yl]-2-hydroxy-propoxy, —OCH₂—(CH₂)₁₋₂—NH—CH₂CH₂OH, —OCH₂—(CH₂)₁₋₂—NH—CH(CH₂OH)₂, —OCH₂—(CH₂)₁₋₂—NH—CH₂CH(OH)—CH₂OH, —OCH₂CH(OH)—CH₂NH—CH₂CH₂OH, —OCH₂CH(OH)—CH₂NH—CH(CH₂OH)₂, —OCH₂—(CH₂)₂—NH—CO—CH₂OH, —OCH₂—(CH₂)₁₋₂—NH—CO—CH₂COOH, —OCH₂—(CH₂)₁₋₂—NH—CO—CH₂CH₂COOH, —OCH₂CH(OH)—CH₂NH—CO—(CH₂)₁₋₂COOH, —OCH₂—(CH₂)₂—N(CH₃)—CO—CH₂OH, —OCH₂—(CH₂)₂—N(CH₃)—CO—CH₂COOH, or —OCH₂—(CH₂)₂—N(CH₃)—CO—CH₂CH₂COOH, or a salt of such compound.

20. A compound according to claim 1 selected from the group consisting of:
3-(2-{4-[5-(2-cyclopentyl-6-methoxy-pyridin-4-yl)-[1,2,4]oxadiazol-3-yl]-2-ethyl-6-methyl-phenoxy}-ethylamino)-propionic acid,
1-(2-{4-[5-(2-cyclopentyl-6-methoxy-pyridin-4-yl)-[1,2,4]oxadiazol-3-yl]-2-ethyl-6-methyl-phenoxyl}-ethyl)-azetidine-3-carboxylic acid,
(S)-1-{4-[5-(2-cyclopentyl-6-methoxy-pyridin-4-yl)-[1,2,4]oxadiazol-3-yl]-2-ethyl-6-methyl-phenoxy}-3-(2-hydroxy-ethylamino)-propan-2-ol,
2-((S)-3-{4-[5-(2-cyclopentyl-6-methoxy-pyridin-4-yl)-[1,2,4]oxadiazol-3-yl]-2-ethyl-6-methyl-phenoxy}-2-hydroxy-propylamino)-propane-1,3-diol,
{4-[5-(2-cyclopentyl-6-methoxy-pyridin-4-yl)-[1,2,4]oxadiazol-3-yl]-2-ethyl-6-methyl-phenoxy}-acetic acid,
4-{4-[5-(2-cyclopentyl-6-methoxy-pyridin-4-yl)-[1,2,4]oxadiazol-3-yl]-2-ethyl-6-methyl-phenoxy}-butyric acid,
(2-{4-[5-(2-cyclopentyl-6-methoxy-pyridin-4-yl)-[1,2,4]oxadiazol-3-yl]-2-ethyl-6-methyl-phenoxy}-ethylamino)-acetic acid,
1-(2-{4-[5-(2-cyclopentyl-6-methoxy-pyridin-4-yl)-[1,2,4]oxadiazol-3-yl]-2-ethyl-6-methyl-phenoxy}-ethyl)-pyrrolidine-3-carboxylic acid,
((S)-3-{4-[5-(2-cyclopentyl-6-methoxy-pyridin-4-yl)-[1,2,4]oxadiazol-3-yl]-2-ethyl-6-methyl-phenoxy}-2-hydroxy-propylamino)-acetic acid,
3-((S)-3-{4-[5-(2-cyclopentyl-6-methoxy-pyridin-4-yl)-[1,2,4]oxadiazol-3-yl]-2-ethyl-6-methyl-phenoxy}-2-hydroxy-propylamino)-propionic acid,
[((S)-3-{4-[5-(2-cyclopentyl-6-methoxy-pyridin-4-yl)-[1,2,4]oxadiazol-3-yl]-2-ethyl-6-methyl-phenoxy}-2-hydroxy-propyl)-methyl-amino]-acetic acid,
1-((S)-3-{4-[5-(2-cyclopentyl-6-methoxy-pyridin-4-yl)-[1,2,4]oxadiazol-3-yl]-2-ethyl-6-methyl-phenoxy}-2-hydroxy-propyl)-azetidine-3-carboxylic acid,
2-{4-[5-(2-cyclopentyl-6-methoxy-pyridin-4-yl)-[1,2,4]oxadiazol-3-yl]-2-ethyl-6-methyl-phenoxy}-N-(2-hydroxy-ethyl)-acetamide,
N—((S)-3-{4-[5-(2-cyclopentyl-6-methoxy-pyridin-4-yl)-[1,2,4]oxadiazol-3-yl]-2-ethyl-6-methyl-phenoxy}-2-hydroxy-propyl)-malonamic acid,
N—((S)-3-{4-[5-(2-cyclopentyl-6-methoxy-pyridin-4-yl)-[1,2,4]oxadiazol-3-yl]-2-ethyl-6-methyl-phenoxy}-2-hydroxy-propyl)-succinamic acid,
[(2-{4-[5-(2-cyclopentyl-6-methoxy-pyridin-4-yl)-[1,2,4]oxadiazol-3-yl]-2-ethyl-6-methyl-phenoxy}-ethyl)-methyl-amino]-acetic acid,
3-[(2-{4-[5-(2-cyclopentyl-6-methoxy-pyridin-4-yl)-[1,2,4]oxadiazol-3-yl]-2-ethyl-6-methyl-phenoxy}-ethyl)-methyl-amino]-propionic acid, (3-{4-[5-(2-cyclopentyl-6-methoxy-pyridin-4-yl)-[1,2,4]
  oxadiazol-3-yl]-2-ethyl-6-methyl-phenoxy}-propy-
  lamino)-acetic acid,
3-(3-{4-[5-(2-cyclopentyl-6-methoxy-pyridin-4-yl)-[1,2,
  4]oxadiazol-3-yl]-2-ethyl-6-methyl-phenoxy}-propy-
  lamino)-propionic acid,
[(3-{4-[5-(2-cyclopentyl-6-methoxy-pyridin-4-yl)-[1,2,4]
  oxadiazol-3-yl]-2-ethyl-6-methyl-phenoxy}-propyl)-
  methyl-amino]-acetic acid,
3-[(3-{4-[5-(2-cyclopentyl-6-methoxy-pyridin-4-yl)-[1,2,
  4]oxadiazol-3-yl]-2-ethyl-6-methyl-phenoxy}-propyl)-
  methyl-amino]-propionic acid,
1-(3-{4-[5-(2-cyclopentyl-6-methoxy-pyridin-4-yl)-[1,2,
  4]oxadiazol-3-yl]-2-ethyl-6-methyl-phenoxy}-propyl)-
  azetidine-3-carboxylic acid,
2-(2-{4-[5-(2-cyclopentyl-6-methoxy-pyridin-4-yl)-[1,2,
  4]oxadiazol-3-yl]-2-ethyl-6-methyl-phenoxy}-ethy-
  lamino)-ethanol,
2-(3-{4-[5-(2-cyclopentyl-6-methoxy-pyridin-4-yl)-[1,2,
  4]oxadiazol-3-yl]-2-ethyl-6-methyl-phenoxy}-propy-
  lamino)-ethanol,
2-{2-{4-[5-(2-cyclopentyl-6-methoxy-pyridin-4-yl)-[1,2,
  4]oxadiazol-3-yl]-2-ethyl-6-methyl-phenoxy}-ethy-
  lamino)-propane-1,3-diol,
2-(3-{4-[5-(2-cyclopentyl-6-methoxy-pyridin-4-yl)-[1,2,
  4]oxadiazol-3-yl]-2-ethyl-6-methyl-phenoxy}-propy-
  lamino)-propane-1,3-diol,
3-(2-{4-[5-(2-cyclopentyl-6-methoxy-pyridin-4-yl)-[1,2,
  4]oxadiazol-3-yl]-2-ethyl-6-methyl-phenoxy}-ethy-
  lamino)-propane-1,2-diol,
3-(3-{4-[5-(2-cyclopentyl-6-methoxy-pyridin-4-yl)-[1,2,
  4]oxadiazol-3-yl]-2-ethyl-6-methyl-phenoxy}-propy-
  lamino)-propane-1,2-diol,
N-(3-{4-[5-(2-cyclopentyl-6-methoxy-pyridin-4-yl)-[1,2,
  4]oxadiazol-3-yl]-2-ethyl-6-methyl-phenoxy}-propyl)-
  2-hydroxy-acetamide,
N-(3-{4-[5-(2-cyclopentyl-6-methoxy-pyridin-4-yl)-[1,2,
  4]oxadiazol-3-yl]-2-ethyl-6-methyl-phenoxy}-propyl)-
  2-hydroxy-N-methyl-acetamide,
N-(3-{4-[5-(2-cyclopentyl-6-methoxy-pyridin-4-yl)-[1,2,
  4]oxadiazol-3-yl]-2-ethyl-6-methyl-phenoxy}-propyl)-
  malonamic acid,
N-(3-{4-[5-(2-cyclopentyl-6-methoxy-pyridin-4-yl)-[1,2,
  4]oxadiazol-3-yl]-2-ethyl-6-methyl-phenoxy}-propyl)-
  succinamic acid,
N-(3-{4-[5-(2-cyclopentyl-6-methoxy-pyridin-4-yl)-[1,2,
  4]oxadiazol-3-yl]-2-ethyl-6-methyl-phenoxy}-propyl)-
  N-methyl-malonamic acid,
N-(3-{4-[5-(2-cyclopentyl-6-methoxy-pyridin-4-yl)-[1,2,
  4]oxadiazol-3-yl]-2-ethyl-6-methyl-phenoxy}-propyl)-
  N-methyl-succinamic acid,
4-{2-chloro-4-[5-(2-cyclopentyl-6-methoxy-pyridin-4-
  yl)-[1,2,4]oxadiazol-3-yl]-6-methoxy-phenoxy}-bu-
  tyric acid,
4-{2-chloro-4-[5-(2-cyclopentyl-6-methoxy-pyridin-4-
  yl)-[1,2,4]oxadiazol-3-yl]-6-methoxy-phenoxy}-N-(2-
  hydroxy-ethyl)-butyramide,
3-(2-{2-chloro-4-[5-(2-cyclopentyl-6-methoxy-pyridin-
  4-yl)-[1,2,4]oxadiazol-3-yl]-6-methoxy-phenoxy}-
  ethylamino)-propionic acid,
N-(3-{2-chloro-4-[5-(2-cyclopentyl-6-methoxy-pyridin-
  4-yl)-[1,2,4]oxadiazol-3-yl]-6-methoxy-phenoxy}-
  propyl)-2-hydroxy-acetamide,
4-((2-(4-(5-(2-cyclopentyl-6-methoxypyridin-4-yl)-1,2,4-
  oxadiazol-3-yl)-2-ethyl-6-methylphenoxy)ethyl)
  amino)butanoic acid, and
4-(2-chloro-4-(5-(2-cyclopentyl-6-methoxypyridin-4-yl)-
  1,2,4-oxadiazol-3-yl)-6-methylphenoxy)butanoic acid,
or a salt of such compounds.

21. A compound according to claim 1 selected from the group consisting of:
2-(2-chloro-4-(5-(2-cyclopentyl-6-methoxypyridin-4-yl)-
  1,2,4-oxadiazol-3-yl)-6-methylphenoxy)acetic acid,
2-(2-chloro-4-(5-(2-cyclopentyl-6-methoxypyridin-4-yl)-
  1,2,4-oxadiazol-3-yl)-6-methyl-phenoxy)-N-(2-hy-
  droxyethyl)acetamide,
3-((2-(2-chloro-4-(5-(2-cyclopentyl-6-methoxypyridin-4-
  yl)-1,2,4-oxadiazol-3-yl)-6-methylphenoxy)ethyl)
  amino)propanoic acid,
1-(2-(2-chloro-4-(5-(2-cyclopentyl-6-methoxypyridin-4-
  yl)-1,2,4-oxadiazol-3-yl)-6-methylphenoxy)ethyl)aze-
  tidine-3-carboxylic acid,
2-((2-(2-chloro-4-(5-(2-cyclopentyl-6-methoxypyridin-4-
  yl)-1,2,4-oxadiazol-3-yl)-6-methylphenoxy)ethyl)
  amino)ethanol,
4-(4-(5-(2-cyclopentyl-6-methoxypyridin-4-yl)-1,2,4-
  oxadiazol-3-yl)-2-ethyl-6-methylphenoxy)-N-(2-hy-
  droxyethyl)butanamide,
(S)-3-((3-(4-(5-(2-cyclopentyl-6-methoxypyridin-4-yl)-1,
  2,4-oxadiazol-3-yl)-2-ethyl-6-methylphenoxy)-2-hy-
  droxypropyl)(methyl)amino)propanoic acid,
(R)-3-((3-(4-(5-(2-cyclopentyl-6-methoxypyridin-4-yl)-
  1,2,4-oxadiazol-3-yl)-2-ethyl-6-methylphenoxy)-2-hy-
  droxypropyl)(methyl)amino)propanoic acid,
3-((2-(4-(5-(2-cyclopentyl-6-methoxypyridin-4-yl)-1,2,4-
  oxadiazol-3-yl)-2-ethyl-6-methylphenoxy)ethyl)
  amino)-3-oxopropanoic acid,
4-((2-(4-(5-(2-cyclopentyl-6-methoxypyridin-4-yl)-1,2,4-
  oxadiazol-3-yl)-2-ethyl-6-methylphenoxy)ethyl)
  amino)-4-oxobutanoic acid,
2-((2-(2-chloro-4-(5-(2-cyclopentyl-6-methoxypyridin-4-
  yl)-1,2,4-oxadiazol-3-yl)-6-methoxyphenoxy)ethyl)
  amino)acetic acid,
1-(2-(2-chloro-4-(5-(2-cyclopentyl-6-methoxypyridin-4-
  yl)-1,2,4-oxadiazol-3-yl)-6-methoxyphenoxy)ethyl)
  azetidine-3-carboxylic acid,
2-(4-(3-(2-cyclopentyl-6-methoxypyridin-4-yl)-1,2,4-
  oxadiazol-5-yl)-2-ethyl-6-methylphenoxy)acetic acid,
4-(4-(3-(2-cyclopentyl-6-methoxypyridin-4-yl)-1,2,4-
  oxadiazol-5-yl)-2-ethyl-6-methylphenoxy)butanoic
  acid,
2-((2-(4-(3-(2-cyclopentyl-6-methoxypyridin-4-yl)-1,2,4-
  oxadiazol-5-yl)-2-ethyl-6-methylphenoxy)ethyl)
  amino)acetic acid,
2-((2-(4-(3-(2-cyclopentyl-6-methoxypyridin-4-yl)-1,2,4-
  oxadiazol-5-yl)-2-ethyl-6-methylphenoxy)ethyl)(me-
  thyl)amino)acetic acid,
3-((2-(4-(3-(2-cyclopentyl-6-methoxypyridin-4-yl)-1,2,4-
  oxadiazol-5-yl)-2-ethyl-6-methylphenoxy)ethyl)
  amino)propanoic acid,
1-(2-(4-(3-(2-cyclopentyl-6-methoxypyridin-4-yl)-1,2,4-
  oxadiazol-5-yl)-2-ethyl-6-methylphenoxy)ethyl)azeti-
  dine-3-carboxylic acid,
2-((3-(4-(3-(2-cyclopentyl-6-methoxypyridin-4-yl)-1,2,4-
  oxadiazol-5-yl)-2-ethyl-6-methylphenoxy)propyl)
  amino)acetic acid,
2-(4-(5-(2-cyclopentyl-6-methoxypyridin-4-yl)-1,3,4-
  oxadiazol-2-yl)-2-ethyl-6-methylphenoxy)acetic acid,
4-(4-(5-(2-cyclopentyl-6-methoxypyridin-4-yl)-1,3,4-
  oxadiazol-2-yl)-2-ethyl-6-methylphenoxy)butanoic
  acid, 3-((2-(4-(5-(2-cyclopentyl-6-methoxypyridin-4-yl)-1,3,4-oxadiazol-2-yl)-2-ethyl-6-methylphenoxy)ethyl)amino)propanoic acid, 1-(2-(4-(5-(2-cyclopentyl-6-methoxypyridin-4-yl)-1,3,4-oxadiazol-2-yl)-2-ethyl-6-methylphenoxy)ethyl)azetidine-3-carboxylic acid, (S)-1-(4-(5-(2-cyclopentyl-6-methoxypyridin-4-yl)-1,3,4-oxadiazol-2-yl)-2-ethyl-6-methylphenoxy)-3-(2-hydroxyethyl)amino)propan-2-ol, (S)-2-((3-(4-(5-(2-cyclopentyl-6-methoxypyridin-4-yl)-1,3,4-oxadiazol-2-yl)-2-ethyl-6-methylphenoxy)-2-hydroxypropyl)amino)propane-1,3-diol, and (S)-4-((3-(4-(5-(2-cyclopentyl-6-methoxypyridin-4-yl)-1,3,4-oxadiazol-2-yl)-2-ethyl-6-methylphenoxy)-2-hydroxypropyl)amino)-4-oxobutanoic acid, or a salt of such compounds.

22. A pharmaceutical composition comprising a compound according to claim 1, or a pharmaceutically acceptable salt thereof, and a pharmaceutically acceptable carrier.

23. A method of reducing the number of circulating and infiltrating T- and B-lymphocytes in a patient in need thereof, comprising administering to the patient a pharmaceutically active amount of a compound according to claim 1, or a pharmaceutically acceptable salt thereof.

* * * * *